United States Patent [19]
Bennett et al.

[11] Patent Number: 6,111,094
[45] Date of Patent: *Aug. 29, 2000

[54] ENHANCED ANTISENSE MODULATION OF ICAM-1

[75] Inventors: C. Frank Bennett; Thomas P. Condon, both of Carlsbad; Shin Cheng Flournoy, San Diego, all of Calif.

[73] Assignee: Isis Pharmaceuticals Inc., Carlsbad, Calif.

[ * ] Notice: This patent is subject to a terminal disclaimer.

[21] Appl. No.: 09/062,416

[22] Filed: Apr. 17, 1998

Related U.S. Application Data

[63] Continuation-in-part of application No. 08/440,740, May 12, 1995, Pat. No. 5,843,738, which is a continuation-in-part of application No. 08/063,167, May 17, 1993, Pat. No. 5,514,788, which is a continuation of application No. 07/969,151, Feb. 10, 1993, abandoned, which is a continuation-in-part of application No. 08/007,997, Jan. 21, 1993, Pat. No. 5,591,623, which is a continuation-in-part of application No. 07/939,855, Sep. 2, 1992, abandoned, which is a continuation-in-part of application No. 07/567,286, Aug. 14, 1990, abandoned.

[51] Int. Cl.[7] ................................................ C07H 21/00
[52] U.S. Cl. ........................... 536/24.5; 435/6; 435/375; 514/44; 536/24.31
[58] Field of Search ............................. 435/6, 91.5, 375, 435/325, 366; 536/23.1, 24.3, 24.31, 24.33, 24.5; 514/44

[56] References Cited

U.S. PATENT DOCUMENTS

| | | | |
|---|---|---|---|
| 5,514,788 | 5/1996 | Bennett et al. | 536/23.1 |
| 5,580,969 | 12/1996 | Hoke et al. | 536/24.5 |
| 5,591,623 | 1/1997 | Bennett et al. | 435/325 |
| 5,789,573 | 8/1998 | Baker et al. | 536/24.5 |
| 5,843,738 | 12/1998 | Bennett et al. | 435/375 |
| 5,852,188 | 12/1998 | Cook | 536/24.5 |

OTHER PUBLICATIONS

Manoharan et al. Nucleosides & Nucleotides 14(3–5):969–973, 1995.
Condon et al. Fabseb Journal 8(4–5): pA972,#5626, 1994.
Sanghvi, Y. Antisense Research & Applications, CH 15, pp. 274–285, CRC Press, 1993.
Walden et al. PNAS 85: 5011–5015, 1988.
Martin, V.P. Helvetica Chimica Acta 78:486–504, 1995.
Branch TIBS 23:45–50, 1998.
Crooke Ch 1 in Antisense Research & Application Syringes, NY, 1998 pp. 1–50.
Wegner et al., "Intercellular Adhesion Molecule–1 (ICAM–1) in the Pathogenesis of Asthma", Science, 1990, 247, 456.
Van de Stolpe et al., "Intercellular adhesion molecule–1", J. Mol. Med., 1996, 74, 13–33.
Albelda, et al., "Adhesion molecules and inflammatory injury", FASEB J., 1994, 8, 504.
Ballantyne et al., "Nucleotide sequence of the cDNA for murine intercellular adhesion molecule–1 (ICAM–1)", Nucleic Acids Research, 1989, 17, 5853.
Ballantyne et al., "Characterize of the Murine Icam–1 Gene", Genomics, 1992, 14, 1076.
Bennett et al., "An ICAM–1 Antisense Oligonucleotide Prevents and Reverses Dextran Sulfate Sodium–Induced Colitis in Mice", J. Pharm. Exp. Therapeutics, 1997, 280, 988.
Bennett et al., "Inhibition of Endothelial Cell Adhesion Molecule Expression with Antisense Oligonucleotides", J. Immunol., 1994, 152, 3530.
Cosimi et al., "In Vivo Effects of Monoclonal Antibody To ICAM–1 (CD54) In Nonhuman Primates With Rental Allografts[1]", J. Immunol., 1990, 144, 4604.
Isobe et al., "Specific Acceptance of Cardiac Allograft After Treatment with Antibodies to ICAM–1 and LFA–1", Science, 1992, 255, 1125.
Staunton et al., "Primary Structure of ICAM–1 Demonstrates Interaction between Members of the Immunoglobulin and Integrin Supergene Families", Cell, 1988, 52, 925.
Stepkowski et al., "Blocking of Heart Allograft Rejection by Intercellular Adhesion Molecule–1 Antisense Oligonucleotides Alone or in Combination with Other Immunosuppressive Modalities[1]", J. Immunol. 1994, 153, 5336.

*Primary Examiner*—George C. Elliot
*Assistant Examiner*—Janet Epps
*Attorney, Agent, or Firm*—Law Offices of Jane Massey Licata

[57] ABSTRACT

The present invention provides compositions and methods for detecting and modulating levels of intercellular adhesion molecule-1 (ICAM-1) proteins, including human ICAM-1.

27 Claims, 1 Drawing Sheet

SEQUENCE LISTING (1) GENERAL INFORMATION:

(iii) NUMBER OF SEQUENCES: 33

(2) INFORMATION FOR SEQ ID NO: 1:

(i) SEQUENCE CHARACTERISTICS:
       (A) LENGTH: 2986 base pairs
       (B) TYPE: Nucleic Acid
       (C) STRANDEDNESS: Single
       (D) TOPOLOGY: Unknown (ii) MOLECULE TYPE: mRNA (iv) ANTI-SENSE: No (x) PUBLICATION INFORMATION:
       (A) AUTHORS: Staunton,D.E.
           Marlin,S.D.
           Stratowa,C.
           Dustin,M.L.
           Springer,T.A.
       (B) TITLE: Primary structure of ICAM-1
           demonstrates interaction between members of the
           immunoglobulin and integrin supergene families
       (C) JOURNAL: Cell
       (D) VOLUME: 52
       (E) ISSUE: 6
       (F) PAGES: 925-933
       (G) DATE: 25-MAR-1988

(xi) SEQUENCE DESCRIPTION: SEQ ID NO: 1:

```
GCGCCCCAGT CGACGCTGAG CTCCTCTGCT ACTCAGAGTT GCAACCTCAG          50
CCTCGCTATG GCTCCCAGCA GCCCCCGGCC CGCGCTGCCC GCACTCCTGG         100
TCCTGCTCGG GGCTCTGTTC CCAGGACCTG GCAATGCCCA GACATCTGTG         150
TCCCCCTCAA AAGTCATCCT GCCCCGGGGA GGCTCCGTGC TGGTGACATG         200
CAGCACCTCC TGTGACCAGC CCAAGTTGTT GGGCATAGAG ACCCCGTTGC         250
CTAAAAAGGA GTTGCTCCTG CCTGGGAACA ACCGGAAGGT GTATGAACTG         300
AGCAATGTGC AAGAAGATAG CCAACCAATG TGCTATTCAA ACTGCCCTGA         350
TGGGCAGTCA ACAGCTAAAA CCTTCCTCAC CGTGTACTGG ACTCCAGAAC         400
GGGTGGAACT GGCACCCCTC CCCTCTTGGC AGCCAGTGGG CAAGAACCTT         450
ACCCTACGCT GCCAGGTGGA GGGTGGGGCA CCCCGGGCCA ACCTCACCGT         500
GGTGCTGCTC CGTGGGGAGA AGGAGCTGAA ACGGGAGCCA GCTGTGGGGG         550
AGCCCGCTGA GGTCACGACC ACGGTGCTGG TGAGGAGAGA TCACCATGGA         600
GCCAATTTCT CGTGCCGCAC TGAACTGGAC CTGCGGCCCC AAGGGCTGGA         650
GCTGTTTGAG AACACCTCGG CCCCCTACCA GCTCCAGACC TTTGTCCTGC         700
CAGCGACTCC CCCACAACTT GTCAGCCCCC GGGTCCTAGA GGTGGACACG         750
CAGGGGACCG TGGTCTGTTC CCTGGACGGG CTGTTCCCAG TCTCGGAGGC         800
CCAGGTCCAC CTGGCACTGG GGACCAGAG GTTGAACCCC ACAGTCACCT          850
ATGGCAACGA CTCCTTCTCG GCCAAGGCCT CAGTCAGTGT GACCGCAGAG         900
GACGAGGGCA CCCAGCGGCT GACGTGTGCA GTAATACTGG GGAACCAGAG         950
CCAGGAGACA CTGCAGACAG TGACCATCTA CAGCTTTCCG GCGCCCAACG        1000
TGATTCTGAC GAAGCCAGAG GTCTCAGAAG GGACCGAGGT GACAGTGAAG        1050
```

```
TGTGAGGCCC ACCCTAGAGC CAAGGTGACG CTGAATGGGG TTCCAGCCCA      1100

GCCACTGGGC CCGAGGGCCC AGCTCCTGCT GAAGGCCACC CCAGAGGACA      1150

ACGGGCGCAG CTTCTCCTGC TCTGCAACCC TGGAGGTGGC CGGCCAGCTT      1200

ATACACAAGA ACCAGACCCG GGAGCTTCGT GTCCTGTATG GCCCCCGACT      1250

GGACGAGAGG GATTGTCCGG GAAACTGGAC GTGGCCAGAA AATTCCCAGC      1300

AGACTCCAAT GTGCCAGGCT TGGGGAACC CATTGCCCGA GCTCAAGTGT       1350

CTAAAGGATG GCACTTTCCC ACTGCCCATC GGGAATCAG TGACTGTCAC       1400

TCGAGATCTT GAGGGCACCT ACCTCTGTCG GGCCAGGAGC ACTCAAGGGG      1450

AGGTCACCCG CGAGGTGACC GTGAATGTGC TCTCCCCCCG GTATGAGATT      1500

GTCATCATCA CTGTGGTAGC AGCCGCAGTC ATAATGGGCA CTGCAGGCCT      1550

CAGCACGTAC CTCTATAACC GCCAGCGGAA GATCAAGAAA TACAGACTAC      1600

AACAGGCCCA AAAGGGACC CCCATGAAAC CGAACACACA AGCCACGCCT       1650

CCCTGAACCT ATCCCGGGAC AGGGCCTCTT CCTCGGCCTT CCCATATTGG      1700

TGGCAGTGGT GCCACACTGA ACAGAGTGGA AGACATATGC CATGCAGCTA      1750

CACCTACCGG CCCTGGGACG CCGGAGGACA GGGCATTGTC CTCAGTCAGA      1800

TACAACAGCA TTTGGGGCCA TGGTACCTGC ACACCTAAAA CACTAGGCCA      1850

CGCATCTGAT CTGTAGTCAC ATGACTAAGC CAAGAGGAAG GAGCAAGACT      1900

CAAGACATGA TTGATGGATG TTAAAGTCTA GCCTGATGAG AGGGGAAGTG      1950

GTGGGGAGA CATAGCCCCA CCATGAGGAC ATACAACTGG GAAATACTGA       2000

AACTTGCTGC CTATTGGGTA TGCTGAGGCC CACAGACTTA CAGAAGAAGT      2050

GGCCCTCCAT AGACATGTGT AGCATCAAAA CACAAAGGCC CACACTTCCT      2100

GACGGATGCC AGCTTGGGCA CTGCTGTCTA CTGACCCCAA CCCTTGATGA      2150

TATGTATTTA TTCATTTGTT ATTTTACCAG CTATTTATTG AGTGTCTTTT      2200

ATGTAGGCTA AATGAACATA GGTCTCTGGC CTCACGGAGC TCCCAGTCCA      2250

TGTCACATTC AAGGTCACCA GGTACAGTTG TACAGGTTGT ACACTGCAGG      2300

AGAGTGCCTG GCAAAAAGAT CAAATGGGGC TGGGACTTCT CATTGGCCAA      2350

CCTGCCTTTC CCCAGAAGGA GTGATTTTTC TATCGGCACA AAAGCACTAT      2400

ATGGACTGGT AATGGTTCAC AGGTTCAGAG ATTACCCAGT GAGGCCTTAT      2450

TCCTCCCTTC CCCCCAAAAC TGACACCTTT GTTAGCCACC TCCCCACCCA      2500

CATACATTTC TGCCAGTGTT CACAATGACA CTCAGCGGTC ATGTCTGGAC      2550

ATGAGTGCCC AGGGAATATG CCCAAGCTAT GCCTTGTCCT CTTGTCCTGT      2600

TTGCATTTCA CTGGGAGCTT GCACTATTGC AGCTCCAGTT TCCTGCAGTG      2650

ATCAGGGTCC TGCAAGCAGT GGGGAAGGGG GCCAAGGTAT TGGAGGACTC      2700

CCTCCCAGCT TTGGAAGGGT CATCCGCGTG TGTGTGTGTG TGTATGTGTA      2750

GACAAGCTCT CGCTCTGTCA CCCAGGCTGG AGTGCAGTGG TGCAATCATG      2800

GTTCACTGCA GTCTTGACCT TTTGGGCTCA AGTGATCCTC CCACCTCAGC      2850

CTCCTGAGTA GCTGGGACCA TAGGCTCACA ACACCACACC TGGCAAATTT      2900

GATTTTTTTT TTTTTTTCA GAGACGGGGT CTCGCAACAT TGCCCAGACT       2950

TCCTTTGTGT TAGTTAATAA AGCTTTCTCA ACTGCC                    2986
```

(2) INFORMATION FOR SEQ ID NO: 2:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 2:

GCCCAAGCTG GCATCCGTCA                                          20

(2) INFORMATION FOR SEQ ID NO: 3:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 3:

TCCCACAGCA GCTTGCACGA                                          20

(2) INFORMATION FOR SEQ ID NO: 4:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 4:

GACGCATCGC GCCTACATCG                                          20

(2) INFORMATION FOR SEQ ID NO: 5:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 5:

GTGCCCAAGC TGGCATCCGT                                          20

(2) INFORMATION FOR SEQ ID NO: 6:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 6:

AGCAGTGCCC AAGCTGGCAT                                          20

(2) INFORMATION FOR SEQ ID NO: 7:

(i) SEQUENCE CHARACTERISTICS:
        (A) LENGTH: 18 base pairs (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 7:

CCAAGCTGGC ATCCGTCA                                                  18

(2) INFORMATION FOR SEQ ID NO: 8:

(i) SEQUENCE CHARACTERISTICS:
            (A) LENGTH: 16 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 8:

AAGCTGGCAT CCGTCA                                                    16

(2) INFORMATION FOR SEQ ID NO: 9:

(i) SEQUENCE CHARACTERISTICS:
            (A) LENGTH: 14 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 9:

GCTGGCATCC GTCA                                                      14

(2) INFORMATION FOR SEQ ID NO: 10:

(i) SEQUENCE CHARACTERISTICS:
            (A) LENGTH: 12 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 10:

TGGCATCCGT CA                                                        12

(2) INFORMATION FOR SEQ ID NO: 11:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 11:

TCTGAGTAGC AGAGGAGCTC                                                20

(2) INFORMATION FOR SEQ ID NO: 12:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: No (xi) SEQUENCE DESCRIPTION: SEQ ID NO: 12:

GATCGCGTCG GACTATGAAG                                          20

(2) INFORMATION FOR SEQ ID NO: 13:

(i) SEQUENCE CHARACTERISTICS:
       (A) LENGTH: 2522 base pairs
       (B) TYPE: Nucleic Acid
       (C) STRANDEDNESS: Single
       (D) TOPOLOGY: Unknown (ii) MOLECULE TYPE: mRNA (iv) ANTI-SENSE: No (x) PUBLICATION INFORMATION:
       (A) AUTHORS: Ballantyne,C.M.
                    O'Brien,W.E.
                    Beaudet,A.L.
       (B) TITLE: Nucleotide sequence of the cDNA for
                  murine intercellular adhesion molecule-1 (ICAM-1)
       (C) JOURNAL: Nucleic Acids Res.
       (D) VOLUME: 17
       (E) ISSUE: 14
       (F) PAGES: 5853
       (G) DATE: 25-JUL-1989

(xi) SEQUENCE DESCRIPTION: SEQ ID NO: 13:

AGCACTCTGC CCTGGCCCTG CAATGGCTTC AACCCGTGCC AAGCCCACGC          50

TACCTCTGCT CCTGGCCCTG GTCACCGTTG TGATCCCTGG GCCTGGTGAT         100

GCTCAGGTAT CCATCCATCC AGAGAAGCC TTCCTGCCCC AGGGTGGGTC          150

CGTGCAGGTG AACTGTTCTT CCTCATGCAA GGAGGACCTC AGCCTGGGCT         200

TGGAGACTCA GTGGCTGAAA GATGAGCTCG AGAGTGGACC CAACTGGAAG         250

CTGTTTGAGC TGAGCGAGAT CGGGGAGGAC AGCAGTCCGC TGTGCTTTGA         300

GAACTGTGGC ACCGTGCAGT CGTCCGCTTC CGCTACCATC ACCGTGTATT         350

CGTTTCCGGA GAGTGTGGAG CTGAGACCTC TACCAGCCTG GCAGCAAGTA         400

GGCAAGGACC TCACCCTGCG CTGCCACGTG GATGGTGGAG CACCGCGGAC         450

CCAGCTCTCA GCAGTGCTGC TCCGTGGGGA GGAGATACTG AGCCGCCAGC         500

CAGTGGGTGG GCACCCCAAG GACCCCAAGG AGATCACATT CACGGTGCTG         550

GCTAGCAGAG GGGACCACGG AGCCAATTTC TCATGCCGCA CAGAACTGGA         600

TCTCAGGCCG CAAGGGCTGG CATTGTTCTC TAATGTCTCC GAGGCCAGGA         650

GCCTCCGGAC TTTCGATCTT CCAGCTACCA TCCCAAAGCT CGACACCCCT         700

GACCTCCTGG AGGTGGGCAC CCAGCAGAAG TTGTTTTGCT CCCTGGAAGG         750

CCTGTTTCCT GCCTCTGAAG CTCGGATATA CCTGGAGCTG GGAGGCCAGA         800

TGCCGACCCA GGAGAGCACA AACAGCAGTG ACTCTGTGTC AGCCACTGCC         850

TTGGTAGAGG TGACTGAGGA GTTCGACAGA ACCCTGCCGC TGCGCTGCGT         900

TTTGGAGCTA GCGGACCAGA TCCTGGAGAC GCAGAGGACC TTAACAGTCT         950

ACAACTTTTC AGCTCCGGTC CTGACCCTGA GCCAGCTGGA GGTCTCGGAA        1000

GGGAGCCAAG TAACTGTGAA GTGTGAAGCC CACAGTGGGT CGAAGGTGGT        1050

TCTTCTGAGC GGCGTCGAGC CTAGGCCACC CACCCCGCAG GTCCAATTCA        1100

CACTGAATGC CAGCTCGGAG GATCACAAAC GAAGCTTCTT TTGCTCTGCC        1150

-continued

| | |
|---|---|
| GCTCTGGAGG TGGCGGGAAA GTTCCTGTTT AAAAACCAGA CCCTGGAACT | 1200 |
| GCACGTGCTG TATGGTCCTC GGCTGGACGA GACGGACTGC TTGGGGAACT | 1250 |
| GGACCTGGCA AGAGGGGTCT CAGCAGACTC TGAAATGCCA GGCCTGGGGG | 1300 |
| AACCCATCTC CTAAAATGAC CTGCAGACGG AAGGCAGATG GTGCCCTGCT | 1350 |
| GCCCATCGGG GTGGTGAAGT CTGTCAAACA GGAGATGAAT GGTACATACG | 1400 |
| TGTGCCATGC CTTTAGCTCC CATGGGAATG TCACCAGGAA TGTGTACCTG | 1450 |
| ACAGTACTGT ACCACTCTCA AAATAACTGG ACTATAATCA TTCTGGTGCC | 1500 |
| AGTACTGCTG GTCATTGTGG GCCTCGTGAT GGCAGCCTCT TATGTTTATA | 1550 |
| ACCGCCAGAG AAAGATCAGG ATATACAAGT TACAGAAGGC TCAGGAGGAG | 1600 |
| GCCATAAAAC TCAAGGGACA AGCCCCACCT CCCTGAGCCT GCTGGATGAG | 1650 |
| ACTCCTGCCT GGACCCCCTG CAGGGCAACA GCTGCTGCTG CTTTTGAACA | 1700 |
| GAATGGTAGA CAGCATTTAC CCTCAGCCAC TTCCTCTGGC TGTCACAGAA | 1750 |
| CAGGATGGTG GCCTGGGGGA TGCACACTTG TAGCCTCAGA GCTAAGAGGA | 1800 |
| CTCGGTGGAT GGAGCAAGAC TGTGAACACG TGTGACCCGG ACCCACCTAC | 1850 |
| AGCCCGGTGG ACCTTCAGCC AAGAAACGCT GACTTCATTC TCTATTGCCC | 1900 |
| CTGCTGAGGG GCTCCTGCCT AAGGAAGACA TGATATCCAG TAGACACAAG | 1950 |
| CAAGAAGACC ACACTTCCCC CCCGACACAG GAAAGCTGAG ACATTGTCCC | 2000 |
| CAACTCTTCT TGATGTATTT ATTAATTTAG AGTTTTACCA GCTATTTATT | 2050 |
| GAGTACCCTG TATATAGTAG ATCAGTGAGG AGGTGAATGT ATAAGTTATG | 2100 |
| GCCTGGACCC TGCTGCAGAT GCTGTGAGAG TCTGGGGAAA GATCACATGG | 2150 |
| GTCGAGGGTT TCTCTACTGG TCAGGATGCT TTTCTCATAA GGGTCGACTT | 2200 |
| TTTTCACCAG TCACATAAAC ACTATGTGGA CTAGCAGTGA TTCTCTGCTC | 2250 |
| CTCCACATCC TGGAGCGTCC CAGCACCTCC CCACCTACTT TTGTTCCCAA | 2300 |
| TGTCAGCCAC CATGCCTTAG CAGCTGAACA ATCGAGCCTC ATGCTCATGA | 2350 |
| AATCATGGTC CCAGGCGGCT CCACCTCAAA GAGAAAGCCT GGAAGGAAAT | 2400 |
| GTTCCAACTC CTTAGAAGGG TCGTGCAAGC TGCTGTGGGA GGGTAAGCAC | 2450 |
| CCCTCCCAGC AGCAGAAACC TTTCCTTTGA ATCAATAAAG TTTTATGTCG | 2500 |
| GCCTGAAAAA AAAAAAAAA AA | 2522 |

(2) INFORMATION FOR SEQ ID NO: 14:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 14:

| | |
|---|---|
| TGCATCCCCC AGGCCACCAT | 20 |

(2) INFORMATION FOR SEQ ID NO: 15:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 15:

CCCCAGGCCA CCATCCTGTT                                                        20

(2) INFORMATION FOR SEQ ID NO: 16:

(i) SEQUENCE CHARACTERISTICS:
             (A) LENGTH: 20 base pairs
             (B) TYPE: Nucleic Acid
             (C) STRANDEDNESS: Single
             (D) TOPOLOGY: Linear (iv) ANTI-SENSE: No (xi) SEQUENCE DESCRIPTION:  SEQ ID NO: 16:

TCGCATCGAC CCGCCCACTA                                                        20

(2) INFORMATION FOR SEQ ID NO: 17:

(i) SEQUENCE CHARACTERISTICS:
             (A) LENGTH: 20 base pairs
             (B) TYPE: Nucleic Acid
             (C) STRANDEDNESS: Single
             (D) TOPOLOGY: Linear (iv) ANTI-SENSE: Yes (xi) SEQUENCE DESCRIPTION:  SEQ ID NO: 17:

CCAGGCCACC ATCCTGTTCT                                                        20

(2) INFORMATION FOR SEQ ID NO: 18:

(i) SEQUENCE CHARACTERISTICS:
             (A) LENGTH: 20 base pairs
             (B) TYPE: Nucleic Acid
             (C) STRANDEDNESS: Single
             (D) TOPOLOGY: Linear (iv) ANTI-SENSE: Yes (xi) SEQUENCE DESCRIPTION:  SEQ ID NO: 18:

AGGCTACAAG TGTGCATCCC                                                        20

(2) INFORMATION FOR SEQ ID NO: 19:

(i) SEQUENCE CHARACTERISTICS:
             (A) LENGTH: 838 base pairs
             (B) TYPE: Nucleic Acid
             (C) STRANDEDNESS: Single
             (D) TOPOLOGY: Unknown (ii) MOLECULE TYPE: mRNA (iv) ANTI-SENSE: No (x) PUBLICATION INFORMATION:
             (A) AUTHORS: Ballantyne,C.M.
                   Sligh,J.E.
                   Dai,X.Y.
                   Beaudet,A.L.
             (B) TITLE: Characterization of the murine ICAM-1
                   gene
             (C) JOURNAL: Genomics
             (D) VOLUME: 14
             (E) ISSUE: 4
             (F) PAGES: 1076-1080
             (G) DATE: DEC-1992

(xi) SEQUENCE DESCRIPTION:  SEQ ID NO: 19:

```
AAGGGAAGTG AGGACTGCCT CTCAGGCAGG ACTTTCTCAC AGCGGATCTG          50

TCCGGGCCTG CTTGGATCGC TGCTTCATCT CTAGTGCCAA GTGGGTGGAG         100

CATGGTCCTG GGGAGAGGGG CACCTCTGAA TGGATGGCGT CCCCTAACGA         150

TTCCAGGGAG CCCTTATCCC CGGCAAGGGC ATGTCTGGTG GGTTAAAGAG         200

GCTTGCAGTA GTTGGGGAAA TCAGGACTTG ATTTCGGATC CTCGAGGATC         250

CCTGCGAAAT GCCGAGCCTC AGTTTATCCC TTTGAGGGGA TGGCGGTCCT         300

GATGTCGCAG GGGACTAGGC AGTAGTCAAT CAGTTAACCA GGAGGCGTGA         350

CTCCTGGAGG CCCGGGGCTT CTCTCCGGAC TCACCTGCTG GTCTCTGACA         400

CCACCTCCCC CCACATGTCA TTACTTCAGT TTGGAAATTC CTAGATCGCA         450

GGGGCCAGCG AGGCAGGACC ACCCCTCTCT GCCAGGGCAC AGTCTCCACC         500

CGGAAATACC GAAGCCCTCG TTCCGGAGGG AAGGCGCGA GGTTTCCCGG          550

AAAGTGGCCC CGACAGCACC GCCCCTCGGC CCCCCGTGAG CCAGAGACTA         600

TAAAAGCGCC GCCCGCCTCA GTCTGCACCC AGTGCTAGTG CTGAGCTCCG         650

CTGCTACCTG CACTTTGCCC TGGCCCTGCA ATGGCTTCAA CCCGTGCCAA         700

GCCCACGCTA CCTCTGCTCC TGGCCCTGGT CACCGTTGTG ATCCCTGGTG         750

AGTCCGAGGT GGGGTCGCTT TGGGGGGCAG GTCTCCAAAC TCCAGGACCC         800

AGAGCGCGTC GAAATCCTGC TTCCGGCCAG CGAACATA                      838
```

(2) INFORMATION FOR SEQ ID NO: 20:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 20:

```
TGCAGGTAGC AGCGGAGCTC                                           20
```

(2) INFORMATION FOR SEQ ID NO: 21:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 21:

```
GAAGCCATTG CAGGGCCAGG                                           20
```

(2) INFORMATION FOR SEQ ID NO: 22:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 22:

```
GGAGCTCAGC ACTAGCACTG                                           20
```

(2) INFORMATION FOR SEQ ID NO: 23:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 23:

GCCAGGGCAA AGTGCAGGTA                                          20

(2) INFORMATION FOR SEQ ID NO: 24:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 24:

GCGCTTTTAT AGTCTCTGGC                                          20

(2) INFORMATION FOR SEQ ID NO: 25:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 25:

GGTGCAGACT GAGGCGGGCG                                          20

(2) INFORMATION FOR SEQ ID NO: 26:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 26:

ATCCCGACTG ACAGACGTCC                                          20

(2) INFORMATION FOR SEQ ID NO: 27:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 27:

TTCCCCAGCA GCATGCACGA                                          20

(2) INFORMATION FOR SEQ ID NO: 28:

```
    (i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 28:

TCCGACAGCA CCTTGCACGA                                                  20

(2) INFORMATION FOR SEQ ID NO: 29:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 29:

TCCCTCAGCA GCTTGCACGA                                                  20

(2) INFORMATION FOR SEQ ID NO: 30:

(i) SEQUENCE CHARACTERISTICS:
        (A) LENGTH: 42 base pairs
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 30:

AATACCGGAT CCGGAATTCC GGGTGCAGGT AGCAGCGGAG CT                         42

(2) INFORMATION FOR SEQ ID NO: 31:

(i) SEQUENCE CHARACTERISTICS:
        (A) LENGTH: 37 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 31:

TTCGCTCTAG ACAGGAAGAC ATAAAAACTT TATTGAT                               37

(2) INFORMATION FOR SEQ ID NO: 32:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 32:

TGCCTGTGAA GATGGTCGCG G                                                21

(2) INFORMATION FOR SEQ ID NO: 33:

(i) SEQUENCE CHARACTERISTICS:
        (A) LENGTH: 21 base pairs
        (B) TYPE: Nucleic Acid
        (C) STRANDEDNESS: Single
```

-continued

```
        (D) TOPOLOGY: Linear (iv) ANTI-SENSE: YES (xi) SEQUENCE DESCRIPTION:  SEQ ID NO: 33:

ACCATGTCTC CTGTCTTTGC T                                              21
```

ENHANCED ANTISENSE MODULATION OF ICAM-1

CROSS-REFERENCES TO RELATED APPLICATIONS

This application is a continuation-in-part of application Ser. No. 08/440,740 (filed May 12, 1995, now U.S. Pat. No. 5,843,738), which is a continuation-in-part of application Ser. No. 08/063,167 (filed May 17, 1993, now U.S. Pat. No. 5,514,788) which is a continuation of application Ser. No. 07/969,151 (filed Feb. 10, 1993, now abandoned), which is a continuation-in-part of application Ser. No. 08/007,997 (filed Jan. 21, 1993, now U.S. Pat. No. 5,591,623), which is a continuation-in-part of application Ser. No. 07/939,855 (filed Sep. 2, 1992, now abandoned), which is a continuation-in-part of application Ser. No. 07/567,286 (filed Aug. 14, 1990, now abandoned).

FIELD OF THE INVENTION

The present invention provides compositions and methods for detecting and modulating levels of intercellular adhesion molecule-1 (ICAM-1) proteins, including human ICAM-1 (also known as CD54). In particular, the invention relates to antisense compounds specifically hybridizable with nucleic acids encoding ICAM-1 proteins that can modulate the expression of such ICAM-1 proteins. Intercellular adhesion molecules are proteins which are expressed on the surfaces of a variety of cell types and which mediate cell:cell interactions and subsequent cellular and biological responses, including, but not limited to, T cell activation, leukocyte transmigration and inflammation. Accordingly, modulation of the expression of ICAM-1 by one or more antisense compounds of the invention allows for the control of cell:cell interactions and resulting effects such as, e.g., inflammation. The invention is thus directed to diagnostic methods for detecting, and prophylactic, palliative and therapeutic methods for preventing and treating, conditions associated with ICAM-1-mediated processes or with abnormal expression of ICAM-1 proteins.

BACKGROUND OF THE INVENTION

Cell:cell interactions are mediated by a variety of cell surface proteins including intercellular adhesion molecule-1 (ICAM-1). ICAM-1-mediated events, whether mediated directly or indirectly, include such biological significant processes as leukocyte transmigration, T cell activation and inflammatory injury (for reviews, see Bierer et al., *FASEB J.*, 1988, 2, 2584; Makgoba et al., *Immunol. Today*, 1989, 10, 417; Dustin et al., *Annu. Rev. Immunol.*, 1991, 9, 27; and Albelda et al., *FASEB J.*, 1994, 8, 504).

The adhesion of white blood cells to vascular endothelium and other cell types is mediated by interactions between specific proteins, termed "adhesion molecules," located on the plasma membrane of both white blood cells and vascular endothelium. The interaction between adhesion molecules is similar to classical receptor ligand interactions with the exception that the ligand is fixed to the surface of a cell instead of being soluble. The identification of patients with a genetic defect in leukocyte adhesion has enabled investigators to identify a family of proteins responsible for adherence of white blood cells. Leukocyte adhesion deficiency (LAD) is a rare autosomal trait characterized by recurrent bacterial infections and impaired pus formation and wound healing. The defect was shown to occur in the common B-subunit of three heterodimeric glycoproteins, Mac-1, LFA-1, and p150,95, normally expressed on the outer cell membrane of white blood cells (Anderson et al., *Ann. Rev. Med.*, 1987, 38, 175). Patients suffering from LAD exhibit a defect in a wide spectrum of adherence-dependent functions of granulocytes, monocytes, and lymphocytes. Three ligands for LFA-1 have been identified, intercellular adhesion molecules 1, 2 and 3 (ICAM-1, ICAM-2 and ICAM-3). Mac-1 and p150,95 both bind complement fragment C3bi and, perhaps, other unidentified ligands; Mac-1 also binds ICAM-1.

Expression of ICAM-1 has been associated with a variety of inflammatory skin disorders such as allergic contact dermatitis, fixed drug eruption, lichen planus and psoriasis (Ho et al., *J. Am. Acad. Dermatol.*, 1990, 22, 64; Griffiths et al., *Am. J. Pathology*, 1989, 135, 1045; Lisby et al., *Br. J. Dermatol.*, 1989, 120, 479; Shiohara et al., *Arch. Dermatol.*, 1989, 125, 1371). In addition, ICAM-1 expression has been detected in the synovium of patients with rheumatoid arthritis (Hale et al., *Arth. Rheum.*, 1989, 32, 22), in pancreatic B-cells in diabetes (Campbell et al., *Proc. Natl. Acad. Sci. U.S.A.*, 1989, 86, 4282) and in thyroid follicular cells in patients with Graves' disease (Weetman et al., *J. Endocrinol.*, 1989, 122, 185), and has been associated with renal and liver allograft rejection (Faull et al., *Transplantation*, 1989, 48, 226; Adams et al., *Lancet*, 1989, 1122).

It is has been hoped that inhibitors of ICAM-1 would provide a novel therapeutic class of anti-inflammatory agents with activity towards a variety of inflammatory diseases or diseases with an inflammatory component such as asthma, rheumatoid arthritis, allograft rejections, inflammatory bowel disease, various dermatological conditions, and psoriasis. In addition, inhibitors of ICAM-1 may also be effective in the treatment of colds due to rhinovirus infection, AIDS, Kaposi's sarcoma and some cancers and their metastasis. The use of neutralizing monoclonal antibodies against ICAM-1 in animal models has provided evidence that inhibitors of ICAM-1, if identified, would have potential therapeutic benefit for asthma (Wegner et al., *Science*, 1990, 247, 456), renal allografts (Cosimi et al., *J. Immunol.*, 1990, 144, 4604) and cardiac allografts (Isobe et al., *Science*, 1992, 255, 1125). Moreover, a soluble form of ICAM-1 molecule was effectively used to prevent rhinovirus infection of cells in culture (Marlin et al., *Nature*, 1990, 344, 70).

There remains a need for therapeutic agents with an enhanced ability to effectively prevent the expression of ICAM-1. Current agents which affect cellular adhesion molecules include monoclonal antibodies and polypeptide soluble forms of the ligands of adhesion molecules. Monoclonal antibodies to ICAM-1 may prove to be useful for the treatment of acute inflammatory response due to expression of ICAM-1, however, with chronic treatment, the host animal can develop an immune response against the anti-ICAM-1 antibodies, thereby limiting their usefulness. In addition, antibodies are large proteins which may have difficulty in gaining access to the inflammatory site. Polypeptide forms of the cell adhesion molecules suffer from many of the same limitations as antibodies in addition to the expense of their production and their low binding affinity. Antisense compounds avoid many of the pitfalls of other agents that could potentially be used to block the effects of ICAM-1. The present invention is drawn to chemically modified antisense oligonucleotides having an enhanced ability to modulate ICAM-1.

SUMMARY OF THE INVENTION

In accordance with the present invention, antisense compounds are provided which specifically hybridize with a nucleic acid encoding an ICAM-1 protein. Certain antisense compounds of the invention are designed to bind either directly to mRNA transcribed from, or to a selected DNA portion of, a gene that encodes an ICAM-1 protein, thereby modulating the expression thereof. In particular embodiments of the invention, the ICAM-1 protein, and the gene encoding it, are those of a mammal including a human. Pharmaceutical compositions comprising the antisense compounds of the invention, and various methods of using the antisense compounds of the invention, are also herein provided.

DETAILED DESCRIPTION OF THE INVENTION

Figure 1:
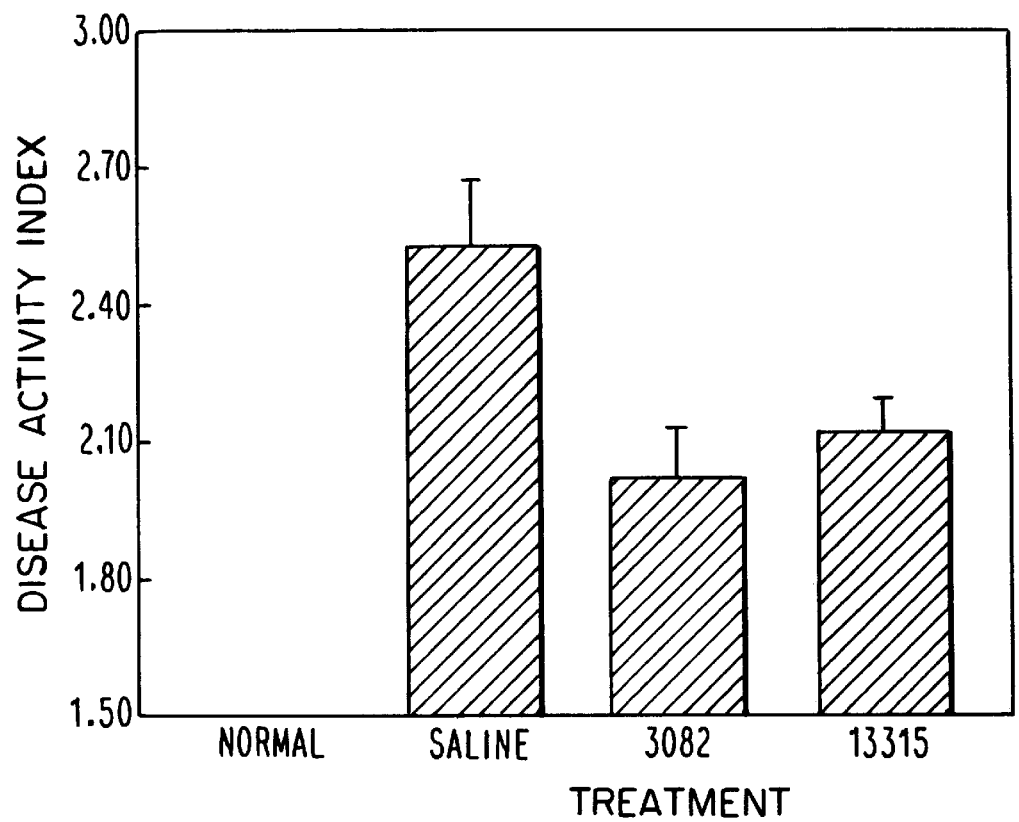
FIG. 1 shows the prevention of dextran sulfate sodium-induced colitis by ICAM-1 antisense compounds.

Oligonucleotides, and other compounds such as peptide nucleic acids (PNAs), may comprise nucleotide sequences sufficient in identity and number to effect specific hybridization with the "sense" strand of a particular (targeted) nucleic acid; such oligonucleotides are commonly described as "antisense." "Antisense compounds," as defined herein, refers to compounds that effect such specific hybridization in living cells, thereby modulating the expression of the targeted nucleic acid. Antisense compounds, particularly antisense oligonucleotides, are commonly used as research reagents, diagnostic aids and therapeutic agents. It has been discovered that nucleic acids encoding intercellular adhesion molecule-1 (ICAM-1; also known as CD54 antigen) proteins, including human ICAM-1, are particularly amenable to the antisense approach for therapeutic uses. The present invention is drawn to chemically modified antisense compounds, including oligonucleotides, having an enhanced ability to modulate the expression of ICAM-1.

Methods of modulating the expression of ICAM-1 proteins with antisense compounds are provided herein and are believed to be useful therapeutically as a consequence of the association between ICAM-1 expression and certain hyperproliferative or inflammatory disorders and/or diseases resulting from infection by one or more pathogens. These methods are also useful as diagnostic or research tools, for example, in the detection and determination of the role of ICAM-1 in various cell functions and physiological processes and conditions, and for the diagnosis of conditions associated with such expression and activation.

As a consequence of the association between ICAM-1 and normal and abnormal cell-cell interactions, inhibition of the expression of ICAM-1 is expected to potentially lead to, for example, the inhibition of a variety of pathogenic, inflammatory events, tumorigenic and/or metastatic events and, accordingly, results in modulation of the undesirable consequences of such events. Such modulation is desirable for treating (i.e., providing prophylactic, palliative and/or therapeutic effects) various pathogenic, inflammatory and hyperproliferative disorders or diseases. Such inhibition of ICAM-1 is further desirable for preventing or modulating the development of such diseases or disorders in an animal suspected of being, or known to be, prone to such diseases or disorders.

The present invention also comprises methods of inhibiting a variety of ICAM-1-mediated pathogenic, inflammatory and tumorigenic and/or metastatic events using the antisense compounds of the invention. Methods of treating conditions in which abnormal or excessive ICAM-1 expression and/or ICAM-1-mediated inflammation occurs are also provided. These methods employ the antisense compounds of the invention and are believed to be useful therapeutically and as clinical research and diagnostic tools. The antisense compounds of the present invention may also be used for research purposes. Thus, for example, the specific hybridization exhibited by the antisense oligonucleotides of the present invention may be used for assays, purifications, cellular product preparations and in other methodologies which may be appreciated by persons of ordinary skill in the art.

The present invention employs antisense compounds which modulate the function of DNA or messenger RNA (mRNA) encoding a protein (ICAM-1) the modulation of which is desired and ultimately regulates the expression of the protein. Hybridization of an antisense compound to its mRNA target interferes with the normal role of mRNA and causes a modulation of its function in cells. The functions of mRNA to be interfered with include all vital functions such as translocation of the RNA to the site for protein translation; translation of protein from the RNA; splicing of the RNA to yield one or more mRNA species; and structure or catalytic activity which may be provided by the RNA. In general, the overall effect of such interference with function is modulation of the cellular amount and/or activity (including expression) of an RNA, wherein "modulation" means either an increase (stimulation) or a decrease (inhibition) in the amount and/or activity of the RNA. In the context of the present invention, inhibition is the preferred form of modulation. In the case of mRNA, the overall effect of such interference with function is modulation of the expression of one or more polypeptides encoded by the mRNA.

It is preferred to target specific genes for antisense attack. "Targeting" an oligonucleotide to the associated nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a foreign nucleic acid from an infectious agent. In the present invention, the target is a cellular gene associated with inflammatory and hyperproliferative disorders. The targeting process also includes determination of a site or sites within this gene for the oligonucleotide interaction to occur such that the desired effect, either detection or modulation of expression of the protein, will result. Once the target site or sites have been identified, oligonucleotides are chosen which are sufficiently complementary to the target, i.e., hybridize sufficiently well and with sufficient specificity to give the desired effect.

Generally, there are several regions of a fully processed mRNA that may be targeted for antisense modulation: the 5' "cap," which comprises an N7-methylated guanosine residue joined to the most 5' residue of the mRNA via a triphosphate linkage (Baker, Chapter 3 In: Antisense Research and Applications, Crooke et al., eds., CRC Press, Boca Raton, Fla., 1993, pages 37–53); the 5' untranslated region (hereinafter, the "5'-UTR"), the translation initiation codon region (hereinafter, the "AUG" region), the open reading frame (hereinafter, the "ORF") or "coding region," the translation termination codon region (hereinafter, the "stop codon" region or simply "stop" for short) and the 3' untranslated region (hereinafter, the "3'-UTR"). As is known in the art, these regions are arranged in a typical messenger RNA molecule in the following order (left to right, 5' to 3'): cap, 5'-UTR, AUG, ORF, stop codon, 3'-UTR.

As is known in the art, although some eukaryotic transcripts are directly translated, many ORFs contain one or more sequences, known as "introns," which are excised from a transcript before it is translated; the expressed (unexcised) portions of the ORF are referred to as "exons" (Alberts et al., *Molecular Biology of the Cell,* 1983, Garland Publishing Inc., New York, pp. 411–415). In some instances, an ORF contains one or more sites that may be targeted due to some functional significance in vivo. Examples of the latter types of sites include intragenic stem-loop structures (see, e.g., U.S. Pat. No. 5,512,438) and, in unprocessed mRNA molecules, intron/exon splice sites.

Within the context of the present invention, one preferred intragenic site is the region encompassing the translation initiation codon of the open reading frame (ORF) of the gene. Because, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Furthermore, 5'-UUU functions as a translation initiation codon in vitro (Brigstock et al., *Growth Factors,* 1990, 4, 45; Gelbert et al., *Somat. Cell. Mol. Genet.,* 1990, 16, 173; Gold and Stormo, in: *Escherichia coli* and *Salmonella typhimurium: Cellular and Molecular Biology,* Vol. 2, 1987, Neidhardt et al., eds., American Society for Microbiology, Washington, D.C., p. 1303). Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions, in order to generate related polypeptides having different amino terminal sequences. In the context of the invention, "start codon" and "translation initiation codon" refer to the codon or codons that are used in vivo to initiate translation of an mRNA molecule transcribed from a gene encoding an ICAM-1 protein, regardless of the nucleotide sequence(s) of such codons.

Within the context of the present invention, another preferred intragenic site is the region encompassing the translation initiation codon of the open reading frame (ORF) of the gene. It is known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

As used herein, the terms "start codon region" and "translation initiation region" refer to a portion of such an mRNA or gene that encompasses about 50 contiguous (adjacent) nucleotides in either direction (i.e., 5' or 3') from a translation initiation codon. Similarly, the terms "stop codon region" and "translation termination region" refer to a portion of such an mRNA or gene that encompasses about 50 contiguous (adjacent) nucleotides in either direction (i.e., 5' or 3') from a translation termination codon.

Other preferred intragenic sites within the context of the present invention include the open reading frame (ORF) of the gene, the 5'-untranslated region (5'-UTR) and the 3'-untranslated region (3'-UTR). Because many eukaryotic ORFs are a thousand nucleotides or more in length, it is often convenient to subdivide the ORF into, e.g., the 5' ORF region, the central ORF region, and the 3' ORF region. The 5'-UTR is the region 5' from the start codon region, and, similarly, the 3'-UTR is the region 3' from the stop codon region. The 5' cap, a specialized structure that at least partially mediates ribosome binding, may also be targeted for antisense compounds; see Baker, Chapter 3 in: *Antisense Research and Applications,* Crooke and Lebleu, eds., CRC Press, Boca Raton, 1993, pages 37–53, and U.S. Pat. No. 5,643,780, hereby incorporated by reference.

The remainder of the Detailed Description relates in more detail the (1) Antisense Compounds of the Invention and (2) Bioequivalents and (3) Exemplary Utilities thereof, as well as (4) Pharmaceutical Compositions comprising the Antisense Compounds of the Invention and (5) Methods of Administration thereof.

1. Antisense Compounds of the Invention: The present invention employs antisense compounds that modulate ICAM-1 proteins. The term "antisense compounds" (a) specifically includes synthetic oligonucleotides, as well as peptide nucleic acids (PNAs), having a nucleobase sequence specifically hybridizable with a nucleic acid encoding an ICAM-1 protein and (b) specifically excludes ribozymes and nucleic acids of biological origin. In the context of this invention, the term "oligonucleotidel" refers to an oligomer or polymer of ribonucleic acid (RNA) or deoxyribonucleic acid (DNA) or mimetics thereof. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. The antisense compounds of the invention are synthesized in vitro and do not include antisense compositions of biological origin, or genetic vector constructs designed to direct the in vivo synthesis of antisense molecules.

The antisense compounds in accordance with this invention preferably comprise from about 8 to about 30 nucleobases, more preferably from about 12 to about 28 and most preferably from about 15 to about 26 nucleobases. Particularly preferred antisense compounds are antisense oligonucleotides. A discussion of antisense oligonucleotides and some desirable modifications can be found in De Mesmaeker et al., *Acc. Chem. Res.,* 1995, 28, 366.

An oligonucleotide is a polymer of a repeating unit generically known as a nucleotide. An unmodified (naturally occurring) nucleotide has three components: (1) a nitrogen-containing heterocyclic base linked by one of its nitrogen atoms to (2) a 5-pentofuranosyl sugar and (3) a phosphate esterified to one of the 5' or 3' carbon atoms of the sugar. When incorporated into an oligonucleotide chain, the phosphate of a first nucleotide is also esterified to an adjacent sugar of a second, adjacent nucleotide via a 3'–5' phosphate linkage.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be further joined to form a circular structure, however, within the context of the invention, open linear structures are generally preferred.

Within the oligonucleotide structure, the phosphate groups are commonly referred to as forming the intersugar "backbone" of the oligonucleotide. The normal linkage or backbone of RNA and DNA is a 3' to 5' phosphodiester linkage. The backbone of an oligonucleotide (or other antisense compound) positions a series of bases in a specific order; the written representation of this ordered series of bases, usually written in 5' to 3' order unless otherwise indicated, is known as a nucleotide or nucleobase sequence.

Oligonucleotides may comprise nucleotide sequences sufficient in identity and number to effect specific hybridization with a particular nucleic acid. Such oligonucleotides which specifically hybridize to a portion of the sense strand of a gene are commonly described as "antisense." In the context of the invention, "hybridization" means hydrogen bonding, which may be Watson-Crick, Hoogsteen or reversed Hoogsteen hydrogen bonding, between complementary nucleotides. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other.

"Specifically hybridizable" and "complementary" are thus terms which are used to indicate a sufficient degree of complementarity or precise pairing such that stable and specific binding occurs between the oligonucleotide and the DNA or RNA target. An oligonucleotide is specifically hybridizable to its target sequence due to the formation of base pairs between specific partner nucleobases in the interior of a nucleic acid duplex. Among the naturally occurring nucleobases, guanine (G) binds to cytosine (C), and adenine (A) binds to thymine (T) or uracil (U). In addition to the equivalency of U (RNA) and T (DNA) as partners for A, other naturally occurring nucleobase equivalents are known, including 5-methylcytosine and 5-hydroxymethylcytosine (HMC) (C equivalents), and 5-hydroxymethyluracil (U equivalent). Furthermore, synthetic nucleobases which retain partner specificity are known in the art and include, for example, 7-deaza-Guanine, which retains partner specificity for C. Thus, an oligonucleotide's capacity to specifically hybridize with its target sequence will not be altered by a chemical modification to a nucleobase in the nucleotide sequence of the oligonucleotide which does not impact its specificity for a partner nucleobase in the target nucleic acid.

It is understood in the art that the nucleobase sequence of an oligonucleotide or other antisense compound need not be 100% complementary to its target nucleic acid sequence to be specifically hybridizable. An antisense compound is specifically hybridizable to its target nucleic acid when there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under assay conditions.

Antisense oligonucleotides are commonly used as research reagents, diagnostic aids, and therapeutic agents. For example, antisense oligonucleotides, which are able to inhibit gene expression with exquisite specificity, are often used by those of ordinary skill to elucidate the function of particular genes, for example to distinguish between the functions of various members of a biological pathway. This specific inhibitory effect has, therefore, been harnessed by those skilled in the art for research uses. The specificity and sensitivity of oligonucleotides is also harnessed by those of skill in the art for therapeutic uses. Specific examples of preferred antisense compounds useful in this invention include oligonucleotides containing modified backbones or non-natural intersugar linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their intersugar backbone can also be considered to be oligonucleosides.

Specific oligonucleotide chemical modifications are described in the following subsections. It is not necessary for all positions in a given compound to be uniformly modified, and in fact more than one of the following modifications may be incorporated in a single antisense compound or even in a single residue thereof, for example, at a single nucleoside within an oligonucleotide.

A. Modified Linkages: Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalklyphosphotriesters, and boranophosphates having normal 3'–5' linkages, 2'–5' linked analogs of these, and those having inverted polarity wherein the adjacent pairs of nucleoside units are linked 3'–5' to 5'–3' or 2'–5' to 5'–2'. Various salts, mixed salts and free acid forms are also included.

Representative United States Patents that teach the preparation of the above phosphorus atom containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, certain of which are commonly owned with this application, and each of which is herein incorporated by reference.

Preferred modified oligonucleotide backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application, and each of which is herein incorporated by reference.

In other preferred oligonucleotide mimetics, both the sugar and the intersugar linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

B. Modified Nucleobases: The compounds of the invention may additionally or alternatively comprise nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering,* pages 858–859, Kroschwitz, J. I., ed. John Wiley & Sons, 1990, those disclosed by Englisch et al., *Angewandte Chemie, International Edition,* 1991, 30, 613, and those disclosed by Sanghvi, Y. S., Chapter 15, *Antisense Research and Applications,* pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Id., pages 276–278) and are presently preferred base substitutions, even more particularly when combined with 2'-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, certain of which are commonly owned, and each of which is herein incorporated by reference, and commonly owned U.S. patent application Ser. No. 08/762,488, filed on Dec. 10, 1996, also herein incorporated by reference.

C. Sugar Modifications: The antisense compounds of the invention may additionally or alternatively comprise one or more substituted sugar moieties. Preferred oligonucleotides comprise one of the following at the 2' position: OH; F; O—, S—, or N-alkyl, O—, S—, or N-alkenyl, or O, S— or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy [2'—O—$CH_2CH_2OCH_3$, also known as 2'—O—(2-methoxyethyl) or 2'-MOE] (Martin et al., *Helv. Chim. Acta,* 1995, 78, 486), i.e., an alkoxyalkoxy group. A further preferred modification includes 2'-dimethylaminooxyethoxy, i.e., a $O(CH_2)_2ON(CH_3)_2$ group, also known as 2'-DMAOE, as described in co-owned U.S. patent application Ser. No. 09/016,520, filed on Jan. 30, 1998, the contents of which are herein incorporated by reference.

Other preferred modifications include 2'-methoxy (2'—O—$CH_3$), 2'-aminopropoxy (2'—$OCH_2CH_2CH_2NH_2$) and 2'-fluoro (2'—F). Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, certain of which are commonly owned, and each of which is herein incorporated by reference, and commonly owned U.S. patent application Ser. No. 08/468,037, filed on Jun. 5, 1995, also herein incorporated by reference.

D. Other Modifications: Additional modifications may also be made at other positions on the oligonucleotide, particularly the 3' position of the sugar on the 3' terminal nucleotide and the 5' position of 5' terminal nucleotide. For example, one additional modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA,* 1989, 86, 6553), cholic acid (Manoharan et al., *Bioorg. Med. Chem. Lett.,* 1994, 4, 1053), a thioether, e.g., hexyl-S-tritylthiol (Manoharan et al., *Ann. N.Y. Acad. Sci.,* 1992, 660, 306; Manoharan et al., *Bioorg. Med. Chem. Let.,* 1993, 3, 2765), a thiocholesterol (Oberhauser et al., *Nucl. Acids Res.,* 1992, 20, 533), an aliphatic chain, e.g., dodecandiol or undecyl residues (Saison-Behmoaras et al., *EMBO J.,* 1991, 10, 111; Kabanov et al., *FEBS Lett.,* 1990, 259, 327; Svinarchuk et al., *Biochimie,* 1993, 75, 49), a phospholipid, e.g., di-hexadecyl-rac-glycerol or triethylammonium 1,2-di-o-hexadecyl-rac-glycero-3-H-phosphonate (Manoharan et al., *Tetrahedron Lett.,* 1995, 36, 3651; Shea et al., *Nucl. Acids Res.,* 1990, 18, 3777), a polyamine or a polyethylene glycol chain (Manoharan et al., *Nucleosides & Nucleotides,* 1995, 14, 969), or adamantane acetic acid (Manoharan et al., *Tetrahedron Lett.,* 1995, 36, 3651), a palmityl moiety (Mishra et al., *Biochim. Biophys. Acta,* 1995, 1264, 229), or an octadecylamine or hexylamino-carbonyloxycholesterol moiety (Crooke et al., *J. Pharmacol. Exp. Ther.,* 1996, 277, 923).

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned, and each of which is herein incorporated by reference.

E. Chimeric Oligonucleotides: The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate oligodeoxynucleotides hybridizing to the same target region. Cleavage of the RNA target can be routinely detected by gel electrophoresis and, if necessary, associated nucleic acid hybridization techniques known in the art. RNase H-mediated target cleavage is distinct from the use of ribozymes to cleave nucleic acids, and ribozymes are not comprehended by the present invention.

By way of example, such "chimeras" may be "gapmers," i.e., oligonucleotides in which a central portion (the "gap") of the oligonucleotide serves as a substrate for, e.g., RNase H, and the 5' and 3' portions (the "wings") are modified in such a fashion so as to have greater affinity for, or stability when duplexed with, the target RNA molecule but are unable to support nuclease activity (e.g., 2'-fluoro- or 2'-methoxyethoxy-substituted). Other chimeras include "hemimers," that is, oligonucleotides in which the 5' portion of the oligonucleotide serves as a substrate for, e.g., RNase H, whereas the 3' portion is modified in such a fashion so as to have greater affinity for, or stability when duplexed with, the target RNA molecule but is unable to support nuclease activity (e.g., 2'-fluoro- or 2'-methoxyethoxy-substituted), or vice-versa.

A number of chemical modifications to oligonucleotides that confer greater oligonucleotide:RNA duplex stability have been described by Freier et al. (*Nucl. Acids Res.,* 1997, 25, 4429). Such modifications are preferred for the RNase H-refractory portions of chimeric oligonucleotides and may generally be used to enhance the affinity of an antisense compound for a target RNA.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned, and each of which is herein incorporated by reference, and commonly owned and allowed U.S. patent application Ser. No. 08/465,880, filed on Jun. 6, 1995, also herein incorporated by reference.

F. Synthesis: The oligonucleotides used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides such as the phosphorothioates and alkylated derivatives.

1. Teachings regarding the synthesis of particular modified oligonucleotides may be found in the following U.S.

patents or pending patent applications, each of which is commonly assigned with this application: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, issued Jun. 29, 1993, and U.S. Pat. No. 5,608,046, both drawn to conjugated 4'-desmethyl nucleoside analogs; U.S. Pat. Nos. 5,602,240, and 5,610,289, drawn to backbone modified oligonucleotide analogs; and U.S. patent application Ser. No. 08/383,666, filed Feb. 3, 1995, and U.S. Pat. No. 5,459,255, drawn to, inter alia, methods of synthesizing 2'-fluoro-oligonucleotides.

2. Bioequivalents: The compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to "prodrugs" and "pharmaceutically acceptable salts" of the antisense compounds of the invention, pharmaceutically acceptable salts of such prodrugs, and other bioequivalents.

A. Oligonucleotide Prodrugs:

The antisense compounds of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the antisense compounds of the invention are prepared as SATE [(S-acetyl-2-thioethyl) phosphate] derivatives according to the methods disclosed in WO 93/24510 to Gosselin et al., published Dec. 9, 1993.

B. Pharmaceutically Acceptable Salts: The term "pharmaceutically acceptable salts" refers to physiologically and pharmaceutically acceptable salts of the antisense compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are chloroprocaine, choline, N,N'-dibenzylethylenediamine, diethanolamine, dicyclohexylamine, ethylenediamine, N-methylglucamine, and procaine (see, for example, Berge et al., "Pharmaceutical Salts," *J. of Pharma Sci.*, 1977, 66:1). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, embonic acid, 4-aminosalicylic acid, 2-phenoxybenzoic acid, nicotinic acid, isonicotinic acid or 2-acetoxybenzoic acid; and with amino acids, such as the 20 alpha-amino acids involved in the synthesis of proteins in nature, for example glutamic acid or aspartic acid, and also with naphthalene-1,5-disulfonic acid, phenylacetic acid, ethane-1,2-disulfonic acid, ethanesulfonic acid, methanesulfonic acid, 2-hydroxyethanesulfonic acid, benzenesulfonic acid, 4-methylbenzenesulfonic acid, naphthalene-2-sulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d)

salts formed from elemental anions such as chlorine, bromine, and iodine.

C. Other Bioequivalents: Although many backbone modifications to an antisense compound can influence its hybridization to its target nucleic acid, some backbone modifications have little or no effect on the efficacy of a given antisense compound and are thus bioequivalents of the compound. In the case of antisense oligonucleotides described herein as having full phosphorothioate backbones, bioequivalents include compounds in which the backbones are mixed. For example, bioequivalents would include, but are not limited to, compounds having one or more monodiester or diester linkages provided, however, that phosphodiester linkages are not present at either termini and that no more than four adjacent phosphodiester linkages are present internally. Thus, bioequivalents of the phosphorothioate oligonucleotides of the invention include, for example, oligonucleotides having mixed phosphodiester and phosphorothioate backbones.

3. Exemplary Utilities of the Invention: The oligonucleotides of the present invention specifically hybridize to nucleic acids (e.g., mRNAs) encoding an ICAM-1 protein. The antisense compounds of the present invention can be utilized as therapeutic compounds, as diagnostic tools or research reagents that can be incorporated into kits as well as other methodologies as will be apparent to persons of ordinary skill in the art.

A. Assays and Diagnostic Applications: The oligonucleotides of the present invention can be used to detect the presence of ICAM-1 protein-specific nucleic acids in a cell or tissue sample. For example, radiolabeled oligonucleotides can be prepared by $^{32}$P labeling at the 5' end with polynucleotide kinase. (Sambrook et al., *Molecular Cloning. A Laboratory Manual,* Cold Spring Harbor Laboratory Press, 1989, Volume 2, pg. 10.59.) Radiolabeled oligonucleotides are then contacted with cell or tissue samples suspected of containing ICAM-1 protein message RNAs (and thus ICAM-1 proteins), and the samples are washed to remove unbound oligonucleotide. Radioactivity remaining in the sample indicates the presence of bound oligonucleotide, which in turn indicates the presence of nucleic acids complementary to the oligonucleotide, and can be quantitated using a scintillation counter or other routine means. Expression of nucleic acids encoding these proteins is thus detected.

Radiolabeled oligonucleotides of the present invention can also be used to perform autoradiography of tissues to determine the localization, distribution and quantitation of ICAM-1 proteins for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing an ICAM-1 protein gene. Quantitation of the silver grains permits detection of the expression of mRNA molecules encoding these proteins and permits targeting of oligonucleotides to these areas.

Analogous assays for fluorescent detection of expression of ICAM-1 protein nucleic acids can be developed using oligonucleotides of the present invention which are conjugated with fluorescein or other fluorescent tags instead of radiolabeling. Such conjugations are routinely accomplished during solid phase synthesis using fluorescently-labeled amidites or controlled pore glass (CPG) columns. Fluorescein-labeled amidites and CPG are available from, e.g., Glen Research, Sterling Va. Other means of labeling oligonucleotides are known in the art (see, e.g., Ruth, Chapter 6 *In: Methods in Molecular Biology,* Vol. 26: *Protocols for Oligonucleotide Conjugates,* Agrawal, ed., Humana Press Inc., Totowa, N.J., 1994, pages 167–185).

Kits for detecting the presence or absence of expression of an ICAM-1 protein may also be prepared. Such kits include an oligonucleotide targeted to an appropriate gene, i.e., a gene encoding an ICAM-1 protein. Appropriate kit and assay formats, such as, e.g., "sandwich" assays, are known in the art and can easily be adapted for use with the antisense compounds of the invention. Hybridization of the antisense compounds of the invention with a nucleic acid encoding an ICAM-1 protein can be detected by means known in the art. Such means may include conjugation of an enzyme to the oligonucleotide, radiolabelling of the oligonucleotide or any other suitable detection systems.

B. Biologically Active Oligonucleotides: The invention is also drawn to the administration of oligonucleotides having biological activity to cultured cells, isolated tissues and organs and animals. By "having biological activity," it is meant that the oligonucleotide functions to modulate the expression of one or more genes in cultured cells, isolated tissues or organs and/or animals. Such modulation can be achieved by an antisense oligonucleotide by a variety of mechanisms known in the art, including but not limited to transcriptional arrest; effects on RNA processing (capping, polyadenylation and splicing) and transportation; enhancement of cellular degradation of the target nucleic acid; and translational arrest (Crooke et al., *Exp. Opin. Ther. Patents,* 1996, 6:855).

In an animal other than a human, the compositions and methods of the invention can be used to study the function of one or more genes in the animal. For example, antisense oligonucleotides have been systemically administered to rats in order to study the role of the N-methyl-D-aspartate receptor in neuronal death, to mice in order to investigate the biological role of protein kinase C-α, and to rats in order to examine the role of the neuropeptide Y1 receptor in anxiety (Wahlestedt et al., *Nature,* 1993, 363:260; Dean et al., *Proc. Natl. Acad. Sci. U.S.A.,* 1994, 91:11762; and Wahlestedt et al., *Science,* 1993, 259:528, respectively). In instances where complex families of related proteins are being investigated, "antisense knockouts" (i.e., inhibition of a gene by systemic administration of antisense oligonucleotides) may represent the most accurate means for examining a specific member of the family (see, generally, Albert et al., *Trends Pharmacol. Sci.,* 1994, 15:250).

The compositions and methods of the invention also have therapeutic uses in an animal, including a human, having (i.e., suffering from), or known to be or suspected of being prone to having, a disease or disorder that is treatable in whole or in part with one or more nucleic acids. The term "therapeutic uses" is intended to encompass prophylactic, palliative and curative uses wherein the antisense compounds of the invention are contacted with animal cells either in vivo or ex vivo. When contacted with animal cells ex vivo, a therapeutic use includes incorporating such cells into an animal after treatment with one or more of the antisense compounds of the invention.

For therapeutic uses, an animal suspected of having a disease or disorder which can be treated or prevented by modulating the expression or activity of an ICAM-1 protein is, for example, treated by administering oligonucleotides in accordance with this invention. The antisense compounds of the invention can be utilized in pharmaceutical compositions by adding an effective amount of an oligonucleotide to a suitable pharmaceutically acceptable carrier such as, e.g., a diluent. Workers in the field have identified antisense, triplex and other oligonucleotide compositions which are capable of modulating expression of genes implicated in viral, fungal and metabolic diseases. Antisense oligonucleotides have been safely administered to humans and several clinical trials are presently underway. It is thus established that oligonucleotides can be useful therapeutic instrumentalities that can be configured to be useful in treatment regimes for treatment of cells, tissues and animals, especially humans. The following U.S. patents demonstrate palliative, therapeutic and other methods utilizing antisense oligonucleotides. U.S. Pat. No. 5,135,917 provides antisense oligonucleotides that inhibit human interleukin-1 receptor expression. U.S. Pat. No. 5,098,890 is directed to antisense oligonucleotides complementary to the c-myb oncogene and antisense oligonucleotide therapies for certain cancerous conditions. U.S. Pat. No. 5,087,617 provides methods for treating cancer patients with antisense oligonucleotides. U.S. Pat. No. 5,166,195 provides oligonucleotide inhibitors of Human Immunodeficiency Virus (HIV). U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenzavirus. U.S. Pat. No. 4,806,463 provides antisense oligonucleotides and methods using them to inhibit HTLV-III replication. U.S. Pat. No. 5,286,717 provides oligonucleotides having a complementary base sequence to a portion of an oncogene. U.S. Pat. No. 5,276,019 and U.S. Pat. No. 5,264,423 are directed to phosphorothioate oligonucleotide analogs used to prevent replication of foreign nucleic acids in cells. U.S. Pat. No. 4,689,320 is directed to antisense oligonucleotides as antiviral agents specific to cytomegalovirus (CMV). U.S. Pat. No. 5,098,890 provides oligonucleotides complementary to at least a portion of the mRNA transcript of the human c-myb gene. U.S. Pat. No. 5,242,906 provides antisense oligonucleotides useful in the treatment of latent Epstein-Barr virus (EBV) infections.

As used herein, the term "disease or disorder" (1) includes any abnormal condition of an organism or part, especially as a consequence of infection, inherent weakness, environmental stress, that impairs normal physiological functioning; (2) excludes pregnancy per se but not autoimmune and other diseases associated with pregnancy; and (3) includes cancers and tumors. The term "known to be or suspected of being prone to having a disease or disorder" indicates that the subject animal has been determined to be, or is suspected of being, at increased risk, relative to the general population of such animals, of developing a particular disease or disorder as herein defined. For example, a subject animal "known to be or suspected of being prone to having a disease or disorder" could have a personal and/or family medical history that includes frequent occurrences of a particular disease or disorder. As another example, a subject animal "known to be or suspected of being prone to having a disease or disorder" could have had such a susceptibility determined by genetic screening according to techniques known in the art (see, e.g., U.S. Congress, Office of Technology Assessment, Chapter 5 In: Genetic Monitoring and Screening in the Workplace, OTA-BA-455, U.S. Government Printing Office, Washington, D.C., 1990, pages 75–99). The term "a disease or disorder that is treatable in whole or in part with one or more antisense compounds" refers to a disease or disorder, as herein defined, (1) the management, modulation or treatment thereof, and/or (2) therapeutic, curative, palliative and/or prophylactic relief therefrom, can be provided via the administration of compositions comprising one or more antisense compounds of the invention.

4. Pharmaceutical Compositions Comprising Compounds of the Invention: The present invention provides for therapeutic and pharmaceutical compositions comprising one or more ICAM-1-modulating antisense compounds. Compositions for the administration of the antisense compounds of the invention may include sterile aqueous solutions which may also contain buffers, diluents and other suitable additives.

A. Compositions for Alimentary Delivery: In a preferred embodiment of the invention, one or more ICAM-1-modulating antisense compounds are administered via alimentary delivery, preferably by oral administration. Pharmaceutical compositions for oral administration include powders or granules, suspensions or solutions in water or non-aqueous media, capsules, sachets, troches, tablets or SECs (soft elastic capsules or "caplets"). Thickeners, flavoring agents, diluents, emulsifiers, dispersing aids, carrier substances or binders may be added to such compositions. Such pharmaceutical compositions have the effect of delivering the antisense compound(s) to the alimentary canal for exposure to the mucosa thereof. Accordingly, the pharmaceutical composition can comprise material effective in protecting the oligonucleotide from pH extremes of the stomach, or in releasing the oligonucleotide over time, to optimize the delivery thereof to a particular mucosal site. Enteric coatings for acid-resistant tablets, capsules and caplets are known in the art and typically include acetate phthalate, propylene glycol and sorbitan monoleate. Various methods for producing pharmaceutical compositions for alimentary delivery are well known in the art. See, generally, Nairn, Chapter 83; Block, Chapter 87; Rudnic et al., Chapter 89; Porter, Chapter 90; and Longer et al., Chapter 91 In: Remington's Pharmaceutical Sciences, 18th Ed., Gennaro, ed., Mack Publishing Co., Easton, Pa., 1990.

The antisense compounds of the invention can be incorporated in a known manner into customary pharmaceutical compositions, such as tablets, coated tablets, pills, granules, aerosols, syrups, emulsions, suspensions and solutions, using inert, non-toxic, pharmaceutically acceptable carriers (excipients). The therapeutically active compound should in each case be present here in a concentration of about 0.5% to about 95% by weight of the total mixture, i.e., in amounts which are sufficient to achieve the stated dosage range. The pharmaceutical compositions are prepared, for example, by diluting the active compounds with pharmaceutically acceptable carriers, if appropriate using emulsifying agents and/or dispersing agents, and, for example, in the case where water is used as the diluent, organic solvents can be used as auxiliary solvents if appropriate. Pharmaceutical compositions may be formulated in a conventional manner using additional pharmaceutically acceptable carriers as appropriate. Thus, the compositions may be prepared by conventional means with additional excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrates (e.g., starch or sodium starch glycolate); or wetting agents (e.g., sodium lauryl sulfate). Tablets are coated by methods well known in the art and may also contain flavoring, coloring and/or sweetening agents.

Compositions comprising one or more ICAM-1-modulating antisense compounds can be administered via the rectal mode. In particular, therapeutic or pharmaceutical compositions for rectal administration include foams, solutions (enemas) and suppositories. Rectal suppositories for adults are usually tapered at one or both ends and typically weigh about 2 g each, with infant rectal suppositories typically weighing about one-half as much when the usual base, cocoa butter, is used (Block, Chapter 87 In: Remington's Pharmaceutical Sciences, 18th Ed., Gennaro, ed., Mack Publishing Co., Easton, Pa., 1990).

The pharmaceutical compositions, which may conveniently be presented in unit dosage form, may be prepared according to conventional techniques well known in the pharmaceutical industry. Such techniques include the step of bringing into association the active ingredient(s) with the pharmaceutically acceptable carrier(s). In general the pharmaceutical compositions are prepared by uniformly and intimately bringing into association the active ingredient(s) with liquid excipients or finely divided solid excipients or both, and then, if necessary, shaping the product.

Pharmaceutical compositions of the present invention suitable for oral administration may be presented as discrete units such as capsules, cachets or tablets each containing predetermined amounts of the active ingredients; as powders or granules; as solutions or suspensions in an aqueous liquid or a non-aqueous liquid; or as oil-in-water emulsions or water-in-oil liquid emulsions. A tablet may be made by compression or molding, optionally with one or more accessory ingredients. Compressed tablets may be prepared by compressing in a suitable machine, the active ingredients in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredients therein. Sustained release oral delivery systems and/or enteric coatings for orally administered dosage forms are described in U.S. Pat. Nos. 4,704,295; 4,556,552; 4,309,406; and 4,309,404.

B. Additives: Pharmaceutical and therapeutic compositions comprising one or more of the antisense compounds of the invention may further include sterile aqueous solutions which may also contain buffers, diluents and other suitable additives. Pharmaceutically acceptable organic or inorganic carrier substances suitable for non-parenteral administration which do not deleteriously react with the antisense compounds can be used. The pharmaceutical compositions can be sterilized and, if desired, mixed with auxiliary agents, e.g., lubricants, preservatives, stabilizers, wetting agents, emulsifiers, salts for influencing osmotic pressure, buffers, colorings flavorings and/or aromatic substances and the like which do not deleteriously react with the oligonucleotide(s) of the pharmaceutical composition. Pharmaceutical compositions in the form of aqueous suspensions may contain substances which increase the viscosity of the suspension including, for example, sodium carboxymethylcellulose, sorbitol and/or dextran. Optionally, such compositions may also contain one or more stabilizers, penetration enhancers, carrier compounds or pharmaceutically acceptable carriers.

(1) Penetration Enhancers: Pharmaceutical compositions comprising the oligonucleotides of the present invention may also include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., Critical Reviews in Therapeutic Drug Carrier Systems, 1991, 8:91–192; Muranishi, Critical Reviews in Therapeutic Drug Carrier Systems, 1990, 7:1).

Fatty Acids: Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, acylcarnitines, acylcholines, 1-dodecylazacycloheptan-2-one, mono- and di-glycerides and physiologically acceptable salts thereof (i.e., oleate, laurate, caprate, myristate, palmitate, stearate, linoleate, etc.) (Lee et al., Critical Reviews in Therapeutic Drug Carrier Systems, 1991, page 92; Muranishi, Critical Reviews in Therapeutic Drug Carrier Systems, 1990, 7:1; El-Hariri et al., J. Pharm. Pharmacol., 1992, 44:651).

Bile Salts: The physiological roles of bile include the facilitation of dispersion and absorption of lipids and fat-soluble vitamins (Brunton, Chapter 38 In: Goodman & Gilman's The Pharmacological Basis of Therapeutics, 9th Ed., Hardman et al., eds., McGraw-Hill, New York, N.Y., 1996, pages 934–935). Various natural bile salts, and their synthetic derivatives, act as penetration enhancers. Thus, "bile salt" includes any of the naturally occurring components of bile and any of their synthetic derivatives.

Chelating Agents: Chelating agents have the added advantage of also serving as DNase inhibitors and include, but are not limited to, citric acid, disodium ethylenediaminetetraacetate (EDTA), salicylates (e.g., sodium salicylate, 5-methoxysalicylate and homovanilate), N-acyl derivatives of collagen, laureth-9 and N-amino acyl derivatives of beta-diketones (enamines) (Lee et al., Crit. Rev. Therap. Drug Carrier Systems, 1991, p. 92; Muranishi, Crit. Rev. Therap. Drug Carrier Systems, 1990, 7, 1; Buur et al., J. Control Rel., 1990, 14, 43).

Surfactants: Surfactants include, for example, sodium lauryl sulfate, polyoxyethylene-9-lauryl ether and polyoxyethylene-20-cetyl ether (Lee et al., Critical Reviews in Therapeutic Drug Carrier Systems, 1991, page 92); and perfluorochemical emulsions, such as FC-43 (Takahashi et al., J. Pharm. Phamacol., 1988, 40:252).

Non-Surfactants: Non-surfactants include, for example, unsaturated cyclic ureas, 1-alkyl- and 1-alkenylazacycloalkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39:621).

(2) Carrier Compounds: As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioated oligonucleotide in hepatic tissue is reduced when it is coadministered with polyinosinic acid, dextran sulfate, polycytidic acid or 4-acetamido-4'-isothiocyano-stilbene-2,2'-disulfonic acid (Miyao et al., Antisense Res. Dev., 1995, 5:115; Takakura et al., Antisense & Nucl. Acid Drug Dev., 1996, 6:177).

(3) Pharmaceutically Acceptable Carriers: In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Suitable pharmaceutically acceptable carriers include, but are not limited to, water, salt solutions, alcohol, polyethylene glycols, gelatin, lactose, amylose, magnesium stearate, talc, silicic acid, hydroxymethylcellulose, polyvinylpyrrolidone viscous paraffin and the like.

(4) Miscellaneous Additional Components: The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

C. Colloidal Dispersion Systems: Regardless of the method by which the antisense compounds of the invention are introduced into a patient, colloidal dispersion systems may be used as delivery vehicles to enhance the in vivo stability of the compounds and/or to target the compounds to a particular organ, tissue or cell type. Colloidal dispersion systems include, but are not limited to, macromolecule complexes, nanocapsules, microspheres, beads and lipid-based systems including oil-in-water emulsions, micelles, mixed micelles, lipid: oligonucleotide complexes of uncharacterized structure and liposomes.

A preferred colloidal dispersion system is a plurality of liposomes. Liposomes are microscopic spheres having an aqueous core surrounded by one or more outer layer(s) made up of lipids arranged in a bilayer configuration (see, generally, Chonn et al., *Current Op. Biotech.*, 1995, 6, 698). The therapeutic potential of liposomes as drug delivery agents was recognized nearly thirty years ago (Sessa et al., *J. Lipid Res.*, 1968, 9, 310). Liposomes, in some instances, may be used as cellular delivery vehicles for bioactive agents in vitro and in vivo (Mannino et al., *Biotechniques*, 1988, 6, 682; Blume et al., *Biochem. et Biophys. Acta*, 1990, 1029, 91; Lappalainen et al., *Antiviral Res.*, 1994, 23, 119. For example, it has been shown that large unilamellar vesicles (LUV), which range in size from 0.2–0.4 microns, can encapsulate a substantial percentage of an aqueous buffer containing large macromolecules. RNA, DNA and intact virions can be encapsulated within the aqueous interior and delivered to brain cells in a biologically active form (Fraley et al., *Trends Biochem. Sci.*, 1981, 6, 77).

The targeting of colloidal dispersion systems, including liposomes, can be either passive or active. Passive targeting utilizes the natural tendency of liposomes to distribute to cells of the reticuloendothelial system in organs that contain sinusoidal capillaries. Active targeting, by contrast, involves modification of the liposome by coupling thereto a specific ligand such as a viral protein coat (Morishita et al., *Proc. Natl. Acad. Sci. (U.S.A.)*, 1993, 90, 8474), monoclonal antibody (or a suitable binding portion thereof), sugar, glycolipid or protein (or a suitable oligopeptide fragment thereof), or by changing the composition and/or size of the liposome in order to achieve distribution to organs and cell types other than the naturally occurring sites of localization.

The surface of the targeted colloidal dispersion system can be modified in a variety of ways. In the case of a liposomal targeted delivery system, lipid groups can be incorporated into the lipid bilayer of the liposome in order to maintain the targeting ligand in close association with the lipid bilayer. Various linking groups can be used for joining the lipid chains to the targeting ligand. The targeting ligand, which binds a specific cell surface molecule found predominantly on cells to which delivery of the compounds of the invention is desired, may be, for example, (1) a hormone, growth factor or a suitable oligopeptide fragment thereof which is bound by a specific cellular receptor predominantly expressed by cells to which delivery is desired or (2) a polyclonal or monoclonal antibody, or a suitable fragment thereof (e.g., Fab; $F(ab')_2$) which specifically binds an antigenic epitope found predominantly on targeted cells. Two or more bioactive agents (e.g., an antisense oligonucleotide and a conventional drug; two oligonucleotides) can be combined within, and delivered by, a single liposome. It is also possible to add agents to colloidal dispersion systems which enhance the intercellular stability and/or targeting of the contents thereof.

The liposomes of the invention are formed from vesicle-forming lipids which generally include one or more neutral or negatively charged phospholipids, preferably one or more neutral phospholipids, usually in combination with one or more sterols, particularly cholesterol. Examples of lipids useful in liposome production include phosphatidyl compounds, such as phosphatidylglycerol, phosphatidylcholine, phosphatidylserine, sphingolipids, phosphatidylethanolamine, cerebrosides and gangliosides. Typically, the major lipid component of the liposomes is a phosphatidylcholine (PC) or PC derivative. PC derivatives with a variety of acyl chain groups of varying chain length and degree of saturation are commercially available or may be synthesized by known techniques. For purposes of filter sterilization, less-saturated PCS are generally more easily sized, particularly when the liposomes must be sized below about 0.3 microns. PCS containing saturated fatty acids with carbon chain lengths in the range of $C_{14}$ to $C_{22}$, particularly $C_{16}$ to $C_{18}$, are preferred, particularly diacyl phosphatidylglycerols. Illustrative phospholipids include, for example, dipalmitoylphosphatidylcholine, phosphatidylcholine and distearoylphosphatidylcholine. Phosphatidylcholines with mono- and di-unsaturated fatty acids and mixtures of saturated and unsaturated fatty acids may also be used. Other suitable phospholipids include those with head groups other than choline, such as, for example, ethanolamine, serine, glycerol and inositol. Other suitable lipids include phosphonolipids in which the fatty acids are linked to glycerol via ether linkages rather than ester linkages. Preferred liposomes will include a sterol, e.g., cholesterol, at molar ratios of from about 0.1 to 1.0 (sterol: phospholipid).

Typically, the liposomes of the invention will contain, in their aqueous interiors, one or more antisense oligonucleotides in an amount of from about 0.005 ng/mL to about 400 mg/mL, preferably from about 0.01 ng/mL to about 200 mg/mL, most preferably from about 0.1 ng/mL to about 100 mg/mL, where "about" indicates ±5% of the desired concentration.

Compositions of the invention may include one or more antisense compounds and/or other therapeutic agents entrapped within sterically stabilized liposomes. As used herein, the term "sterically stabilized liposome" refers to a liposome comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (Allen et al., *FEBS Letts.*, 1987, 223, 42; Wu et al., *Cancer Res.*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Ilium et al. (*FEBS Letters*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Letts.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. 0,445,131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0,496,813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized via functional surface moieties.

A limited number of liposomes comprising nucleic acids are known in the art. Published PCT application No. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene. WO 97/46671 to Klimuk et al. discloses liposomes comprising antisense oligonucleotides targeted to genes encoding ICAM-1. One or more antisense compounds of the invention can be formulated in a lipid:antisense compound complex comprising one or more cationic lipids as disclosed in U.S. Pat. No. 5,705,385 to Bally et al. and in WO 96/40964 to Wheeler et al., or in lipoprotein-containing complexes such as are described in WO 98/00556 to Kim et al.

The liposomes of the invention can be prepared by any of a variety of known techniques. For example, the liposomes can be formed by any conventional technique for preparing multilamellar lipid vesicles (MLVs), i.e., by depositing one or more selected lipids on the inside wall of a suitable vessel by dissolving the lipid in chloroform, evaporating the chloroform and then adding an aqueous solution which comprises the agent(s) to be encapsulated to the vessel, allowing the aqueous solution to hydrate the lipid, and swirling or vortexing the resulting lipid suspension. This process yields a mixture including the desired liposomes.

As another example, techniques used for producing large unilamellar vesicles (LUVs), such as, e.g., reverse-phase evaporation, infusion procedures and detergent dilution, can be used to produce the liposomes. These and other methods for producing lipid vesicles are described in *Liposome Technology, Volume I* (Gregoriadis, Ed., CRC Press, Boca Raton, Fla., 1984). The liposomes can be in the form of steroidal lipid vesicles, stable plurilamellar vesicles (SPLVs), monophasic vesicles (MPVs) or lipid matrix carriers (LMCs) of the type disclosed in U.S. Pat. Nos. 4,588,578 and 4,610,868 (both to Fountain et al.), U.S. Pat. No. 4,522,803 (to Lenk et al.), and U.S. Pat. No. 5,008,050 (to Cullis et al.). In the case of MLVs, the liposomes can be subjected to multiple (five or more) freeze-thaw cycles to enhance their trapped volumes and trapping efficiencies and to provide a more uniform interlamellar distribution of solute if desired (Mayer et al., *J. Biol. Chem.*, 1985, 260, 802). Specific methods for making particular oligodeoxynucleotide:liposome compositions are described in U.S. Pat. No. 5,665,710 to Rahman et al.

Following their preparation, liposomes may be sized to achieve a desired size range and relatively narrow distribution of sized particles. In preferred embodiments, the liposomes have a lower range of diameters of from about 50 to about 75 nM, most preferably about 60 nM, and an upper range of diameters from about 75 to about 150 nM, most preferably about 125 nM, where "about" indicates ±10 nM.

Several techniques are available for sizing liposomes to a desired size range. Sonicating a liposome suspension by either bath or probe sonication produces a progressive size reduction down to small unilamellar vesicles (SUVs) less than about 0.05 microns in size. Homogenization, which relies on shearing energy to fragment large liposomes into smaller ones, is another known sizing technique in which MLVs are recirculated through a standard emulsion homogenizer until a selected liposome size range, typically between about 0.1 and about 0.5 microns, is achieved. Extrusion of liposomes through a filter or membrane is another method for producing liposomes having a desired size range (see, for example, U.S. Pat. No. 4,737,323 to Martin et al. and U.S. Pat. No. 5,008,050 to Cullis et al.). Other useful sizing methods are known to those skilled in the art. In most such methods, the particle size distribution can be monitored by conventional laser-beam size determination or other means known in the art.

Liposomes may be dehydrated, preferably under reduced pressure using standard freeze-drying equipment, for extended storage. Whether dehydrated or not, the liposomes and their surrounding media can first be frozen in liquid nitrogen and placed under reduced pressure. Although the addition of the latter freezing step makes for a longer overall dehydration process, there is less damage to the lipid vesicles, and less loss of their internal contents, when the liposomes are frozen before dehydration.

To ensure that the a significant portion of the liposomes will endure the dehydration process intact, one or more protective sugars may be made available to interact with the lipid vesicle membranes and keep them intact as water is removed. Appropriate sugars include, but are not limited to, trehalose, maltose, sucrose, lactose, glucose, dextran and the like. In general, disaccharide sugars may work better than monosaccharide sugars, with trehalose and sucrose being particularly effective in most cases, but other, more complicated sugars may alternatively be used. The amount of sugar to be used depends on the type of sugar and the characteristics of the lipid vesicles. Persons skilled in the art can readily test various sugars and concentrations to determine what conditions work best for a particular lipid vesicle preparation (see, generally, Harrigan et al., *Chem. Phys. Lipids,* 1990, 52, 139, and U.S. Pat. No. 4,880,635 to Janoff et al.). Generally, sugar concentrations of greater than or equal to about 100 mM have been found to result in the desired degree of protection. Once the liposomes have been dehydrated, they can be stored for extended periods of time until they are to be used. The appropriate conditions for storage will depend on the chemical composition of the lipid vesicles and their encapsulated active agent(s). For example, liposomes comprising heat labile agents should be stored under refrigerated conditions so that the potency of the active agent is not lost.

Two or more bioactive agents (e.g., an oligonucleotide and a conventional drug, or two or more oligonucleotides; see below) can be combined within, and delivered by, a single liposome. It is also possible to add agents to colloidal dispersion systems which enhance the intercellular stability and/or targeting of the contents thereof.

5. Methods of Administration of Compounds of the Invention: The administration of therapeutic or pharmaceutical compositions comprising the antisense compounds of the invention is believed to be within the skill of those in the art. In general, a patient in need of therapy or prophylaxis is administered a composition comprising one or more antisense compounds in accordance with the invention, commonly in a pharmaceutically acceptable carrier, in doses ranging from 0.01 ug to 100 g per kg of body weight depending on the age of the patient and the severity of the disorder or disease state being treated. Dosing is dependent on severity and responsiveness of the disease state to be treated, with the course of treatment lasting from several days to several months, or until a cure is effected or a diminution or prevention of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual antisense compounds, and can generally be estimated based on $EC_{50}$s found to be effective in in vitro and in vivo animal models.

A. Treatment Regimens: In the context of the invention, the term "treatment regimen" is meant to encompass therapeutic, palliative and prophylactic modalities of administration of one or more compositions comprising one or more antisense compounds of the invention. A particular treatment regimen may last for a period of time which will vary depending upon the nature of the particular disease or disorder, its severity and the overall condition of the patient, and may extend from once daily to once every 20 years. Following treatment, the patient is monitored for changes in his/her condition and for alleviation of the symptoms of the disorder or disease state. The dosage of the oligonucleotide may either be increased in the event the patient does not respond significantly to current dosage levels, or the dose may be decreased if an alleviation of the symptoms of the disorder or disease state is observed, or if the disorder or disease state has been ablated.

An optimal dosing schedule is used to deliver a therapeutically effective amount of the oligonucleotide being administered via a particular mode of administration. The term "therapeutically effective amount," for the purposes of the invention, refers to the amount of oligonucleotide-containing pharmaceutical composition which is effective to achieve an intended purpose without undesirable side effects (such as toxicity, irritation or allergic response). Although individual needs may vary, determination of optimal ranges for effective amounts of pharmaceutical compositions is within the skill of the art. Human doses can be extrapolated from animal studies (Katocs et al., Chapter 27 *In: Remington's Pharmaceutical Sciences,* 18th Ed., Gennaro, ed., Mack Publishing Co., Easton, Pa., 1990). Generally, the dosage required to provide an effective amount of a pharmaceutical composition, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect(s) (Nies et al., Chapter 3 *In: Goodman & Gilman's The Pharmacological Basis of Therapeutics,* 9th Ed., Hardman et al., eds., McGraw-Hill, New York, N.Y., 1996).

Following successful treatment, it may be desirable to have the patient undergo maintenance therapy to prevent the recurrence of the disease state, wherein the nucleic acid is administered in maintenance doses, ranging from 0.01 ug to 100 g per kg of body weight, once or more daily, to once every 20 years. For example, in the case of in individual known or suspected of being prone to an autoimmune or inflammatory condition, prophylactic effects may be achieved by administration of preventative doses, ranging from 0.01 ug to 100 g per kg of body weight, once or more daily, to once every 20 years. In like fashion, an individual may be made less susceptible to an inflammatory condition that is expected to occur as a result of some medical treatment, e.g., graft versus host disease resulting from the transplantation of cells, tissue or an organ into the individual.

In another method of the invention, a first antisense oligonucleotide targeted to a first ICAM-1 protein is used in combination with a second antisense oligonucleotide targeted to a second ICAM-1 protein in order to modulate such ICAM-1 proteins to a more extensive degree than can be achieved when either oligonucleotide is used individually. In various embodiments of the invention, the first and second ICAM-1 proteins which are targeted by such oligonucleotides are identical, are different ICAM-1 proteins or are different isoforms of the same ICAM-1 protein.

In some cases it may be more effective to treat a patient with a composition comprising one or more antisense compounds of the invention in conjunction with other, traditional therapeutic modalities in order to increase the efficacy of a treatment regimen. In the context of the invention, the term "treatment regimen" is meant to encompass therapeutic, palliative and prophylactic modalities. Following treatment, the patient is monitored for changes in his/her condition and for alleviation of the symptoms of the disorder or disease state. The dosage of the therapeutic or pharmaceutical composition may either be increased in the event the patient does not respond significantly to current dosage levels, or the dose may be decreased if an alleviation of the symptoms of the disorder or disease state is observed, or if the disorder or disease state has been ablated.

Prophylactic modalities for high risk individuals are also encompassed by the invention. As used herein, the term "high risk individual" is meant to refer to an individual for whom it has been determined, via, e.g., individual or family history or genetic testing, that there is a significantly higher than normal probability of being susceptible to the onset or recurrence of a disease or disorder. As part of a treatment regimen for a high risk individual, the individual can be prophylactically treated to prevent the onset or recurrence of the disease or disorder. The term "prophylactically effective amount" is meant to refer to an amount of a pharmaceutical composition which produces an effect observed as the prevention of the onset or recurrence of a disease or disorder. Prophylactically effective amounts of a pharmaceutical composition are typically determined by the effect they have compared to the effect observed when a second pharmaceutical composition lacking the active agent is administered to a similarly situated individual. The therapeutic and pharmaceutical compositions of the present invention may be administered in a number of ways depending upon whether local or systemic treatment is desired and upon the area to be treated. Typically, either oral or parenteral administration is employed.

B. Parenteral Delivery: The term "parenteral delivery" refers to the administration of one or more antisense compounds of the invention to an animal in a manner other than through the digestive canal. Parenteral administration includes intravenous (i.v.) drip, subcutaneous, intraperitoneal (i.p.) or intramuscular injection, or intrathecal or intraventricular administration. Compositions for parenteral, intrathecal or intraventricular administration may include sterile aqueous solutions which may also contain buffers, diluents and other suitable additives. Means of preparing and administering parenteral pharmaceutical compositions are known in the art (see, e.g., Avis, Chapter 84 *In: Remington's Pharmaceutical Sciences,* 18th Ed., Gennaro, ed., Mack Publishing Co., Easton, Pa., 1990, pages 1545–1569). Parenteral means of delivery include, but are not limited to, the following illustrative examples.

Intravitreal injection, for the direct delivery of drug to the vitreous humor of a mammalian eye, is described in U.S. Pat. No. 5,591,720, the contents of which are hereby incorporated by reference. Means of preparing and administering ophthalmic preparations are known in the art (see, e.g., Mullins et al., Chapter 86 *In: Remington's Pharmaceutical Sciences,* 18th Ed., Gennaro, ed., Mack Publishing Co., Easton, Pa., 1990, pages 1581–1595).

Intravenous administration of antisense oligonucleotides to various non-human mammals has been described by Iversen (Chapter 26 *In: Antisense Research and Applications,* Crooke et al., eds., CRC Press, Boca Raton, Fla., 1993, pages 461–469). Systemic delivery of oligonucleotides to non-human mammals via intraperitoneal means has also been described (Dean et al., *Proc. Natl. Acad. Sci. U.S.A.,* 1994, 91, 11766).

Intraluminal drug administration, for the direct delivery of drug to an isolated portion of a tubular organ or tissue (e.g., such as an artery, vein, ureter or urethra), may be desired for the treatment of patients with diseases or conditions afflicting the lumen of such organs or tissues. To effect this mode of oligonucleotide administration, a catheter or cannula is surgically introduced by appropriate means. For example, for treatment of the left common carotid artery, a cannula is inserted thereinto via the external carotid artery. After isolation of a portion of the tubular organ or tissue for which treatment is sought, a composition comprising the antisense compounds of the invention is infused through the cannula or catheter into the isolated segment. After incubation for from about 1 to about 120 minutes, during which the oligonucleotide is taken up by cells of the interior lumen of the vessel, the infusion cannula or catheter is removed and flow within the tubular organ or tissue is restored by removal of the ligatures which effected the isolation of a segment thereof (Morishita et al., *Proc. Natl. Acad. Sci. U.S.A.,* 1993, 90, 8474). Antisense oligonucleotides may also be combined with a biocompatible matrix, such as a hydrogel material, and applied directly to vascular tissue in vivo (Rosenberg et al., U.S. Pat. No. 5,593,974, issued Jan. 14, 1997).

Intraventricular drug administration, for the direct delivery of drug to the brain of a patient, may be desired for the treatment of patients with diseases or conditions afflicting the brain. To effect this mode of oligonucleotide administration, a silicon catheter is surgically introduced into a ventricle of the brain of a human patient, and is connected to a subcutaneous infusion pump (Medtronic Inc., Minneapolis, Minn.) that has been surgically implanted in the abdominal region (Zimm et al., *Cancer Research,* 1984, 44, 1698; Shaw, *Cancer,* 1993, 72(11 Suppl., 3416). The pump is used to inject the oligonucleotides and allows precise dosage adjustments and variation in dosage schedules with the aid of an external programming device. The reservoir capacity of the pump is 18–20 mL and infusion rates may range from 0.1 mL/h to 1 mL/h. Depending on the frequency of administration, ranging from daily to monthly, and the dose of drug to be administered, ranging from 0.01 ug to 100 g per kg of body weight, the pump reservoir may be refilled at 3–10 week intervals. Refilling of the pump is accomplished by percutaneous puncture of the pump's self-sealing septum.

Intrathecal drug administration, for the introduction of a drug into the spinal column of a patient may be desired for the treatment of patients with diseases of the central nervous system (CNS). To effect this route of oligonucleotide administration, a silicon catheter is surgically implanted into the L3–4 lumbar spinal interspace of a human patient, and is connected to a subcutaneous infusion pump which has been surgically implanted in the upper abdominal region (Luer and Hatton, *The Annals of Pharmacotherapy,* 1993, 27, 912, 1993; Ettinger et al. *Cancer,* 1978, 41, 1270; Yaida et al., *Regul. Pept.,* 1985, 59, 193). The pump is used to inject the oligonucleotides and allows precise dosage adjustments and variations in dose schedules with the aid of an external programming device. The reservoir capacity of the pump is 18–20 mL, and infusion rates may vary from 0.1 mL/h to 1 mL/h. Depending on the frequency of drug administration, ranging from daily to monthly, and dosage of drug to be administered, ranging from 0.01 ug to 100 g per kg of body weight, the pump reservoir may be refilled at 3–10 week intervals. Refilling of the pump is accomplished by a single percutaneous puncture to the self-sealing septum of the pump. The distribution, stability and pharmacokinetics of oligonucleotides within the CNS are followed according to known methods (Whitesell et al., *Proc. Natl. Acad. Sci. U.S.A.,* 1993, 90, 4665).

To effect delivery of oligonucleotides to areas other than the brain or spinal column via this method, the silicon catheter is configured to connect the subcutaneous infusion pump to, e.g., the hepatic artery, for delivery to the liver (Kemeny et al., *Cancer,* 1993, 71, 1964). Infusion pumps may also be used to effect systemic delivery of oligonucleotides (Ewel et al., *Cancer Res.,* 1992, 52, 3005; Rubenstein et al., *J. Surg. Oncol.,* 1996, 62, 194).

Epidermal and Transdermal Delivery, in which pharmaceutical compositions containing drugs are applied topically, can be used to administer drugs to be absorbed by the local dermis or for further penetration and absorption by underlying tissues, respectively. Means of preparing and administering medications topically are known in the art (see, e.g., Block, Chapter 87 *In: Remington's Pharmaceutical Sciences,* 18th Ed., Gennaro, ed., Mack Publishing Co., Easton, Pa., 1990, pages 1596–1609).

Vaginal Delivery provides local treatment and avoids first pass metabolism, degradation by digestive enzymes, and potential systemic side-effects. This mode of administration may be preferred for antisense oligonucleotides targeted to pathogenic organisms for which the vagina is the usual habitat, e.g., *Trichomonas vaginalis*. In another embodiment, antisense oligonucleotides to genes encoding sperm-specific antibodies can be delivered by this mode of administration in order to increase the probability of conception and subsequent pregnancy. Vaginal suppositories (Block, Chapter 87 *In: Remington's Pharmaceutical Sciences,* 18th Ed., Gennaro, ed., Mack Publishing Co., Easton, Pa., 1990, pages 1609–1614) or topical ointments can be used to effect this mode of delivery.

Intravesical Delivery provides local treatment and avoids first pass metabolism, degradation by digestive enzymes, and potential systemic side-effects. However, the method requires urethral catheterization of the patient and a skilled staff. Nevertheless, this mode of administration may be preferred for antisense oligonucleotides targeted to pathogenic organisms, such as *T. vaginalis,* which may invade the urogenital tract.

C. Alimentary Delivery: The term "alimentary delivery" refers to the administration, directly or otherwise, to a portion of the alimentary canal of an animal, of a composition comprising one or more of the antisense compounds of the invention. The term "alimentary canal" refers to the tubular passage in an animal that functions in the digestion and absorption of food and the elimination of food residue, which runs from the mouth to the anus, and any and all of its portions or segments, e.g., the oral cavity, the esophagus, the stomach, the small and large intestines and the colon, as well as compound portions thereof such as, e.g., the gastrointestinal tract. Thus, the term "alimentary delivery" encompasses several routes of administration including, but not limited to, oral, rectal, endoscopic and sublingual/buccal administration. Compositions for alimentary delivery may include sterile aqueous solutions which may also contain buffers, diluents and other suitable additives. Means of preparing and administering oral pharmaceutical compositions are known in the art (see, e.g., Block, Chapter 87; Rudnic, Chapter 89; Porter, Chapter 90; and Longer, Chapter 91, *In: Remington's Pharmaceutical Sciences,* 18th Ed., Gennaro, ed., Mack Publishing Co., Easton, Pa., 1990, pages 1596–1614, 133–1665, 1666–1675 and 1676–1693, respectively). Preferred compositions for the alimentary delivery of the antisense compounds of the invention are described in co-pending U.S. patent application Ser. No. 08/886,829 to Teng et al., filed Jul. 1, 1997, the entire disclosure of which is hereby incorporated by reference.

Buccal/Sublingual Administration: Delivery of a drug via the oral mucosa has several desirable features, including, in many instances, a more rapid rise in plasma concentration of the drug than via oral delivery (Harvey, Chapter 35 *In: Remington's Pharmaceutical Sciences,* 18th Ed., Gennaro, ed., Mack Publishing Co., Easton, Pa., 1990, page 711). Furthermore, because venous drainage from the mouth is to the superior vena cava, this route also bypasses rapid first-pass metabolism by the liver. Both features contribute to the sublingual route being the mode of choice for nitroglycerin (Benet et al., Chapter 1 *In: Goodman & Gilman's The Pharmacological Basis of Therapeutics,* 9th Ed., Hardman et al., eds., McGraw-Hill, New York, N.Y., 1996, page 7).

Endoscopic Administration: Endoscopy can be used for drug delivery directly to an interior portion of the alimentary tract. For example, endoscopic retrograde cystopancreatography (ERCP) takes advantage of extended gastroscopy and permits selective access to the biliary tract and the pancreatic duct (Hirahata et al., *Gan To Kagaku Ryoho,* 1992, 19(10 Suppl.), 1591). Pharmaceutical compositions, including liposomal formulations, can be delivered directly into portions of the alimentary canal, such as, e.g., the duodenum (Somogyi et al., *Pharm. Res.,* 1995, 12, 149) or the gastric submucosa (Akamo et al., *Japanese J. Cancer Res.,* 1994, 85, 652) via endoscopic means. Gastric lavage devices (Inoue et al., *Artif. Organs,* 1997, 21, 28) and percutaneous endoscopic feeding devices (Pennington et al., *Aliment. Pharmacol. Ther.,* 1995, 9, 471) can also be used for direct alimentary delivery of pharmaceutical compositions.

Rectal Administration: Drugs administered by the oral route can often be alternatively administered by the lower enteral route, i.e., through the anal portal into the rectum or lower intestine. Rectal suppositories, retention enemas or rectal catheters can be used for this purpose and may be preferred when patient compliance might otherwise be difficult to achieve (e.g., in pediatric and geriatric applications, or when the patient is vomiting or unconscious). Rectal administration may result in more prompt and higher blood levels than the oral route, but the converse may be true as well (Harvey, Chapter 35 *In: Remington's Pharmaceutical Sciences,* 18th Ed., Gennaro, ed., Mack Publishing Co., Easton, Pa., 1990, page 711). Because about 50% of the drug that is absorbed from the rectum will bypass the liver, administration by this route significantly reduces the potential for first-pass metabolism (Benet et al., Chapter 1 *In: Goodman & Gilman's The Pharmacological Basis of Therapeutics,* 9th Ed., Hardman et al., eds., McGraw-Hill, New York, N.Y., 1996).

Oral Administration: The preferred method of administration is oral delivery, which is typically the most convenient route for access to the systemic circulation. Absorption from the alimentary canal is governed by factors that are generally applicable, e.g., surface area for absorption, blood flow to the site of absorption, the physical state of the drug and its concentration at the site of absorption (Benet et al., Chapter 1 *In: Goodman & Gilman's The Pharmacological Basis of Therapeutics,* 9th Ed., Hardman et al., eds., McGraw-Hill, New York, N.Y., 1996, pages 5–7). Orally administered compositions comprising certain oligonucleotides are known in the art (see, for example, U.S. Pat. No. 5,591,721 to Agrawal et al.). Preferred compositions for the oral delivery of the antisense compounds of the invention are described in co-pending U.S. patent application Ser. No. 08/886,829 to Teng et al., filed Jul. 1, 1997, incorporated herein by reference.

EXAMPLES

The following examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention.

Example 1

Chemical Synthesis of Antisense Compounds

A. 2'-O-(2-Methoxyethyl) Modified Amidites

2'-O-Methoxyethyl-substituted nucleoside amidites are prepared as follows, or alternatively, as per the methods of Martin (*Helvetica Chimica Acta*, 1995, 78, 486).

2,2'-Anhydro[1-(beta-D-arabinofuranosyl)-5-methyluridine]: 5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine: 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine: 2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine: 2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84% ). An additional 1.5 g was recovered from later fractions.

3'-O-Acetyl-2'-O-methoxyethyl-5'-O-dimethoxytrityl-5-methyl-4-triazoleuridine: A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed once with 300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine: A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

$N^4$-Benzoyl-2'-O-methoxyethyl-5'-O-dimethoxytrityl-5-methylcytidine: 2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N$^4$-Benzoyl-2'-O-methoxyethyl-5'-O-dimethoxytrityl-5-methylcytidine-3'-amidite: N$^4$-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc\Hexane (3:1) as the eluting solvent. The pure fractions were combined to give 90.6 g (87%) of the title compound.

2'-(Aminooxyethyl) nucleoside amidites and 2'-(dimethylaminooxyethyl) nucleoside amidites: Aminooxyethyl and dimethylaminooxyethyl amidites are prepared as per the methods of U.S. patent application Ser. No. 10/037, 143, filed Feb. 14, 1998, and Ser. No. 09/016,520, filed Jan. 30, 1998, each of which is commonly owned with the instant application and is herein incorporated by reference.

B. Synthesis of Other Oligonucleotides

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 hr), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

C. Synthesis of PNAs

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

D. Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. oligonucleotides of the second type are also known in the art as "hemimers" or "wingmers."

[2'-O-Me]-[2'-deoxy]-[2'-O-Me] Chimeric Phosphorothioate Oligonucleotides: Chimeric oligonucleotides having 2'-O-alkyl phosphorothioate and 2'-deoxy phosphorothioate oligonucleotide segments are synthesized using an Applied Biosystems automated DNA synthesizer Model 380B, as above. oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 Ammonia/Ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometer.

[2'-O-(2-Methoxyethyl)]-[2'-deoxy]-[2'-O-(Methoxyethyl)] Chimeric Phosphorothioate Oligonucleotides: [2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotide

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

E. Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$p nuclear magnetic resonance spectroscopy, and for some studies oligonucleotides were purified by HPLC, as described by Chiang et al., *J. Biol. Chem.*, 1991, 266, 18162. Results obtained with HPLC-purified material were similar to those obtained with non-HPLC purified material.

Example 2

Nucleotide Sequences of Oligonucleotides Targeted to ICAM-1

Oligonucleotides Targeted to Nucleic Acids Encoding M-1: Tables 1 to 3 describe the nucleotide sequences and chemical structures of a set of oligonucleotides designed to specifically hybridize to human ICAM-1 nucleic acids and their corresponding ISIS and SEQ ID numbers. The nucleotide co-ordinates of the target gene and gene target regions are also included. The nucleotide co-ordinates are derived from GenBank Accession No. J03132, locus name "HUMICAMA1M" (SEQ ID NO: 1; see also FIG. 2 of Staunton et al., *Cell,* 1988, 52, 925). The abbreviations for gene target regions are as follows: 5'-UTR, 5' untranslated region; AUG, translation initiation region; ORF, open reading frame; stop, translation termination region; 3'-UTR, 3' untranslated region.

TABLE 1

ISIS 2302 P=S Isosequence Derivatives

| ISIS NO. | NUCLEOTIDE SEQUENCE (5' → 3') | SEQ ID NO: | NOTES RE: CHEMICAL MODIFICATIONS* |
|---|---|---|---|
| 2302 | GCCCAAGCTGGCATCCGTCA | 2 | |
| 9473 | GCCCAAGCTGGCATCCGTCA | 2 | fully 2'-O-methyl |
| *2'-fluoro derivatives:* | | | |
| 9941 | GCCCAAGCTGGCATCCGTCA | 2 | no m5c |
| 9952 | GCCCAAGCTGGCATCCGTCA | 2 | no m5c |
| 12604 | GCCCAAGCTGGCATCCGTCA | 2 | |
| 12605 | GCCCAAGCTGGCATCCGTCA | 2 | |
| 12606 | GCCCAAGCTGGCATCCGTCA | 2 | |
| 12607 | GCCCAAGCTGGCATCCGTCA | 2 | |
| 12608 | GCCCAAGCTGGCATCCGTCA | 2 | |
| 12609 | GCCCAAGCTGGCATCCGTCA | 2 | |
| 13371 | GCCCAAGCTGGCATCCGTCA | 2 | |
| *2'-MOE derivatives:* | | | |
| 13280 | GCCCAAGCTGGC<u>ATCCGTCA</u> | 2 | |
| 13685 | GCCCAAGCTGG<u>CATCCGTCA</u> | 2 | |
| 14725 | GCCCAAGCTGG<u>CATCCGTCA</u> | 2 | |
| 15839 | GCCCAAGCTGG<u>CATCCGTCA</u> | 2 | m5c throughout |
| 16719 | GCCCAAGCTG<u>GCATCCGTCA</u> | 2 | |
| 16720 | GCCCAAGCTGGC<u>ATCCGTCA</u> | 2 | |
| 16721 | <u>G</u>CCCAAGCTGGC<u>ATCCGTCA</u> | 2 | |
| 16722 | <u>GC</u>CCAAGCTGGC<u>ATCCGTCA</u> | 2 | |
| 14118 | <u>G</u>ACGCATCGCG<u>CCTACATCG</u> | 4 | (13685 scrambled) |
| 14391 | GACGCATCGCG<u>CCTACATCG</u> | 4 | (14725 scrambled) |

*Emboldened "C" residues, 5-methyl-cytosines (m5c), except as noted; emboldened and underlined residues, 2'-fluoro- residues; emboldened and double-underlined residues, 2'-methoxyethoxy-(MOE) residues; other residues, 2'-deoxy-, except as noted.

TABLE 2

Structures of ICAM-1 Phosphorothioate Oligonucleotides Having Sequences Related to that of ISIS 2302

| ISIS NO. | OLIGONUCLEOTIDE SEQUENCE (5' → 3') AND STRUCTURE[1] | SEQ ID NO: | GAP SIZE (bp) | TARGET GENE NUCLEOTIDE CO-ORDINATES[2] |
|---|---|---|---|---|
| 2302 | GCCCAAGCTGGCATCCGTCA | 2 | — | 2100–2119 |
| 16158 | <u>GTGCCCAAGCTGGC</u>ATCCGT | 5 | 12 | 2102–2121 |
| 16159 | <u>AGCAGTG</u>CCCAAGCTGG<u>CAT</u> | 6 | 12 | 2106–2125 |
| 16723 | <u>AGCAGTG</u>CCCAAGCTGG<u>CAT</u> | 6 | 11 | 2106–2125 |
| 16724 | <u>AGCAGTG</u>CCCAAGCTG<u>GCAT</u> | 6 | 10 | 2106–2125 |
| 16725 | <u>AGCAGTG</u>CCCAAGCTGG<u>CAT</u> | 6 | 11 | 2106–2125 |
| 16726 | <u>AGCAGTGC</u>CCAAGCTGG<u>CAT</u> | 6 | 10 | 2106–2125 |

TABLE 2-continued

Structures of ICAM-1 Phosphorothioate Oligonucleotides
Having Sequences Related to that of ISIS 2302

| ISIS NO. | OLIGONUCLEOTIDE SEQUENCE (5' → 3') AND STRUCTURE[1] | SEQ ID NO: | GAP SIZE (bp) | TARGET GENE NUCLEOTIDE CO-ORDINATES[2] |
|---|---|---|---|---|
| 16727 | AGCAGTGCCCAAGCTGGCAT | 6 | 10 | 2106–2125 |
| 16824 | CCAAGCTGGCATCCGTCA | 7 | — | 2100–2117 |
| 16823 | AAGCTGGCATCCGTCA | 8 | — | 2100–2115 |
| 16822 | GCTGGCATCCGTCA | 9 | — | 2100–2113 |
| 16821 | TGGCATCCGTCA | 10 | — | 2100–2111 |

[1]Emboldened and double-underlined residues, 2'-methoxy-ethoxy-(MOE) residues (others are 2'-deoxy-), including "C" residues, 5-methyl-cytosines (m5c).
[2]Co-ordinates from GenBank Accession No. J03132, locus name "HUMICAMA1M" (SEQ ID NO: 1).

TABLE 3

Structures of ISIS 3067 Isosequence Derivatives

| ISIS NO. | NUCLEOTIDES SEQUENCE (5'–3') AND CHEMICAL MODIFICATIONS[1] | SEQ ID NO: | COMMENTS |
|---|---|---|---|
| 3067 | TsCsTsGsAsGsTsAsGsCsAsGsAsGsGsAsGsCsTsC | 11 | target gene co-ordinates[2] 0018–0037; phosphorothioate |
| 11158 | ToCoToGoAoGoToAoGoCoAoGoAoGoGoAoGoCoToC | 11 | phosphodiester; 2'-MOE throughout except 3' residue |
| 11159 | TsCsTsGsAsGsTsAsGsCsAsGsAsGsGsAsGsCsTsC | 11 | phosphorothioate; 2'-MOE throughout except 3' residue |
| 15537 | TsCsTsGsAsGsTsAsGsCsAsGsAsGsGsAsGsCsTsC | 11 | phosphorothioate; 2'-MOE throughout |
| 12345 | GsAsTsCsGsCsGsTsCsGsGsAsCsTsAsTsGsAsAsG | 12 | scrambled control for ISIS 11159 |

[1]Emboldened and doubled-underlined residues, 2'-methoxyethoxy-residues (others are 2'-deoxy-), including "C" residues, 5-methyl-cytosines (m5c); "o", phosphodiester linkage; "s", phosphorothioate linkage.
[2]Co-ordinates from GenBank Accession No. J03132, locus name "HUMICAMA1M" (SEQ ID NO: 1).

B. Oligonucleotides Targeted to Nucleic Acids Encoding Murine ICAM-1: Tables 4 to 7 describe the nucleotide sequences and chemical structures of a set of oligonucleotides designed to specifically hybridize to murine ICAM-1-encoding nucleic acids and their corresponding ISIS and SEQ ID numbers. The nucleotide co-ordinates of the target gene and gene target regions are also included. In Table 6, the nucleotide co-ordinates are derived from EMBL accession No. X52264, locus name "MMICAM1" (SEQ ID NO: 13; see also Ballantyne et al., *Nucleic Acids Research,* 1989, 17, 5853). In Table 7, additional sequence information from the 5' end of the murine ICAM-1 mRNA is derived from GenBank accession No. M90546, locus name "MUSICAM01" (SEQ ID NO: 19; see also Ballantyne et al., *Genomics,* 1992, 14, 1076).

TABLE 4

Structure of ISIS 3082 Derivatives Having 2' Modifications Other Than 2'-Methoxyethoxy (2'-MOE)

| ISIS NO. | NUCLEOTIDE SEQUENCE (5' → 3') AND CHEMICAL STRUCTURE* | SEQ ID NO: | NOTES RE: CHEMICAL MODIFICATIONS |
|---|---|---|---|
| 3082 | TsGsCsAsTsCsCsCsCsCsAsGsGsCsSsCsAsCsCsAsT | 14 | 2'-deoxy; no m5c |

TABLE 4-continued

Structure of ISIS 3082 Derivatives Having 2' Modifications Other Than 2'-Methoxyethoxy (2'-MOE)

| ISIS NO. | NUCLEOTIDE SEQUENCE (5' → 3') AND CHEMICAL STRUCTURE* | SEQ ID NO: | NOTES RE: CHEMICAL MODIFICATIONS |
|---|---|---|---|
| | Derivatives having 2'modifications other than MOE: | | |
| 7735 | T̲oGoCoA̲oT̲oCsCsCsCsAsGsGoCoCoA̲oCoCoA̲oT | 14 | 2'-O-propyl (no 5mc) |
| 7743 | TsGsCsA̲sTsCsCsCsCsAsGsGsCsCsA̲sCsCsA̲sT | 14 | 2'-O-methyl (no 5mc) |
| 7744 | TsGsCsA̲sTsCsCsCsCsCsAsGsGsCsCsA̲sCsCsA̲sT | 14 | 2'-O-methyl (no 5mc) |
| 7753 | T̲oGoCoA̲oT̲oCoCoCoCsCsAsGsGsCsCsAoCoCoA̲oT | 14 | 2'-O-propyl (no 5mc) |
| 8567 | TsGsCsAsTsCsCsCsCsCsAsGsGsCsCsAsCsCsAsT | 14 | 2'-fluoro (no 5mc) |
| 8568 | TsGsCsAsTsCsCsCsCsCsAsGsGsCsCsAsCsCsAsT | 14 | 2'-fluoro (no 5mc) |

*Emboldened underlined residues, indicated 2' modifications (others are 2'-deoxy-); emboldened "C" residues, 5-methyl-cytosines (m5c); "o", phosphodiester linkage; "s", phosphorothioate linkage.

TABLE 5

Structures of ISIS 3082 2'-Methoxyethoxy Modified Derivatives

| ISIS NO. | NUCLEOTIDE SEQUENCE (5' → 3') AND CHEMICAL STRUCTURE* | SEQ ID NO: | NOTES RE: CHEMICAL MODIFICATIONS |
|---|---|---|---|
| 3082 | TsGsCsAsTsCsCsCsCsCsAsGsGsGsCsCsAsCsCsAsT | 14 | 2'-deoxy; no 5mc |
| 12471 | T̲oGoCoA̲oT̲oCoCsCsCsCsAsGsGsGsCsCoA̲oCoCoA̲oT | 14 | mixed backbone |
| 13315 | TsGsCsA̲sTsCsCsCsCsCsAsGsGsGsCsCsAsCsCsA̲sT | 14 | |
| 13316 | TsGsCsA̲sTsCsCsCsCsCsAsGsGsGsCsCsAsCsCsA̲sT | 14 | |
| 13317 | TsGsCsAsTsCsCsCsCsCsAsGsGsGsCsCsA̲sCsCsA̲sT | 14 | |
| 13318 | TsGsCsAsTsCsCsCsCsCsA̲sGsGsCsCsA̲sCsCsA̲sT | 14 | |
| 13814 | T̲oGoCoA̲oT̲oCoCoCsCsCsAsGsGsGsCsCsAsCsCsA̲sT̲ | 14 | mixed backbone |
| 13815 | TsGsCsA̲sTsCsCsCsCsCsAsGsGsGsCsCsAsCsCsA̲sT̲ | 14 | |
| 13816 | T̲oGoCoA̲oT̲oCoCoCsCsCsAsGsGsGsCsCsAsCoCoA̲oT̲ | 14 | mixed backbone |
| 16716 | TsGsCsA̲sTsCsCsCsCsCsAsGsGsGsCsCsAsCsCsAsT | 14 | |
| 16718 | TsGsCsA̲sTsCsCsCsCsCsAsGsGsGsCsCsAsCsCsA̲sT̲ | 14 | |
| 16825 | CsCsCsCsAsGsGsGsCsCsAsCsCsA̲sTsCsCsT̲sGsTsT̲ | 15 | |
| 14153 | T̲sCsGsCsA̲sTsCsGsAsCsCsCsGsCsCsCsAsCsT̲sA̲ | 16 | 3082 scrambled |

*Emboldened and double-underlined residues, 2'-methoxyethoxy- residues (others are 2'-deoxy-); emboldened "C" residues, 5-methyl-cytosines (m5c); "o", phosphodiester linkage; "s", phosphorothioate linkage.

TABLE 6

Structures of Active 2'-MOE Hemimer Targeted to the 3'-UTR of Murine ICAM-1 and Control Oligonucleotides

| ISIS NO. | NUCLEOTIDE SEQUENCE (5' → 3') | SEQ ID NO: | TARGET GENE NUCLEOTIDE CO-ORDINATES[1] | GENE TARGET REGION |
|---|---|---|---|---|
| 17481 | TCCCACAGCAGC<u>TTGCACGA</u> | 3 | 2421–2440[2] | 3'-UTR |
| 20438 | ATCCCGACTGAC<u>AGACGTCC</u> | 26 | 17481 scrambled control | — |
| 20439 | TTCCCCAGCAGC<u>ATGCACGA</u> * * * | 27 | 17481 3 base mismatch (*) control | — |
| 20440 | TCCGACAGCACC<u>TTGCACGA</u> * * | 28 | 17481 2 base mismatch (*) control | — |
| 20441 | TCCCTCAGCAGC<u>TTGCACGA</u> * | 29 | 17481 1 base mismatch (*) control | — |

[1] Emboldened and double-underlined residues, 2'-methoxyethoxy-residues (others are 2'-deoxy-); all "C" and "C " residues, 5-methyl-cytosines.
[2] Co-ordinates from EMBL Accession No. X52264, locus name "MMICAM1" (SEQ ID NO: 13).

TABLE 7

Structures of Mouse ICAM-1 5'-UTR-Targeted Phosphorothioate Oligonucleotides

| ISIS NO. | NUCLEOTIDES SEQUENCE (5' → 3') AND CHEMICAL MODIFICATIONS[1] | SEQ ID NO: | TARGET GENE NUCLEOTIDE CO-ORDINATES[2] | GENE TARGET REGION |
|---|---|---|---|---|
| 12472 | TsGsCsAsGsGsTsAsGsCsAsGsCsGsGsAsGsCsTsC | 20 | 0643–0622 | 5'-UTR |
| 14282 | GsAsAsGsCsCsAsTsTsGsCsAsGsGsGsCsCsAsGsG | 21 | 0669–0668 | 5'-UTR |
| 15163 | GoGoAoGoCoToCoAoGoCoAoCoToAoGoCoAoCoToG | 22 | 0630–0649 | 5'-UTR |
| 15164 | GsGsAsGsCsTsCsAsGsCsAsCsTsAsGsCsAsCsTsG | 22 | 0630–0649 | 5'-UTR |
| 15699 | GsCsCsAsGsGsGsCsAsAsAsGsTsGsCsAsGsGsTsA | 23 | 0655–0674 | 5'-UTR |
| 15722 | GsCsGsCsTsTsTsTsAsTsAsGsTsCsTsCsTsGsGsC | 24 | 0590–0609 | 5'-UTR |
| 15724 | GsGsTsGsCsAsGsAsCsTsGsAsGsGsCsGsGsGsCsG | 25 | 0610–0629 | 5'-UTR |

[1]Emboldened and underlined residues, 2'-fluoro- residues; emboldened and double-underlined residues, 2'-methoxyethoxy- residues (others are 2'-deoxy-); all emboldened "C" and "C" residues, 5-methyl-cytosines (m5c); "o", phosphodiester linkage; "s", phosphorothioate linkage.
[2]Co-ordinates from GenBank Accession No. M90546, locus name "MUSICAM01" (SEQ ID NO: 19).

Example 3

Assays for oligonucleotide-Mediated Inhibition of mRNA Expression in Human and Murine Cell Lines A. General Techniques 1. Cell Lines: In order to evaluate the activity of potential human ICAM-1-modulating oligonucleotides, human umbilical vein endothelial cells (HUVECs or HUVEC cells) from Clonetics Corporation (Walkersville, Md.; alternatively, ATCC CRL-1730 from the American Type Culture Collection, Rockville, Md., can be used) were grown and treated with oligonucleotides or control solutions as detailed below. For oligonucleotides targeting the murine ICAM-1 gene, oligonucleotide-treated cells were of the bEND.3 endothelial cell line (gift of Dr. Werner Risau; see Montesano et al., Cell, 1990, 62, 435, and Stepkowski et al., J. Immunol., 1994, 153, 5336). After harvesting, cellular extracts were prepared and examined for specific ICAM-1-encoding mRNA levels or ICAM-1 protein levels (e.g., Northern or flow cytometry assays, respectively). In all cases, "% expression" refers to the amount of ICAM-1-specific signal in an oligonucleotide-treated cell relative to an untreated cell (or a cell treated with a control solution that lacks oligonucleotide), and "% inhibition" is calculated as 100% −Expression=% Inhibition.

2. Treatment of Cells with Oligonucleotides: HUVEC (human) or bEND.3 (murine) cells were grown in, respectively, EGM (Clonetics, Walkersville, Md.) or high-glucose DMEM (GIBCO-BRL Life Technologies, Gaithersburg, Md.) medium containing 10% fetal bovine serum (FBS) in T-75 flasks until 80–90% confluent. At this time, the cells were washed 3× with 10 mL of Opti-MEM media (GIBCO-BRL). Then, 5 mL of Opti-MEM medium containing 10 (HUVEC) or 15 (bEND.3) ug/mL LIPOFEC-TIN® (i.e., 1:1 (w/w) DOTMA/DOPE, where DOTMA=N-[1-(2,3-dioleyoxy)propyl]-N,N,N-trimethylammonium chloride and DOPE=dioleoyl phosphatidylethanolamine; GIBCO-BRL) and an appropriate amount of oligonucleotide were added to the cells (the time of addition of oligonucleotide is t=0 h in the experiments described herein). As a control, cells were treated with LIPOFECTIN® without oligonucleotide under the same conditions and for the same times as the oligonucleotide-treated samples.

After 4 hours at 37° C. (t=4 h), the medium was replaced with fresh EGM (HUVEC) or high glucose DMEM (bEND.3) medium containing 10% FBS and one or more cytokines to induce ICAM-1 expression. For HUVECs, induction of ICAM-1 was achieved by adding 5 ng/mL of human tumor necrosis factor alpha (TNF-a; R&D Systems, Inc., Minneapolis, Minn.). In experiments using bEND.3 cells, murine ICAM-1 was induced by adding 5 ng/mL of human tumor necrosis factor alpha (TNF-a; R&D Systems, Inc., Minneapolis, Minn.) and 200 u/mL of mouse interferon-gamma (IFN-g; R&D Systems) to the medium at the same time the cells were treated with oligonucleotides. The cells were typically allowed to recover overnight (about 18 to 24 hours) before RNA and/or protein assays were performed.

B. RNA Assays: Total cellular RNA was then extracted in guanidinium, subjected to gel electrophoresis and transferred to a filter according to techniques known in the art (see, e.g., Chapter 7 In: Molecular Cloning: A Laboratory Manual, 2nd Ed., Sambrook et al., eds., pages 7.1–7.87, and Short Protocols in Molecular Biology, 2nd Ed., Ausubel et al., eds., John Wiley & Sons, New York, 1992, pages 2-24 to 2-30 and 4-14 to 4-29).

Following RNA transfer, filters were typically hybridized overnight to a probe specific for the particular ICAM-1-encoding gene of interest in hybridization buffer (QUIKHYB™ hybridization solution, Stratagene, La Jolla, Calif.). This was followed by two washes in 2×SSC, 0.1% SDS at room temperature (~24EC) for 15 m and one wash in 0.1×SSC, 0.1 SDS at 60EC for 30 m. Hybridizing bands were visualized by exposure to X-OMAT AR film and quantitated using a PHOSPHORIMAGER® essentially according to the manufacturer's instructions (Molecular Dynamics, Sunnyvale, Calif.). Although quantitation via a PHOSPHORIMAGER® or a comparable instrument is a preferred means of measuring RNA levels, the results of these "Northern" assays could be determined by other means known in the art.

C. Protein Assays: HUVEC or bEND.3 cells were grown in 12 well plates and treated with oligonucleotides as described above, except that cells were generally allowed to recover overnight (e.g., generally about 18 hours) before protein extracts were prepared. Cells were washed and released by treatment with trypsin (GIBCO-BRL) or EDTA. Specifically, HUVEC cells were typically released by trypsin treatment, although EDTA treatment worked as well, whereas bEND.3 cells are preferentially released by treatment with 2 mM EDTA in $Ca^{++}$- and $Mg^{++}$-free 1× PBS buffer (HBSS; GIBCO-BRL). Cells were stained with an appropriate fluorescently labeled primary antibody that specifically recognizes the ICAM-1 protein under examination and the amount of each ICAM-1 protein was determined by using fluorescence-activated cell sorting (FACS®) techniques (see, e.g., U.S. Pat. No. 4,727,020 to Recktenwald, U.S. Pat. No. 5,223,398 to Kortright et al., and U.S. Pat. No. 5,556,764 to Sizto et al.). The fluorescently labeled primary antibodies specific for each ICAM-1 protein are described in the appropriate Examples. Alternatively, unlabeled primary antibodies to ICAM-1 can be used and detected by the use of fluorescently-labeled secondary (i.e., specific for the primary antibody) antibodies.

In alternative methods for measuring ICAM-1 levels, cell lysates and protein extracts are electrophoresed (SDS-PAGE), transferred to nitrocellulose filters and detected by means known in the art (see, e.g., Chapter 18 *In: Molecular Cloning: A Laboratory Manual,* 2nd Ed., Sambrook et al., eds., pages 18.34, 18.47–18.54 and 18.60–18.75)). Unlabeled primary antibodies to ICAM-1 can be used and detected by means well known in the art including, for example, detection of the primary antibody by a secondary antibody that binds the primary antibody (see, e.g., *Short Protocols in Molecular Biology,* 2nd Ed., Ausubel et al., eds., John Wiley & Sons, New York, 1992, pages 10-33 to 10-35; and Chapter 18 *In: Molecular Cloning: A Laboratory Manual,* 2nd Ed., Sambrook et al., eds., pages 18.1–18.75 and 18.86–18.88) and quantitated using other antibody-based assays known in the art. Such antibody-based assays include, but are not limited to, ELISA assays, Western assays, and the like (see, for example, U.S. Pat. No. 4,879,219 to Wands et al. and U.S. Pat. No. 4,837,167 to Schoemaker et al., and *Short Protocols in Molecular Biology,* 2nd Ed., Ausubel et al., eds., John Wiley & Sons, New York, 1992, pages 11-5 to 11-17).

ICAM-1 activity can be measured in appropriate cell adhesion assays known in the art. See, for example, Example 11 in U.S. Pat. No. 5,514,788 to Bennett et al.

Example 4

Optimization of Chemistry of ISIS 2302 Derivatives

One strategy for optimizing an antisense lead compound involves retaining the nucleobase sequence thereof while altering and/or adding to the chemical modifications present in the lead compound. In this Example, various chemical modifications are made to a lead antisense compound targeted to human ICAM-1, ISIS 2302. Compounds were evaluated via FACS® using monoclonal antibodies to human ICAM-1 conjugated to phycoerythrin (PE) from Becton-Dickinson (Franklin Lakes, N.J.).

A. Isosequence Compound Design: ISIS 2302 is a phosphorothioate oligonucleotide comprising, as a nucleobase sequence that specifically hybridizes to nucleic acids encoding ICAM-1, 5'-GCCCAAGCTGGCATCCGTCA (SEQ ID NO: 2). Isosequence derivatives of ISIS 2302 include ISIS 9473, in which every residue has a 2'-O-methyl modification. Because fully 2'-O-methyl modified oligonucleotides do not support RNase H activity on RNA substrates to which they hybridize, they can be used to determine the extent to which RNase H is required for an antisense-mediated effect (Chiang et al., *J. Biol. Chem.,* 1991, 266, 18162).

Other isosequence derivatives of ISIS 2302 include those having 2'-fluoro modifications, i.e., ISIS 9941, 9952, 12604, 12605, 12606, 12607, 12608, 12609 and 13371 (see Table 1, wherein 2'-fluoro-modified residues are underlined). Fully 2'-fluoro-modified oligonucleotides, like fully 2'-O-methyl modified oligonucleotides, are incapable of activating RNase H. However, a chimeric 2'-fluoro-modified oligonucleotide may support RNase H against a target RNA in regions thereof hybridizing to a non-2'-modified portion of the chimeric oligonucleotide. Such chimeric compounds include so-called "hemimers" or "wingmers," i.e., oligonucleotides in which one or other of the 5' or 3' termini comprises a stretch of 2'-modified residues (e.g., ISIS 12604, 12605, 12606, 12607 and 13371). Chimeric compounds further include "gapmers," i.e., compounds in both the 5' and 3' termini comprise stretches of modified (e.g., ISIS 12608 and 12609) or unmodified (e.g., ISIS 9941 and 9952) residues.

Another set of isosequence derivatives of ISIS 2302 include chimeric compounds having 2'-methoxyethoxy (2'-MOE) modifications, i.e., ISIS 13280, 13685, 14725, 15839, 16719, 16720, 16721 and 16722 (see Table 1, wherein 2'-MOE-modified residues are emboldened). As with the 2'-fluoro-modified derivatives, the 2'-MOE-modified derivatives of ISIS 2302 include "hemimers" (e.g., ISIS 13280, 14725, 15839, 16719 and 16720) and "gapmers" (e.g., ISIS 13685, 16721 and 16722).

In both of the above sets of isosequence derivatives of ISIS 2302, 5-methyl cytosine (m5c) residues are present instead of unmodified cytosine residues in most or all of the 2'-modified portion(s) thereof. Furthermore, ISIS 15839 has C to m5c substitutions throughout.

B. Activities of Isosequence Compounds: In an initial screen for activity, the isosequence derivatives of ISIS 2302 described in Table 1 were tested via FACS® for their ability to reduce ICAM-1 protein levels on HUVECs. The results demonstrate that ISIS 13371 was as active as, and ISIS 12604, 13280, 14725 and 15389 were more active than, ISIS 2302 in this assay. These compounds are thus preferred embodiments of the invention.

The preferred ISIS 2302 isosequence derivatives exhibit more potent dose responses relative to the parent compound. Specifically, as shown in Table 8, ISIS 13280 (which has 2'-methoxyethoxy-modifications at 7 out of 8 of its 3'-most residues) caused about 50% reduction in ICAM-1 protein levels at a dose of 6.25 nM, whereas parent compound ISIS 2302 caused only about 15% inhibition at this dose. At 25 nM, ISIS 13280 caused about 75% inhibition of ICAM-1 expression, whereas the parent compound did not achieve about 75% inhibition until a dose of 100 nM was reached. On the other hand, ISIS 13685, a 2302-based gapmer having the 5'-most, and seven out of eight of the 3'-most, 2'-methoxyethoxy-modified residues, exhibited a poor dose response relative to ISIS 2302 in this set of experiments. Due to its potency, ISIS 13280 is a preferred embodiment of the invention.

The ability to synthesize oligonucleotides wherein the 3'-most residue is 2-methoxyethoxy-modified, and wherein 5-methyl cytosine (m5c) is substituted for cytosine, allowed for further derivatives of ISIS 13280 to be made and tested. As shown in Table 9, ISIS 2302/13280 isosequence derivatives ISIS 14725 and ISIS 15389 inhibit ICAM-1 protein expression in cultured HUVECs to a greater degree for a longer period of time than the parent compound. Specifically, ISIS 2302 caused about 35% inhibition of ICAM-1 protein levels at t=48 h, whereas ISIS 14725 and ISIS 15389 (both compounds are hemimers wherein the eight 3'-most residues are 2'-methoxyethoxy-modified) caused over about 50% inhibition at the same point in time (wherein "about" signifies ±5%). ISIS 14725 and 13280 show enhanced modulation of ICAM-1 relative to the parent compound (ISIS 2302) and are thus preferred embodiments of the invention. ISIS 15389, which has 5-methyl cytosine (m5c) substituted for cytosine throughout its nucleobase sequence, caused about 60% inhibition of ICAM-1 at t=48 h and is therefore most preferred.

The specificity of the 2'-methoxyethoxy hemimers was confirmed by the fact that ISIS 14118, a scrambled control for ISIS 13685, caused only about 18% inhibition of ICAM-1 even at a dose of 100 nM (Table 8). Similarly, ISIS 14391, a 2'-methoxyethoxy hemimer having a scrambled version of the nucleobase sequence of ISIS 14725, caused only about 16% inhibition of ICAM-1 at t=48 h at a dose of 100 nM (Table 9).

The isosequence derivatives described in this Example also exhibit improved dose responses relative to the parent compound. Specifically, as shown in Table 10, ISIS 14725 causes over 50% inhibition of ICAM-1 in HUVECs at a dose of 6.25 nM compared to about 45% inhibition by ISIS 2302 at a dose of 12.5 nM.

TABLE 8

Dose Response of HUVEC Cells to ISIS 2302 Derivatives[1]

| ISIS # | SEQ ID NO: | ASO Gene Target | Dose | % Protein Expression | % Protein Inhibition |
|---|---|---|---|---|---|
| basal | — | LIPOFECTIN ® only | 0 nM | 100.0% | 0.0% |
| 2302 | 2 | 3'-UTR | 6.25 nM | 86.6% | 13.4% |
| 2302 | 2 | " | 12.5 nM | 77.3% | 22.7% |
| 2302 | 2 | " | 25 nM | 59.8% | 40.2% |
| 2302 | 2 | " | 50 nM | 34.0% | 66.0% |
| 2302 | 2 | " | 100 nM | 25.7% | 74.3% |
| 13280 | 2 | 3'-UTR | 6.25 nM | 49.8% | 50.2% |
| 13280 | 2 | " | 12.5 nM | 36.0% | 64.0% |
| 13280 | 2 | " | 25 nM | 22.6% | 77.4% |
| 13280 | 2 | " | 50 nM | 12.0% | 88.0% |
| 13280 | 2 | " | 100 nM | 10.4% | 89.6% |
| 13685 | 2 | 3'-UTR | 6.25 nM | 97.4% | 2.6% |
| 13685 | 2 | " | 12.5 nM | 90.7% | 9.3% |
| 13685 | 2 | " | 25 nM | 86.2% | 13.8% |
| 13685 | 2 | " | 50 nM | 74.1% | 25.9% |
| 13685 | 2 | " | 100 nM | 57.2% | 42.8% |
| 14118 | 4 | 2302 scrambled | 6.25 nM | 95.0% | 5.0% |
| 14118 | 4 | " | 12.5 nM | 100.2% | — |
| 14118 | 4 | " | 25 nM | 92.7% | 7.3% |
| 14118 | 4 | " | 50 nM | 95.1% | 4.9% |
| 14118 | 4 | " | 100 nM | 82.1% | 17.9% |

[1]After overnight incubation (t~18 h).

TABLE 9

Time Course of Response of HUVEC Cells to ISIS 2302 Derivatives[1]

| ISIS # | SEQ ID NO: | Intragenic Target Region | Time | % Protein Expression[2] | % Protein Inhibition |
|---|---|---|---|---|---|
| basal | — | LIPOFECTIN ® only | 24 h | 100.0% | 0.0% |
| basal | — | LIPOFECTIN ® only | 48 h | 100.0% | 0.0% |
| basal | — | LIPOFECTIN ® only | 72 h | 100.0% | 0.0% |
| 2302 | 2 | 3'-UTR | 24 h | 8.9% | 91.1% |
| 2302 | 2 | " | 48 h | 64.3% | 35.7% |
| 2302 | 2 | " | 72 h | 167.8% | — |
| 14725 | 2 | 3'-UTR | 24 h | 10.1% | 89.9% |
| 14725 | 2 | " | 48 h | 49.9% | 50.1% |
| 14725 | 2 | " | 72 h | 104.6% | — |
| 15839 | 2 | 3'-UTR | 24 h | 13.1% | 86.9% |
| 15839 | 2 | " | 48 h | 40.8% | 59.2% |

TABLE 9-continued

Time Course of Response of HUVEC Cells to ISIS 2302 Derivatives[1]

| ISIS # | SEQ ID NO: | Intragenic Target Region | Time | % Protein Expression[2] | % Protein Inhibition |
|---|---|---|---|---|---|
| 15839 | 2 | " | 72 h | 104.1% | — |
| 14391 | 4 | 2302 scrambled | 24 h | 113.4% | — |
| 14391 | 4 | " | 48 h | 84.1% | 15.9% |
| 14391 | 4 | " | 72 h | 123.2% | — |

[1]HUVEC cells treated with 100 nM (final concentration) of indicated oligonucleotides.
[2]Derived from three samples.

Example 5

Optimization of Sequence of ISIS 2302 Derivatives

Another strategy for optimizing an antisense lead compound involves modifying the nucleobase sequence thereof while retaining a common chemical motif. In this Example, various sequence modifications are made to a lead antisense compound targeted to human ICAM-1, ISIS 2302, using a common chimeric m5c/2'-MOE motif.

A. Design of Compounds Having Sequences Related to that of ISIS 2302: ISIS 2302 is a phosphorothioate oligonucleotide comprising, as a nucleobase sequence that specifically hybridizes to nucleic acids encoding ICAM-1, 5'-GCCCAAGCTGGCATCCGTCA (SEQ ID NO: 2). In order to determine if additional activity could be gained by "adjusting" the sequence of ISIS 2302 within a constant chemical motif, a series of related compounds were designed and synthesized (Table 2).

As is shown in Table 2, ISIS 16159 and 16723–16727 are 2'-methoxyethoxy (2'-MOE) gapmers having a common sequence (SEQ ID NO: 6) that is shifted, relative to ISIS 2302, 6 bases in the 3' direction on the target gene sequence. Similarly, ISIS 16158 is a 2'-MOE gapmer that has a sequence that is shifted, relative to ISIS 2302, 2 bases in the 3' direction on the target gene sequence. The preceding compounds all have nucleobase sequences of 20 bases; in order to investigate the effectiveness of a series of progressively smaller compounds, ISIS 16284 (18 bases), 16823 (16 bases), 16822 (14 bases) and 16281 (12 bases) were designed and synthesized.

B. Activities of Compounds Having Sequences Related to that of ISIS 2302: Relative to their parent compound ISIS 2302, ISIS 16158 and 16159 have more potent dose responses (Table 10). Specifically, ISIS 16158 and 16159 caused about 50 to 55% inhibition of ICAM-1 at a dose of 6.25 nM compared to about 45 inhibition by ISIS 2302 at a dose of 12.5 nM. ISIS 16158 and 16159 are thus preferred embodiments of the invention.

TABLE 10

Dose Response of HUVEC Cells to ISIS 2302 Derivatives[1]

| ISIS # | SEQ ID NO: | Intragenic Target | Dose | % Protein Expression | % Protein Inhibition |
|---|---|---|---|---|---|
| basal | — | LIPOFECTIN ® only | 0 nM | 0.0% | 100.0% |
| induced[2] | — | | 0 nM | 100.0% | 0.0% |

TABLE 10-continued

Dose Response of HUVEC Cells to ISIS 2302 Derivatives[1]

| ISIS # | SEQ ID NO: | Intragenic Target | Dose | % Protein Expression | % Protein Inhibition |
|---|---|---|---|---|---|
| 2302 | 2 | 3'-UTR | 6.25 nM | 72.5% | 27.5% |
| 2302 | 2 | " | 12.5 nM | 55.2% | 44.8% |
| 2302 | 2 | " | 25 nM | 20.9% | 79.1% |
| 2302 | 2 | " | 50 nM | 7.4% | 92.6% |
| 2302 | 2 | " | 100 nM | 1.5% | 98.5% |
| 14725 | 2 | 3'-UTR | 6.25 nM | 49.0% | 51.0% |
| 14725 | 2 | " | 12.5 nM | 38.9% | 61.1% |
| 14725 | 2 | " | 25 nM | 18.0% | 72.0% |
| 14725 | 2 | " | 50 nM | 9.9% | 90.1% |
| 14725 | 2 | " | 100 nM | 0.2% | 99.8% |
| 16158 | 5 | 3'-UTR | 6.25 nM | 48.2% | 51.8% |
| 16158 | 5 | " | 12.5 nM | 30.2% | 69.8% |
| 16158 | 5 | " | 25 nM | 12.1% | 87.9% |
| 16158 | 5 | " | 50 nM | 3.8% | 96.2% |
| 16158 | 5 | " | 100 nM | 3.6% | 96.4% |
| 16159 | 6 | 3'-UTR | 6.25 nM | 46.9% | 53.1% |
| 16159 | 6 | " | 12.5 nM | 27.1% | 72.9% |
| 16159 | 6 | " | 25 nM | 11.3% | 88.7% |
| 16159 | 6 | " | 50 nM | 4.0% | 96.0% |
| 16159 | 6 | " | 100 nM | -7.4% | 100.0% |

[1]After overnight incubation (t~18 h).
[2]For details of induction, see the Examples.

ISIS 16281–16284, shortened derivatives of ISIS 2302 were also evaluated for their activity. As is shown in Table 11, ISIS 16284 (18 bases) and ISIS 16283 (16 bases) are about as effective as ISIS 2302 in inhibiting ICAM-1 expression. For example, at a dose of 100 nM, ISIS 16284 caused about 55% inhibition, and ISIS 16283 caused about 45% inhibition, compared to about 60% inhibition by ISIS 2302 at this dose. ISIS 16284 and 16283 are thus preferred embodiments of the invention. Shorter derivatives of ISIS 2302 (ISIS 16822, 14 bases, and ISIS 16281, 12 bases) showed little or non-specific activity in these assays. The specificity of the active compounds was confirmed by the fact that ISIS 14391, a scrambled control for ISIS 14725, caused only about 20% inhibition of ICAM-1 even at a dose of 100 nM.

TABLE 11

Activity of ISIS 2302 "Shortmers" Derivative Antisense Oligonucleotides (ASOs) in HUVECs[1]

| ISIS # | SEQ ID NO: | ICAM-1 Intragenic Target (and No. of bases in ASO) | Dose | % Protein Expression | % Protein Inhibition |
|---|---|---|---|---|---|
| basal | — | LIPOFECTIN ® only | 0 nM | 100.0% | 0.0% |
| 2302 | 2 | 3'-UTR (20 bases) | 12.5 nM | 53.5% | 46.5% |
| 2302 | 2 | " | 25 nM | 50.2% | 49.8% |
| 2302 | 2 | " | 50 nM | 48.6% | 51.4% |
| 2302 | 2 | " | 100 nM | 37.5% | 62.5% |
| 14725 | 2 | 3'-UTR (20 bases) | 12.5 nM | 48.0% | 52.0% |
| 14725 | 2 | " | 25 nM | 46.0% | 54.0% |
| 14725 | 2 | " | 50 nM | 43.0% | 57.0% |
| 14725 | 2 | " | 100 nM | 25.0% | 75.0% |
| 14391 | 4 | scrambled control | 12.5 nM | 120.0% | — |
| 14391 | 4 | " | 25 nM | 96.0% | 4.0% |
| 14391 | 4 | " | 50 nM | 92.0% | 8.0% |
| 14391 | 4 | " | 100 nM | 80.0% | 20.0% |
| 16824 | 7 | 3'-UTR (18 bases) | 12.5 nM | 86.0% | 14.0% |
| 16824 | 7 | " | 25 nM | 75.0% | 25.0% |
| 16824 | 7 | " | 50 nM | 60.0% | 40.0% |
| 16824 | 7 | " | 100 nM | 45.0% | 55.0% |
| 16823 | 8 | 3'-UTR (16 bases) | 12.5 nM | 96.0% | 4.0% |
| 16823 | 8 | " | 25 nM | 73.0% | 27.0% |
| 16823 | 8 | " | 50 nM | 70.0% | 30.0% |
| 16823 | 8 | " | 100 nM | 55.0% | 45.0% |
| 16822 | 9 | 3'-UTR (14 bases) | 12.5 nM | 99.0% | 1.0% |
| 16822 | 9 | " | 25 nM | 96.0% | 4.0% |
| 16822 | 9 | " | 50 nM | 87.0% | 13.0% |
| 16822 | 9 | " | 100 nM | 86.0% | 14.0% |
| 16281 | 10 | 3'-UTR (12 bases) | 12.5 nM | 85.0% | 15.0% |
| 16281 | 10 | " | 25 nM | 95.0% | 5.0% |
| 16281 | 10 | " | 50 nM | 93.5% | 6.5% |
| 16281 | 10 | " | 100 nM | 110.0% | — |

[1]After overnight incubation (t~18 h).

Example 6

Optimization of Chemistry of ISIS 3067 Derivatives

One strategy for optimizing an antisense lead compound involves retaining the nucleobase sequence thereof while altering and/or adding to the chemical modifications present in the lead compound. In this Example, various chemical modifications are made to a lead antisense compound targeted to human ICAM-1, ISIS 3067.

A. Isosequence Compound Design: ISIS 3067 (SEQ ID NO: 11) is a phosphorothioate oligonucleotide having a nucleobase sequence that specifically hybridizes to bases 18–37 of the human ICAM-1 cDNA (SEQ ID NO: 1). Chiang et al. (*J. Biol. Chem.*, 1991, 266, 18162) demonstrated that the activity of ISIS 1570, which hybridizes nearby (i.e., to bases 50–70 of SEQ ID NO: 1), was reduced about threefold (but not abolished) in an isosequence derivative (ISIS 2974) that is fully 2'-O-methyl modified.

The results of Chiang et al. indicate that at least part of the activities of antisense compounds targeted to this portion of the human ICAM-1 mRNA is due to functions other than RNase H. Accordingly, isosequence derivatives of ISIS 3067 were prepared that were fully (or mostly so) 2'-MOE modified (Table 3). Different linkages were included in the set of candidate second generation compounds, i.e., phosphodiester bonds are present in ISIS 11158, whereas phosphorothioate bonds are used in ISIS 11159 and 15537. In all of the isosequence derivatives of ISIS 3067, another chemical variable that is uniformly present (or nearly so) is the presence of 5-methyl cytosine (m5c) residues instead of unmodified cytosines.

B. Activities of Isosequence Compounds: ISIS 3067 isosequence derivatives exhibit more potent dose responses relative to the parent compound. Specifically, as shown in Table 11, ISIS 11158 (phosphodiester linkages; 2'-MOE throughout except for the 3'-most residue) caused about 75% reduction in ICAM-1 protein levels at a dose (concentration) of 6.25 nM; ISIS 11159 (phosphorothioate linkages; 2'-MOE throughout except for the 3'-most residue) caused about 75% inhibition at a dose of 12.5 nM; and, in these experiments, parent compound ISIS 3067 caused about 75% inhibition only at a concentration of 100 nM.

The ISIS 3067 isosequence derivatives also inhibit ICAM-1 protein expression in cultured HUVECs to a greater degree for a longer period of time than the parent compound (Table 12). Specifically, ISIS 3067, 11158, 11159 and 15537 caused about 85% to 90% inhibition at t=24 h;

however, at t=48 h, ISIS 3067 caused only about 30% inhibition of ICAM-1, whereas ISIS caused about 65% inhibition, and ISIS 11158 and 15537 caused about 75% inhibition, of ICAM-1 at the same point in time. ISIS 11158, 11159 and 15537 are preferred embodiments of the invention, with ISIS 5537 being most preferred.

The specificity of the ISIS 3067 derivatives was confirmed by the fact that ISIS 12345, a scrambled control for ISIS 11159, caused only about 12% inhibition of ICAM-1 at a dose of 100 nM at t=48 h (Table 12).

TABLE 12

Dose Response of HUVEC Cells to ISIS 3067 Derivatives[1]

| ISIS # | SEQ ID NO: | ASO Gene Target | Dose | % Protein Expression | % Protein Inhibition |
|---|---|---|---|---|---|
| basal | — | LIPOFECTIN ® only | 0 nM | 100.0% | 0.0% |
| 3067 | 11 | 5'-UTR | 6.25 nM | 81.1% | 18.9% |
| 3067 | 11 | " | 12.5 nM | 70.6% | 29.4% |
| 3067 | 11 | " | 25 nM | 53.8% | 46.2% |
| 3067 | 11 | " | 50 nM | 39.1% | 60.9% |
| 3067 | 11 | " | 100 nM | 24.3% | 75.7% |
| 11158 | 11 | 5'-UTR | 6.25 nM | 25.6% | 74.4% |
| 11158 | 11 | " | 12.5 nM | 21.9% | 78.1% |
| 11158 | 11 | " | 25 nM | 11.8% | 88.2% |
| 11158 | 11 | " | 50 nM | 4.9% | 95.1% |
| 11158 | 11 | " | 100 nM | 2.4% | 97.6% |
| 11159 | 11 | 5'-UTR | 6.25 nM | 52.4% | 47.6% |
| 11159 | 11 | " | 12.5 nM | 25.7% | 74.3% |
| 11159 | 11 | " | 25 nM | 13.5% | 86.5% |
| 11159 | 11 | " | 50 nM | 8.4% | 91.6% |
| 11159 | 11 | " | 100 nM | 4.1% | 95.9% |
| 14118 | 4 | 2302 scrambled | 6.25 nM | 95.0% | 5.0% |
| 14118 | 4 | " | 12.5 nM | 100.2% | — |
| 14118 | 4 | " | 25 nM | 92.7% | 7.3% |
| 14118 | 4 | " | 50 nM | 95.1% | 4.9% |
| 14118 | 4 | " | 100 nM | 82.1% | 17.9% |

[1]After overnight incubation (t~18 h).

TABLE 13

Time Course of Response of HUVEC Cells to ISIS 3067 Derivatives[1]

| ISIS # | SEQ ID NO: | ASO Gene Target Region | Time | % Protein Expression[2] | % Protein Inhibition |
|---|---|---|---|---|---|
| basal | — | LIPOFECTIN ® only | 24 h | 100.0% | 0.0% |
| basal | — | LIPOFECTIN ® only | 48 h | 100.0% | 0.0% |
| basal | — | LIPOFECTIN ® only | 72 h | 100.0% | 0.0% |
| 3067 | 11 | 5'-UTR | 24 h | 14.5% | 85.5% |
| 3067 | 11 | " | 48 h | 71.7% | 28.3% |
| 3067 | 11 | " | 72 h | 174.6% | — |
| 11158 | 11 | 5'-UTR | 24 h | 15.4% | 84.6% |
| 11158 | 11 | " | 48 h | 27.0% | 73.0% |
| 11158 | 11 | " | 72 h | 106.1% | — |
| 11159 | 11 | 5'-UTR | 24 h | 11.7% | 88.3% |
| 11159 | 11 | " | 48 h | 32.6% | 67.4% |
| 11159 | 11 | " | 72 h | 105.0% | — |
| 15537 | 11 | 5'-UTR | 24 h | 7.6% | 92.4% |
| 15537 | 11 | " | 48 h | 24.8% | 75.2% |
| 15537 | 11 | " | 72 h | 96.9% | 3.1% |
| 12345 | 12 | 11159 scrambled | 24 h | 149.6% | — |
| 12345 | 12 | " | 48 h | 88.4% | 11.6% |
| 12345 | 12 | " | 72 h | 210.2% | — |

[1]HUVEC cells treated with 100 nM (final concentration) of indicated oligonucleotides.
[2]Derived from three samples.

Example 7

5'-UTR-Targeted Murine ICAM-1 Oligonucleotides

A. Oligonucleotide Design: Subsequent to the initial description of a cDNA encoding murine ICAM-1 (Ballantyne et al., *Nucleic Acids Research*, 1989, 17, 5853), additional sequence information concerning the 5'-untranslated region (%'-UTR) was published (Ballantyne et al., *Genomics*, 1992, 14, 1076). This sequence information was used to design a set of 2'-modified oligonucleotides targeted to the 5'-UTR of the murine ICAM-1 gene (Table 7). Compounds were evaluated via FACS® using monoclonal antibodies to murine ICAM-1 conjugated to phycoerythrin (PharMingen, San Diego, Calif.).

B. Activities of Murine 5'-UTR ICAM-1 Oligonucleotides: The 5'-UTR-targeted oligonucleotides were evaluated for their ability to modulate ICAM-1 expression in a dose-responsive manner in murine bEND.3 cells (Table 14). Isosequence 2'-methoxyethoxy modified compounds ISIS 15163 (phosphodiester linkages) and ISIS 15164 (phosphorothioate linkages) showed dose responses comparable to that of ISIS 3082 and are therefore preferred. The 2'-fluoro-modified compound ISIS 12472 also showed about 40% inhibition of ICAM-1 at a dose of 50 nM and is thus also preferred.

TABLE 14

Dose Response of Murine bEND.3 Cells to ICAM-1 5'-UTR Antisense Oligonucleotides[1]

| ISIS # | SEQ ID NO: | ASO Gene Target | Dose | % Protein Expression | % Protein Inhibition |
|---|---|---|---|---|---|
| basal | — | LIPOFECTIN ® | 0 nM | 0.0% | — |
| induced[2] | — | — | 0 nM | 100.0% | — |
| 3082 | 14 | 5'-UTR | 12.5 nM | 74.4% | 25.6% |
| 3082 | 14 | " | 25 nM | 62.2% | 37.8% |
| 3082 | 14 | " | 50 nM | 34.1% | 65.9% |
| 3082 | 14 | " | 100 nM | 4.6% | 95.4% |
| 12472 | 20 | 5'-UTR | 12.5 nM | 91.8% | 8.2% |
| 12472 | 20 | " | 25 nM | 77.7% | 22.3% |
| 12472 | 20 | " | 50 nM | 62.9% | 37.1% |
| 12472 | 20 | " | 100 nM | 57.4% | 42.6% |
| 14282 | 21 | 5'-UTR | 12.5 nM | 109.8% | — |
| 14282 | 21 | " | 25 nM | 113.6% | — |
| 14282 | 21 | " | 50 nM | 90.5% | 9.5% |
| 14282 | 21 | " | 100 nM | 125.2% | — |
| 15163 | 22 | 5'-UTR | 12.5 nM | 60.8% | 39.2% |
| 15163 | 22 | " | 25 nM | 28.3% | 71.7% |
| 15163 | 22 | " | 50 nM | 33.9% | 66.1% |
| 15163 | 22 | " | 100 nM | 18.9% | 81.1% |
| 15164 | 22 | 5'-UTR | 12.5 nM | 75.8% | 24.2% |
| 15164 | 22 | " | 25 nM | 54.8% | 45.2% |
| 15164 | 22 | " | 50 nM | 45.8% | 54.2% |
| 15164 | 22 | " | 100 nM | 32.2% | 67.8% |
| 15699 | 23 | 5'-UTR | 12.5 nM | 114.0% | — |
| 15699 | 23 | " | 25 nM | 92.3% | 7.7% |
| 15699 | 23 | " | 50 nM | 126.5% | — |
| 15699 | 23 | " | 100 nM | 153.9% | — |
| 15722 | 24 | 5'-UTR | 12.5 nM | 106.1% | — |
| 15722 | 24 | " | 25 nM | 102.2% | — |
| 15722 | 24 | " | 50 nM | 77.0% | 23.0% |
| 15722 | 24 | " | 100 nM | 84.7% | 15.3% |
| 15724 | 25 | 5'-UTR | 12.5 nM | 103.9% | — |
| 15724 | 25 | " | 25 nM | 93.4% | 6.6% |
| 15724 | 25 | " | 50 nM | 102.8% | — |
| 15724 | 25 | " | 100 nM | 103.0% | — |

[1]After overnight incubation (t~18 h).
[2]For details of induction, see the Examples.

Example 8

Optimization of Chemistry of ISIS 3082 Derivatives

In this Example, various chemical modifications are made to an antisense compound targeted to murine ICAM-1, ISIS 3082.

A. Isosequence Compound Design: ISIS 3082 is a phosphorothioate oligonucleotide having SEQ ID NO: 14. A variety of isosequence derivatives, having 2'-methoxyethoxy modifications, 5-methyl-cytosines in place of cytosine residues, and/or modified backbone linkages were prepared (Table 5). Also prepared were an oligonucleotide having a sequence shifted 6 bases relative to that of ISIS 3082 (ISIS 16825) and a scrambled control oligonucleotide (ISIS 14153).

B. Murine ICAM-1- and VCAM-1-Specific Probes: A cDNA clone of murine ICAM-1 was obtained using a published sequence (Siu et al., *J. Immunol.*, 1989, 143, 3813; see also GenBank accession No. M31585, locus name "MUSICAM1B") and the reverse transcriptase/polymerase chain reaction (RT-PCR; see Beverley, pages 15-13 to 15-15, and Dorit, pages 15-21 to 15-27, in: *Short Protocols in Molecular Biology*, 2nd Ed., Ausubel et al., eds., John Wiley & Sons, New York, 1992). Briefly, poly-A RNA was isolated from TNF-treated bEND.3 cells, and an oligo-dT primer and RT were used to synthesize a double-stranded (mRNA:DNA) template for PCR reactions. In PCR reactions, the following phosphodiester oligonucleotides were used as primers:

| ISIS Sequence | SEQ ID NO: |
|---|---|
| 3815 5'-AATACCGGATCCGGAATTCCGGGTGCAGGTAGCAGCGGAGCT | 30, and |
| 3816 5'-TTCGCTCTAGACAGGAAGACATAAAAACTTTATTGAT | 31. |

The sequence of the 5' primer, ISIS 3815, includes a BamHI site (underlined) and an extended sequence that corresponds to the sense strand of the murine ICAM-1 sequence (emboldened and double-underlined). The sequence of the 3' primer, ISIS 3816, includes an XbaI site (underlined) and an extended sequence that corresponds to the antisense strand of the murine ICAM-1 sequence (emboldened and double-underlined). The resulting PCR product was digested with XbaI and BamHI in order to generate a DNA molecule having cohesive ends, and ligated into a BamHI-restricted expression vector. Digestion of the resultant expression construct with HindIII yields a ~1.3 kb fragment that was purified and radiolabeled (using a Prime-It® random primer labeling kit, Stratagene, La Jolla, Calif.) before being used as probe for murine ICAM-1 in the following experiments.

In order to demonstrate the specificity of compounds targeted to ICAM-1, levels of VCAM-1 mRNA were also determined. In order to generate a murine VCAM-1-specific probe, a radiolabeled VCAM-1-specific PCR product was prepared using RNA from bEND.3 cells and a pair of phosphodiester oligonucleotides,
5'-TGCCTGTGAAGATGGTCGCGG (5' sense primer, SEQ ID NO: 32) and
5'-ACCATGTCTCCTGTCTTTGCT (3' antisense primer, SEQ ID NO: 33), as primers in PCR reactions using a PRIME-A-GENE® labeling kit (Promega, Madison, Wis.). The resultant $^{32}$P-cytosine-radiolabelled 1,933-bp product hybridizes to the open reading frame of murine VCAM-1 (nucleotides 59–1991 of GenBank Accession No. M84487, locus name "MUSVCAM1A").

For either of the above probes, other PCR probes can be prepared, or one or more of the oligonucleotides of Tables 4–7 can be detectably labeled and used as a murine ICAM-1-specific probe using methods known in the art.

C. Activities of ISIS 3082 Derivatives: In an initial screen for activity, the derivatives of ISIS 3802 described in Table 5 were tested via FACS® for their ability to reduce ICAM-1 protein levels on bEND.3 cells. The results demonstrate that ISIS 7744 and 13318 were as active as, and ISIS 13814 and 13315 were more active than, ISIS 3082 in this assay. These compounds are thus preferred embodiments of the invention; ISIS 13315 is particularly preferred it consistently demonstrated a high level of activity.

Northern assays were used to examine the effect of the ISIS 3082 derivatives on ICAM-1 mRNA levels. As shown in Table 15, ISIS 13815 (a 2'-MOE/m5c gapmer derived from ISIS 3082) depressed murine ICAM-1 mRNA levels somewhat better than the parent compound. Specifically, at t=4 h, ISIS 13815 caused over 80% inhibition of ICAM-1 mRNA, whereas ISIS 3082 caused only about 60% inhibition at the same timepoint. At t=24 h, ISIS 13815 caused about 60% inhibition, whereas ISIS 3082 caused about 50% inhibition. ISIS 13815 is therefore a preferred embodiment of the invention.

The specificity of the antisense compounds for ICAM-1 was confirmed by the fact that levels of VCAM-1 mRNA remained at about 70 to 90% of control (induced) levels at t=4 h.

TABLE 15

Activity of "Second Generation" 5' Cap Antisense Oligonucleotides (ASOs) Targeted to Mouse ICAM-1

| ISIS No: | SEQ ID NO: | Relative VCAM-1 mRNA Level | % VCAM-1 Control | Relative ICAM-1 mRNA Level | % ICAM-1 Control |
|---|---|---|---|---|---|
| EXPT. 1 (50 nM, t = 4 h): | | | | | |
| basal[1] | — | 1.0 | 0.2% | 1.0 | 0.0% |
| induced[2] | — | 5.7 | 100.0% | 38.1 | 100.0% |
| 3082 | 14 | 5.1 | 89.5% | 14.9 | 39.1% |
| 13815 | 14 | 4.2 | 73.7% | 6.9 | 18.0% |
| 14153[3] | 16 | 4.3 | 75.4% | 22.6 | 59.0% |
| 15163 | 22 | 4.2 | 73.7% | 37.5 | 98.4% |
| 15164 | 22 | 3.9 | 68.4% | 37.8 | 99.0% |
| EXPT. 2 (50 nM, t = 24 h): | | | | | |
| basal[1] | — | — | — | 1.0 | 0.0% |
| induced[2] | — | — | — | 2.5 | 100.0% |
| 3082 | 14 | — | — | 1.3 | 52.0% |
| 13815 | 14 | — | — | 1.0 | 40.0% |
| 14153[3] | 16 | — | — | 1.5 | 60.0% |
| 15163 | 22 | — | — | 8.0 | 320.0% |
| 15164 | 22 | — | — | 21.3 | 852.0% |

[1]Basal = cells treated with LIPOFECTIN ® only.
[2]For details of induction, see the Examples.
[3]ISIS 14153 = 3082 scrambled control.

Example 9

3'-UTR-Targeted Murine ICAM-1 Oligonucleotides

A. Oligonucleotide Design: Antisense compounds targeted to the 3'-untranslated region (3'-UTR) of human ICAM-1 are potent inhibitors of ICAM-1 expression. Particularly preferred, as described in Example 4, is ISIS 15389, a hemimer wherein the eight 3'-most residues are 2'-methoxyethoxy-modified and which has 5-methyl cytosine (m5c) substituted for cytosine throughout its nucleobase sequence. ISIS 15389 is targeted to a region that is about 450 bases 3' from the human ICAM-1 stop codon. A similar compound, ISIS 17481, targeted to a region that is about 780 bases 3' from the stop codon of murine ICAM-1, was developed for the mouse gene. The structures of ISIS 17481, a 2'-methoxyethoxy hemimer oligonucleotide targeted to the 3'-UTR of the murine ICAM-1 gene, and of various control oligonucleotides therefor, are described in Table 6.

B. Activity of ISIS 17481: The 5'-UTR-targeted oligonucleotides were evaluated for their ability to inhibit murine ICAM-1 expression in a dose-dependent fashion. As is shown in Table 16, ISIS 17481 is a potent inhibitor of ICAM-1 expression. For example, at a dose of 25 nM, ISIS 17481 caused about 75% inhibition of ICAM-1, whereas ISIS 3082 caused only about 50% inhibition at the same dose. Moreover, the ISIS 17481-mediated inhibition of ICAM-1 increased to about 90% at a dose of 50 nM, whereas ISIS 3082 caused only about 55% inhibition at the same dose in these experiments.

TABLE 16

Activity of ISIS 17481 and Control
Antisense Oligonucleotides (ASOs) in bEND.3 Cells[1]

| ISIS # | SEQ ID NO: | ICAM-1 Intragenic Target and ASO Structure | Dose | % Protein Expression | % Protein Inhibition |
|---|---|---|---|---|---|
| basal | — | LIPOFECTIN ® only | 0 nM | 100.0% | 0.0% |
| 3082 | 14 | 3'-UTR; | 25 nM | 48.9% | 51.1% |
| 3082 | 14 | phosphorothioate, | 50 nM | 45.6% | 54.4% |
| 3082 | 14 | 2'-deoxy, no m5c | 100 nM | 19.8% | 80.2% |
| 3082 | 14 |  | 200 nm | 11.2% | 88.8% |
| 17481 | 3 | 3'-UTR; | 25 nM | 26.8% | 73.2% |
| 17481 | 3 | phosphorothioate, | 50 nM | 10.2% | 89.8% |
| 17481 | 3 | 2'-MOE hemimer, | 100 nM | 8.5% | 71.5% |
| 17481 | 3 | fully m5c | 200 nM | 2.2% | 97.8% |
| 20441 | 29 | ISIS 17481 1 base | 25 nM | 70.0% | 30.0% |
| 20441 | 29 | mismatch control | 50 nM | 83.0% | 17.0% |
| 20441 | 29 |  | 100 nM | 73.0% | 27.0% |
| 20441 | 29 |  | 200 nM | 90.0% | 10.0% |
| 20440 | 28 | ISIS 17481 2 base | 25 nM | 81.2% | 18.8% |
| 20440 | 28 | mismatch control | 50 nM | 63.5% | 36.5% |
| 20440 | 28 |  | 100 nM | 83.5% | 16.5% |
| 20440 | 28 |  | 200 nM | 98.0% | 2.0% |
| 20439 | 27 | ISIS 17481 3 base | 25 nM | 76.0% | 24.0% |
| 20439 | 27 | mismatch control | 50 nM | 65.0% | 35.0% |
| 20439 | 27 |  | 100 nM | 63.2% | 16.8% |
| 20439 | 27 |  | 200 nM | 61.0% | 39.0% |
| 20438 | 26 | ISIS 17481 | 25 nM | 84.0% | 16.0% |
| 20438 | 26 | scrambled control | 50 nM | 83.0% | 17.0% |
| 20438 | 26 |  | 100 nM | 70.0% | 30.0% |
| 24038 | 26 |  | 200 nM | 61.0% | 39.0% |

[1]After overnight incubation (t~18 h).

Example 10

Animal Models for ICAM-1 Modulation

A. Allograft Survival: A murine model for evaluating compounds for their ability to inhibit heart allograft rejection has been previously described (Stepkowski et al., *J. Immunol.*, 1994, 153, 5336). This model was used to evaluate the immunosuppressive capacity of the enhanced antisense compounds to ICAM-1. Heart allograft rejection studies and oligonucleotide treatments of BALB/c mice were performed essentially as previously described (Stepkowski et al., *J. Immunol.*, 1994, 153, 5336). Antisense oligonucleotides used included ISIS 3082 (SEQ ID NO: 14, phosphorothioate linkages, no 2'-MOE, no m5c) and isosequence derivative ISIS 13315 (a 2'-MOE/m5c gapmer). Dosages used were 2.5 and 5 mg/kg/day for seven days. The survival times of the transplanted hearts and their hosts were monitored and recorded.

The mean survival time for untreated mice was 7.8±0.8 days (7, 7, 8, 8 and 9 days). Treatment of the mice for 7 days with ISIS 3082 increased the mean survival time to 12.0±2.7 days (9, 10, 12, 13 and 16 days) at a dose of 2.5 mg/kg/day and to 14.1±2.7 days at a dose of 5 mg/kg/day. Similarly, treatment of mice with ISIS 13315 increased the mean survival time to 12.0±1.6 days (9, 10, 12, 13 and 16 days) at a dose of 2.5 mg/kg/day and to 13.0±1.7 days at a dose of 5 mg/kg/day. These results indicate that the 2'-methoxyethoxy- and 5-methyl-cytosine-modified antisense compounds of the invention can be used therapeutically to modulate graft rejection and other ICAM-1-mediated immunoresponsive events.

B. DSS-Induced Colitis: A murine model of colitis, induced by dextran sulfate sodium (DSS), has been described by Bennett et al. (*J. Pharm. Exp. Therapeutics*, 1997, 280, 988). This model system was used to evaluate the activity of ISIS 3082 and ISIS 13315, a 2'-methoxyethoxy "gapmer" isosequence derivative of ISIS 3082. Mice were treated with DSS for seven days to induce colitis; oligonucleotide treatment (1 mg/kg/day, diluted in sterile saline, s.c. injection) began on the same day as DSS administration. Disease Activity Indices (DAIS) were scored and calculated as described (Bennett et al., *J. Pharm. Exp. Therapeutics*, 1997, 280, 988). The results (FIG. 1) demonstrate that ISIS 13315 was nearly as effective as ISIS 3082 in preventing DSS-induced colitis in mice.

Example 11

Limiting Viral Dissemination via Inhibition of Cellular Adhesion

Adhesion molecules have been proposed to be mediators of viral dissemination in several systems. For example, in the case of the retrovirus, human immunodeficiency virus (HIV), studies have demonstrated that adhesion of infected cells to immobilized ICAM-1 induces HIV replication (Shattock et al., *J. Infect. Dis.*, 1996, 174, 54), and surface expression of ICAM-1 (CD54) is enhanced in T cell lines carrying the virus (Imai et al., *Int. J. Cancer*, 1993, 55, 811).

The association between adhesion molecules and human cytomegalovirus (CMV) is of particular interest. CMV is a member of the Herpesviridae family that is associated with worldwide morbidity and mortality in immunocompromised hosts (Sedmak et al., *Arch. Virol.*, 1995, 140, 111). CMV is known to infect multiple tissues and organs, but its mechanism(s) of dissemination are largely uncharacterized. Viral dissemination by the bloodstream has been suggested, but acceptance of the notion of hematogenous spread of CMV has been limited due to the fact that in vitro studies generally indicate that peripheral blood mononuclear cells (PBMCs) do not support the complete viral reproductive cycle. However, PBMCs can be infected by CMV by contact with virally infected endothelial cell monolayers (Waldman et al., *J. Infect. Dis.*, 1995, 171, 263).

ICAM-1 and other cellular adhesion molecules are up-regulated in fibroblasts infected with CMV (Grundy et al., *Immunol.*, 1993, 78, 405). Effective antiviral treatment with ganciclovir or foscarnet accentuates such up-regulation of adhesion molecules, suggesting that CMV immediate/ early gene expression, which is not blocked by such treatment, is responsible for such CMV-mediated up-regulation of adhesion molecules (Craigen et al., Transplantation, 1996, 62, 1102).

CMV has been associated with allograft rejection, particularly transplant-associated arteriosclerosis. However, the role CMV plays in the development of transplant-associated arteriosclerosis remains unclear (Knight et al., Transplantation, 1997, 63, 1366). Even effective antiviral treatment of the transplant recipient with, e.g., ganciclovir or foscarnet, might not block allograft rejection as CMV infected cells could continue to provide a focus of proinflammatory activity, which could contribute to undesirable immunopathology and/or accentuate graft rejection or graft-versus-host disease (Craigen et al., Transplantation, 1996, 62, 1102). Treatment of transplant tissues ex vivo, and/or of transplant recipients in vivo, with inhibitors of cellular adhesion molecules (alone or in combination with antiviral agents) is expected to modulate viral-mediated up-regulation of such adhesion molecules and thus block such undesirable events.

In order to investigate the role of adhesion molecules such as ICAM-1 in viral dissemination, and to determine the potential of antisense oligonucleotides to prevent viral dissemination, the following experiments were carried out. Endothelial cells (ECs) were treated with ISIS 15537, 17425 or control oligonucleotide ISIS 14118 prior to CMV inoculation, incubated an additional 48 hours post-inoculation and examined by FACS. The results demonstrate specific and significant attenuation of CMV-mediated ICAM-1 expression by these antisense compounds. The attenuation of ICAM-1 expression was reflected by reduced adhesion of $^{51}$Cr-labeled T cells to oligonucleotide-treated CMV EC monolayers. These assays were performed essentially as described by Bennett et al. (J. Immunol., 1994, 152, 3530) except that (1) T cells were used instead of HL-60 cells as adherent cells and (2) $^{51}$Cr was used instead of calcein to label the adherent cells.

Example 12

Therapeutic Methods

The antisense compounds of the invention result in immunosuppressive and anti-inflammatory effects in vivo and may be used by those skilled in the art to provide prophylactic, palliative and therapeutic benefit to an animal, including a human, in need of such effects. The antisense compounds of the invention are also evaluated for their ability to inhibit the metastasis of cancer cells and are used to provide prophylactic, palliative or therapeutic relief from hyperproliferative disorders. Therapeutic methods using the antisense compounds of the invention include, but are not limited to, the following examples.

A. Modulation of Undesirable Immunoresponsive Events: The present invention provides a method of modulating immunoresponsive events that are mediated or influenced, either directly or indirectly, by ICAM-1 in an animal. Such immunoresponsive events can lead to undesirable effects such as, e.g., inflammation. The method of modulating immunoresponsive events mediated or influenced by ICAM-1 comprises administering one or more of the antisense compounds of the invention (or a combination thereof with one or more anti-inflammatory or immunosuppressive non-antisense-based agents or NABAS; see below), in a pharmaceutical preparation if required, to the animal. Some specific therapeutic modalities for the antisense compounds of the invention follow as examples but are not intended to limit the scope of the invention.

1. Diapedesis: The present invention provides a method of modulating ICAM-1-mediated diapedesis in an animal comprising administering one or more of the antisense compounds of the invention, or a combination thereof with one or more anti-inflammatory or immunosuppressive agents, in a pharmaceutical preparation if required, to the animal. Diapedesis, the transendothelial migration of immunoresponsive cells (such as leukocytes) from the circulatory system into injured or infected tissues, is thought to be a key event in inflammatory injury (for a review, see Albelda et al., FASEB J., 1994, 8, 504). Administration of the antisense compounds of the invention, as part of an appropriate pharmaceutical composition if required, to an animal is expected to inhibit diapedesis and subsequent undesired immunoresponsive events such as, for example, inflammation and inflammatory damage. Such treatment may be in combination with one or more anti-inflammatory and/or immunosuppressive NABAs (see below). Such administration can be systemic or directly to the site(s) of diapedesis, inflammation and/or inflammatory damage. The antisense compounds of the invention are evaluated for their ability to modulate diapedesis and subsequent undesired inflammation and/or inflammatory damage using, for example, the assays described in the references cited in this section, or in the in vitro flow model of Luscinskas et al. (J. Immunol., 1996, 157, 326), and/or appropriate animal models.

2. Allograft Rejection and GVHD: The present invention also provides a method of avoiding allograft rejection including treating or preventing graft versus host disease (GVHD) in an animal comprising administering one or more of the antisense compounds of the invention, or a combination thereof with one or more anti-inflammatory or immunosuppressive agents, in a pharmaceutical preparation if required, to the animal. Administration of one or more of the PECAM-1-modulating antisense compounds of the invention, in combination with other agents and as part of an appropriate pharmaceutical composition if required, to an animal is expected to modulate allograft rejection and GVHD. Such administration can be systemic or directly to the area(s) of the transplanted tissue(s) or organ(s), or administered ex vivo to tissue(s) or organ(s) prior to their transplantation. Such treatment may be in combination with one or more anti-inflammatory/immunosuppressive NABAs (see below). The antisense compounds of the invention are evaluated for their ability to modulate allograft rejection using one or more assays known in the art and/or one or more appropriate animal models (see, e.g., Stepkowski et al., J. Immunol., 1994, 153, 5336, and Example 21 in U.S. Pat. No. 5,514,788 to Bennett et al.).

3. Arthritis: The present invention also provides a method of treating various forms of arthritis in an animal comprising administering one or more of the antisense compounds of the invention, or a combination thereof with one or more anti-inflammatory or immunosuppressive agents, in a pharmaceutical preparation if required, to the animal. Such administration can be systemic or directly to involved tissues such as, e.g., synovial fluid. Increased expression of CAMs, including ELAM-1, VCAM-1, ICAM-1 and PECAM-1 has been detected in synovial fluid from patients having rheumatoid arthritis (Tak et al., Clin. Immunol. Immunopathol., 1995, 77, 236) . Such forms of arthritis include, for example, autoimmune forms of arthritis, including some forms of rheumatoid arthritis (RA), psoriatic arthritis (PA) and ankylosing spondylitis (AS); non-autoimmune forms of RA, PA and AS; infectious arthritis, such as results from infection with spirochetes (Lyme Disease, also known as LD or Lyme Arthritis, is caused by *Borrelia burgdorferi,* and some instances of Reiter's Syndrome, RS, appear to be associated with *Chlamydia trachomatis*), bacterial infection (staphylococci such as *Hemophilus influenzae,* streptococci, pneumococci, gram-negative bacilli and the like), viral infection (e.g., rubella, mumps, human parvovirus or hepatitis B), and/or fungal infection (e.g., *Sporothrix schenckii, Coccidioides immitis, Blastomyces dermatididis* or *Candida albicans*) (see *The Merck Manual of Diagnosis and Therapy,* 15th Ed., pp. 1239–1267, Berkow et al., eds., Rahay, N.J., 1987). Such treatment may be in combination with one or more additional anti-inflammatory/immunosuppressive NABAs and, additionally or alternatively, when the arthritis to be treated results at least in part from infection of the animal by a pathogen, with one or more antibiotics (see below). The antisense compounds of the invention are evaluated for their ability to modulate arthritis and inflammatory damage resulting therefrom using one or more assays known in the art and/or one or more appropriate animal models (see, e.g., published PCT application No. WO 95/32285 to Benoist et al.).

4. Inflammatory Disorders of the Bowel: The present invention also provides a method of treating various inflammatory disorders of the bowel in an animal comprising administering one or more of the antisense compounds of the invention, or a combination thereof with one or more anti-inflammatory or immunosuppressive agents, in a pharmaceutical preparation if required, to the animal. Such disorders include, for example, Chrohn's disease (CD) and other forms of regional enteritis; and various forms of colitis including ulcerative colitis (UC) and granulomatous, ischemic and radiation colitis (see *The Merck Manual of Diagnosis and Therapy,* 15th Ed., pp. 797–806, Berkow et al., eds., Rahay, N.J., 1987). Such treatment may be in combination with one or more additional antisense compounds or anti-inflammatory and/or immunosuppressive NABAs (see below). The antisense compounds of the invention are evaluated for their ability to modulate a inflammatory disorder of the bowel using one or more assays known in the art and/or one or more appropriate animal models (see, e.g., Example 20 in U.S. Pat. No. 5,514,788 to Bennett et al. and Okayasu et al., *Gastroenterol.,* 1990, 98, 694).

5. Autoimmune Diseases and Disorders: The present invention also provides a method of treating various autoimmune diseases and disorders including but not limited to autoimmune thyroid disorders; autoimmune forms of arthritis; multiple sclerosis (MS); some forms of juvenile diabetes mellitus; myasthenia gravis; pemphigus vulgaris; and systemic lupus erythematosus (SLE or lupus) (for a review of autoimmune disorders, see Steinman, *Sci. Amer.,* 1993, 269, 107). A preferred embodiment of the invention involves the treatment or prevention of autoimmune thyroid disorders, such as, e.g., Graves' Disease (thyrotoxicosis), Hashimoto's disease and De Quervain thyroiditis, as PECAM-1 has been observed to be expressed on cells involved in such conditions (Marazuela et al., *Clin. Exp. Immunol.,* 1995, 102, 328; Aubert et al., *Clin. Immunol. Immunopathol.,* 1995, 76, 170). Administration of the antisense compounds of the invention, as part of an appropriate pharmaceutical composition if required, to an animal is expected to prevent or inhibit the development of the autoimmune disease and subsequent undesired events. Such treatment may be in combination with one or more anti-inflammatory/immunosuppressive NABAs (see below). Such administration can be systemic or directly to a specific tissue, depending on the nature of the disorder. For example, systemic administration might be more appropriate for SLE, whereas direct administration to the thyroid gland or adjacent tissues might be more efficacious in the case of Graves' Disease. The antisense compounds of the invention are evaluated for their ability to prevent or inhibit autoimmune diseases using appropriate assays and animal models known to those skilled in the art (see, for example, Burkhardt et al., *Rheumatol. Int.,* 1997, 17, 91).

B. Cardiovascular Disorders: The present invention provides a method of modulating undesirable events that are mediated or influenced, either directly or indirectly, by ICAM-1 in an animal during or following cardiovascular injury or during the course of a cardiovascular disease or disorder. The method of modulating immunoresponsive events mediated or influenced by ICAM-1 comprises administering one or more of the antisense compounds of the invention, in a pharmaceutical preparation if required, to the animal. Some specific therapeutic modalities for the antisense compounds of the invention follow as examples but are not intended to limit the scope of the invention.

1. Myocardial Ischemia/Reperfusion Injury: The present invention provides a method of reducing or preventing myocardial ischemia/reperfusion (MI/R) injury in an animal comprising administering one or more of the antisense compounds of the invention, or a combination thereof with one or more anti-inflammatory or immunosuppressive agents, in a pharmaceutical preparation if required, to the animal. Coronary artery reperfusion is an effective treatment for patients with acute myocardial infarction. However, reperfusion itself often leads to enhanced injury of myocardial tissue. Transmigration of PMNs into the ischemic myocardium is believed to play some role in myocardial ischemia/reperfusion injury (Entman et al., *FASEB J.,* 1991, 5, 2529; Lefer et al., *FASEB J.,* 1991, 5, 2029). ICAM-1 is up-regulated, absolutely and relative to PECAM-1, in myocardial tissue isolated from human hearts failing from either dilated cardiomyopathy, acute myocarditis or ischemic heart disease (Devaux et al., *European Heart J.,* 1997, 18, 470). Administration of the antisense compounds of the invention, as part of an appropriate pharmaceutical composition if required, to an animal is expected to modulate MI/R injury. Such administration can be systemic or directly to the circulatory system. The antisense compounds of the invention are evaluated for their ability to modulate MI/R injury using one or more assays known in the art and/or one or more appropriate animal models such as, e.g., those described in the references cited in this section.

2. Stroke-Related Damage: The present invention provides method of reducing leukocyte-induced damage in an animal during or following a stroke or series of strokes, or of preventing leukocyte-induced damage from a stroke in an animal known to be prone to having strokes, in an animal comprising administering one or more of the antisense compounds of the invention, in a pharmaceutical preparation if required, to the animal. A stroke is a blockage or hemorrhage of a blood vessel in or leading to the brain (e.g., aneurysmal subarachnoid hemorrhage) that causes inadequate blood supply (ischemia) to the brain. After brain ischemia, leukocytes adhere to the perturbed vascular endothelium and are believed to aggravate reperfusion injury eventually leading, in some cases, to chronic vasospasm (i.e., a sudden constriction of an artery or vein), which in turn can have serious and undesired consequences. Adhesion molecules, including ICAM-1, are up-regulated in acute infarctions from brain sections of human subjects who died within 18 days of ischemic stroke (Lindsberg et al., Circ., 1996, 94, 939). In an animal model, a monoclonal antibody to ICAM-1 inhibited vasospasm (Oshiro et al., Stroke, 1997, 28, 2031). Administration of the antisense compounds of the invention, as part of an appropriate pharmaceutical composition if required, to an animal is expected to stroke-related injuries. Such administration can be systemic or directly to the circulatory system. The antisense compounds of the invention are evaluated for their ability to modulate stroke-related injury using one or more assays known in the art and/or one or more appropriate animal models such as, for example, those described in the references cited in this section.

C. Treatment of Hyperproliferative Disorders: Patients having benign tumors, and primary malignant tumors that have been detected early in the course of their development, may often be successfully treated by the surgical removal of the benign or primary tumor. If unchecked, however, cells from malignant tumors are spread throughout a patient's body through the processes of invasion and metastasis. Invasion refers to the ability of cancer cells to detach from a primary site of attachment and penetrate, e.g., an underlying basement membrane. Metastasis indicates a sequence of events wherein (1) a cancer cell detaches from its extracellular matrices, (2) the detached cancer cell migrates to another portion of the patient's body, often via the circulatory system, and (3) attaches to a distal and inappropriate extracellular matrix, thereby created a focus from which a secondary tumor can arise. Normal cells do not possess the ability to invade or metastasize and/or undergo apoptosis (programmed cell death) if such events occur (Ruoslahti, Sci. Amer., 1996, 275, 72).

Disseminating precancerous or cancerous cells often display ectopic expression of adhesion molecules which may facilitate step (3) of the metastatic process as described above. Examples of such adhesion molecules include ICAM-1 and other CAMs (for a review, see Tang et al., Invasion Metastasis, 1994, 14, 109). Thus, modulation of ICAM-1 using the antisense compounds of the invention may result in a decreased ability of disseminating cancer cells to attach to a distal and/or inappropriate matrix, thereby modulating metastasis of the primary tumor. The present invention thus also provides a method of modulating or preventing metastasis in an animal comprising administering one or more of the antisense compounds of the invention, in a pharmaceutical preparation if required, to the animal. Such treatment may be in combination with one or more additional anticancer antisense compounds or chemotherapeutic NABAs (see below). The antisense compounds of the invention are evaluated for their ability to modulate metastasis using one or more assays known in the art and/or one or more appropriate animal models (see, e.g., Examples 16–18 in U.S. Pat. No. 5,514,788 to Bennett et al.).

D. Treatment of Pathogenic Disorders

A number of reports have indicated associations between pathogenic diseases or disorders and the up-regulation of ICAM-1. In addition to the effects of viruses on the expression of adhesion molecules, ICAM-1 up-regulation has been implicated in the initiation, growth, maintenance and/or spread of the following pathogenic states. One or more of the antisense compounds of the invention may be used, alone or in combination with other agents, to prevent or treat such diseases and disorders. Prophylactically or therapeutically effective amounts of one or more of the antisense compounds of the invention are administered to a patient in need thereof in order to prevent or treat such diseases and disorders.

*Borrelia burgdorferi* is a spirochete that is believed to be the causative agent of Lyme disease (also known as LD or Lyme arthritis). Acellular preparations of *B. burgdorferi* induce the expression of cellular adhesion molecules, including ICAM-1 (Boggemeyer et al., Cell. Adhes. Commun., 1994, 2, 145). A water-soluble version of the anti-inflammatory agent prednisolone (prednisolone-21-hemisuccinate) protects against *B. burgdorferi*-induced arthritic joint swelling in SCID mice and reduces the expression of ICAM-1 in murine bEND.3 cells (Hurtenbach et al., Int. J. Immunopharmacol., 1996, 18, 281).

Up-regulation of ICAM-1, and other cellular adhesion molecules, has been implicated in the pathogenesis of oral lichen planus (Regezi et al., Oral Surg. Med. Oral Pathol. Oral radiol. Endob., 1996, 81, 682). In the case of *Plasmodium falciparum*, the causative agent of malaria, during the course of infections, merozites released from infected hepatocytes must undergo several cycles of multiplication within erythrocytes (red blood cells, RBCs) before the onset of clinical disease. During each such cycle, mature infected erythrocytes sequester by binding to endothelial cells. It has been suggested that ICAM-1, present on vascular endothelial cells is a cytoadherence receptor for infected red blood cells (IRBCs) (Ockenhouse et al., J. Infect. Dis., 1991, 164, 163). IRBC adhesion is particularly strong to the combination of ICAM-1 with CD36 (Udomsangpetch et al., J. Immunol., 1997, 158, 4358).

E. Combination Therapies and Compositions

If desired, the therapeutic antisense modulation of the expression of ICAM-1 can be combined with additional therapies in order to achieve a requisite level of interference with, or prevention of, undesirable disorders or diseases. Such combinations can be carried out, for example, by simultaneously administering two or more antisense compounds targeted to ICAM-1, or, in treating an animal having inflammation, an antisense compound targeted to ICAM-1 in combination with a non-antisense-based anti-inflammatory or immunosuppressive agent. If an animal having a hyperproliferative disease or disorder is to be treated, the antisense compound targeted to ICAM-1 may be combined with a second anticancer agent, which may be a second antisense compound or a non-antisense-based agent (NABA). When used with the antisense compounds of the invention, such second agents may be used in simple combination (e.g., administration of a NABA and an antisense compound), sequentially (e.g., administration of a first NABA and an antisense compound for a period of time followed by administration of a second NABA and an antisense compound), or in combination with one or more other such non-antisense-based agents or physical treatments (e.g., administration of a NABA and an antisense compound, or, in the treatment of hyperproliferative disorders for example, administration of one or more NABAs and antisense compounds in combination with radiotherapy). When two (or more) antisense compounds, or a combination of one or more antisense compounds and one or more NABAs, are to be administered simultaneously in a treatment regime, one preferred composition is one comprising a lipid vesicle, particularly a sterically stabilized lipid vesicle, comprising both (or all) of the compounds. In the context of the invention, the term "treatment regimen" is meant to encompass therapeutic, palliative and prophylactic modalities.

1. Combinations of Antisense Compounds: Two or more antisense compounds can be administered simultaneously as described above. Combination treatments can also be carried out by first (1) administering a first composition comprising a first antisense compound targeted to ICAM-1 (or a combination thereof with one or more anti-inflammatory/immunosuppressive or chemotherapeutic agents) for a first period of time and then (2) "switching" to administration of a second composition comprising a second antisense compound targeted to ICAM-1 (or a combination thereof with one or more anti-inflammatory or chemotherapeutic agents) for a second period of time.

Whether administered simultaneously or sequentially, for treatment of hyperproliferative disorders such as cancer, preferred pairings of antisense compounds include those targeted to molecules that mediate cellular hyperproliferation, such as: (1) ICAM-1 and a Ras protein; (2) ICAM-1 and a Raf kinase; and (3) ICAM-1 and protein kinase C. Antisense compounds targeted to Ras, Raf kinase and protein kinase C proteins are described in U.S. Pat. Nos. 5,563,255, 5,576,208, 5,582,972, 5,582,986, 5,620,963, 5,646,265, 5,654,284, 5,656,612, 5,661,134, 5,681,747 and 5,703,054.

For treatment of virally caused diseases, such as CMV retinitis, preferred pairings of antisense compounds include those targeted to molecules that limit or prevent the growth of such viruses, such as: (1) ICAM-1 and cytomegalovirus (CMV), or (2) ICAM-1 and human immunodeficiency virus (HIV). Antisense compounds targeted to CMV and HIV, and methods of using such compounds, are described in U.S. Pat. Nos. 5,166,195, 5,442,049, 5,523,389, 5,591,600, 5,591,720, 5,595,978 and 5,607,923.

2. Combinations with Chemotherapeutic Agents: For the purpose of treating hyperproliferative disorders, the antisense compounds of the invention can additionally or alternatively be used in combination with non-antisense-based chemotherapeutic agents. Examples of such agents that can be used in combination with the antisense compounds of the invention include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, nitrogen mustards, melphalan, methylcyclohexylnitrosurea, cyclophosphamide, 6-mercaptopurine, 6-thioguanine, cytarabine (CA), 5-azacytidine, hydroxyurea, deoxycoformycin, colchicine, 5-fluorouracil (5-FU), 4-hydroxyperoxycyclophosphoramide, 5-fluorodeoxyuridine (5-FUdR), methotrexate (MTX), vincristine, vinblastine, etoposide, trimetrexate, teniposide, cisplatin and diethylstilbestrol (DES). (See, generally, *The Merck Manual of Diagnosis and Therapy*, 15th Ed., pp. 1206–1228, Berkow et al., eds., Rahay, N.J., 1987).

3. Combinations with Anti-Inflammatory/Immunosuppressive Agents: Examples of non-antisense-based anti-inflammatory or immunosuppressive agents that can be used in combination with the antisense compounds of the invention include but are not limited to salicylates; nonsteroidal anti-inflammatory drugs (NSAIDs), including indomethacin, ibuprofen, fenopofen, ketoprofen, naproxen, piroxicam, phenylbutazone, oxyphenbutazone, sulindac and meclofenamate; gold compounds, such as auranofin; D-penicillamine; cyclophosphamide; methotrexate; azathioprine; colchicine; hydroxychloroquine; corticotropin; steroids and corticosteroids such as, for example, hydrocortisone, deoxyhydrocortisone, fludrocortisone, prednisolone, methylprednisolone, prednisone, triamcinolone, dexamethasone, betamethasone and paramethasone. See, generally, *The Merck Manual of Diagnosis and Therapy*, 15th Ed., pp. 1239–1267 and 2497–2506, Berkow et al., eds., Rahay, N.J., 1987). In the case of oral lichen planus, preferred anti-inflammatory NABAs include antihistamines, such as, e.g., hydroxyzine or chlorpheniramine; triamcinolone acetonide; flurandrenolide; tretinoin; corticosteroids, such as, e.g., prednisone; and/or retinoids (see *The Merck Manual of Diagnosis and Therapy*, 15th Ed., pp. 2286–2287, Berkow et al., eds., Rahay, N.J., 1987).

4. Combinations with Antibiotics: The present invention provides compositions and methods of preventing or treating pathogenic infection of an animal comprising administering one or more of the antisense compounds of the invention to an animal, in a pharmaceutical preparation if required. Such compositions and methods can be used alone or in combination with other antibiotic agents.

Those skilled in the art will appreciate that the choice of antibiotic(s) to be used will depend on the nature of the pathogen(s) and the stage of the disease. For example, in the case of *B. burgdorferi* infections, antisense compounds targeted to ICAM-1 can be used in combination with one or more penicillin derivatives and/or tetracycline (see, generally, *The Merck Manual of Diagnosis and Therapy*, 15th Ed., pp. 1251–1253, Berkow et al., eds., Rahay, N.J., 1987). In the case of malaria, combinations with chloroquine, quinine, pyrimethamine, a sulfonamide and/or primaquine are preferred (see *The Merck Manual of Diagnosis and Therapy*, 15th Ed., pp. 205–208, Berkow et al., eds., Rahay, N.J., 1987). Other antibiotics that can be combined with the antisense compounds of the invention include but are not limited to nafcillin (gram-positive cocci); penicillin G (gram-negative cocci); gentamicin and/or piperacillin (gram-negative bacilli); and one or more tetracyclines, one or more penicillin derivatives, erythromycin, doxycylcine, chloramphenicol and/or streptomycin (spirochetes such as, e.g., *Borrelia burgdorferi* and *Treponema pallidum*). See, generally, *The Merck Manual of Diagnosis and Therapy*, 15th Ed., pp. 132–136, 236–243, 1239–1267 and 1918–1919, Berkow et al., eds., Rahay, N.J., 1987).

Some forms of arthritis (e.g., Lyme disease) result from infection of an animal by a pathogen, such as a bacteria or spirochete, and subsequent immune system-mediated events, e.g., inflammation. In such cases, and other situations wherein undesired inflammation results from infection from a pathogen, one or more antibiotics may also be used in combination with an antisense compound of the invention in further combination with an anti-inflammatory or immunosuppressive agent (see above).

One skilled in the art will appreciate that, depending on the cause and stage of development of an undesired immune response resulting from pathogenic infection, it may be preferable in some instances to administer, either simultaneously or sequentially, more complex combinations. That is, the present invention encompasses more complex compositions and treatment regimes such as those comprising, for example, (1) one or more antisense compounds targeted to ICAM-1, (2) one or more antibiotics, and (3) one or more anti-inflammatory/immunosuppressive NABAs.

What is claimed is:

1. An antisense oligonucleotide comprising from about 8 to about 30 nucleotides connected by covalent linkages, wherein said antisense oligonucleotide comprises a nucleobase sequence specifically hybridizable with a nucleic acid encoding a human intercellular adhesion molecule-1, wherein said antisense compound modulates the expression of said human intercellular adhesion molecule-1 and wherein said oligonucleotide comprises at least one 2'-modification.

2. The antisense oligonucleotide of claim 1 wherein said 2'-modification is a 2'-methoxyethoxy modification.

3. The antisense oligonucleotide of claim 2 wherein said 2'-methoxyethoxy modification is present on the most 3' residue of said oligonucleotide.

4. The antisense oligonucleotide of claim 3, wherein every cytosine nucleobase of said oligonucleotide is substituted by a 5-methyl cytosine nucleobase.

5. The antisense oligonucleotide of claim 1, further comprising at least one 5-methyl cytosine nucleobase in place of a cytosine nucleobase.

6. The antisense oligonucleotide of claim 1 wherein said cellular adhesion molecule-1 is human cellular adhesion molecule-1.

7. The antisense oligonucleotide of claim 6 wherein said nucleobase sequence is SEQ ID NO: 2, 5, 6, 7 or 8.

8. A pharmaceutical composition comprising the antisense oligonucleotide of claim 6 and a pharmaceutically acceptable carrier.

9. A method of modulating the synthesis of intercellular adhesion molecule-1 in a cell or tissue comprising contacting the cell or tissue in-vitro with the antisense oligonucleotide of claim 1.

10. An antisense oligonucleotide that modulates the expression of human intercellular adhesion molecule-1, wherein said oligonucleotide has the structure:

GsCsCsCsAsAsGsCsTsGsGsCsAsTsCsGsTsCsA, wherein:

"s" is a phosphorothioate linkage;

"A", "C", "T" and "G" are 2'-deoxy-adenoine, cytidine, thymidine and guanosine nucleoside residues, respectively;

"A" is an adenosine nucleoside residue comprising a 2' modification;

"T" is a thymidine nucleoside residue comprising a 2' modification;

"G" is a guanosine nucleoside residue comprising a 2' modification; and

"C" is a 5-methyl-cytidine nucleoside residue comprising a 2' modification.

11. The antisense oligonucleotide of claim 10, wherein said 2'-modification is 2'-methoxyethoxy and said oligonucleotide is ISIS 13280.

12. The antisense oligonucleotide of claim 10, wherein said 2'-modification is 2'-fluoro and said oligonucleotide is ISIS 12604.

13. A pharmaceutical composition comprising the antisense oligonucleotide of claim 10 and a pharmaceutically acceptable carrier.

14. An antisense oligonucleotide that modulates the expression of human intercellular adhesion molecule-1, wherein said oligonucleotide is ISIS 14725 having the structure:

GsCsCsCsAsAsGsCsTsGsGsCsAsTsCsCsGsTsCsA, wherein:

"s" is a phosphorothioate linkage;

"A", "C", "T" and "G" are 2'-deoxy-adenosine, cytidine, thymidine and guanosine nucleoside residues, respectively;

"A" is a 2'-methoxyethoxy adenosine nucleoside residue;

"T" is a 2'-methoxyethoxy thymidine nucleoside residue;

"G" is a 2'-methoxyethoxy guanosine nucleoside residue; and

"C" is a 2'-methoxyethoxy 5-methyl-cytidine nucleoside residue.

15. A pharmaceutical composition comprising the antisense oligonucleotide of claim 14 and a pharmaceutically acceptable carrier.

16. An antisense oligonucleotide that modulates the expression of human intercellular adhesion molecule-1, wherein said oligonucleotide is ISIS 15839 having the structure:

GsCsCsCsAsAsGsCsTsGsGsCsAsTsCsGsTsCsA, wherein:

"s" is a phosphorothioate linkage;

"A", "T" and "G" are 2'-deoxy-adenosine, thymidine and guanosine nucleoside residues, respectively;

"C" is a 2'-deoxy-5-methyl-cytidine nucleoside residue;

"A" is a 2'-methoxyethoxy adenosine nucleoside residue;

"T" is a 2'-methoxyethoxy thymidine nucleoside residue;

"G" is a 2'-methoxyethoxy guanosine nucleoside residue; and

"C" is a 2'-methoxyethoxy 5-methyl-cytidine nucleoside residue.

17. A pharmaceutical composition comprising the antisense oligonucleotide of claim 16 and a pharmaceutically acceptable carrier.

18. An antisense oligonucleotide that modulates the expression of human intercellular adhesion molecule-1, wherein said oligonucleotide is ISIS 16824 having the structure:

CsCsAsAsGsCsTsGsGsCsAsTsCsCsGsTsCsA, wherein:

"s" is a phosphorothioate linkage;

"A", "C", "T" and "G" are 2'-deoxy-adenosine, cytidine, thymidine and guanosine nucleoside residues, respectively;

"A" is a 2'-methoxyethoxy adenosine nucleoside residue;
"T" is a 2'-methoxyethoxy thymidine nucleoside residue;
"G" is a 2'-methoxyethoxy guanosine nucleoside residue; and
"C" is a 2'-methoxyethoxy 5-methyl-cytidine nucleoside residue.

19. A pharmaceutical composition comprising the antisense oligonucleotide of claim 18 and a pharmaceutically acceptable carrier.

20. An antisense oligonucleotide that modulates the expression of human intercellular adhesion molecule-1, wherein said oligonucleotide is ISIS 16823 having the structure:

AsAsGsCsTsGsGsCsAsTsCsCsGsTsCsA, wherein:
"s" is a phosphorothioate linkage;
"A", "C", "T" and "G" are 2'-deoxy-adenosine, cytidine, thymidine and guanosine nucleoside residues, respectively;
"A" is a 2'-methoxyethoxy adenosine nucleoside residue;
"T" is a 2'-methoxyethoxy thymidine nucleoside residue;
"G" is a 2'-methoxyethoxy guanosine nucleoside residue; and
"C" is a 2'-methoxyethoxy 5-methyl-cytidine nucleoside residue.

21. A pharmaceutical composition comprising the antisense oligonucleotide of claim 20 and a pharmaceutically acceptable carrier.

22. An antisense oligonucleotide that modulates the expression of human intercellular adhesion molecule-1, wherein said oligonucleotide is ISIS 16158 having the structure:

GsTsGsCsCsCsAsAsGsCsTsGsGsCsAsTsCsCsGsT, wherein:
"s" is a phosphorothioate linkage;
"A", "C", "T" and "G" are 2'-deoxy-adenosine, cytidine, thymidine and guanosine nucleoside residues, respectively;
"A" is a 2'-methoxyethoxy adenosine nucleoside residue;
"T" is a 2'-methoxyethoxy thymidine nucleoside residue;
"G" is a 2'-methoxyethoxy guanosine nucleoside residue; and
"C" is a 2'-methoxyethoxy 5-methyl-cytidine nucleoside residue.

23. A pharmaceutical composition comprising the antisense oligonucleotide of claim 22 and a pharmaceutically acceptable carrier.

24. An antisense oligonucleotide that modulates the expression of human intercellular adhesion molecule-1, wherein said oligonucleotide is ISIS 16159 having the structure:

AsGsCsAsGsTsGsTsGsCsCsCsAsAsGsCsTsGsGsCsAsT, wherein:
"s" is a phosphorothioate linkage;
"A", "C", "T" and "G" are 2'-deoxy-adenosine, cytidine, thymidine and guanosine nucleoside residues, respectively;
"A" is a 2'-methoxyethoxy adenosine nucleoside residue;
"T" is a 2'-methoxyethoxy thymidine nucleoside residue;
"G" is a 2'-methoxyethoxy guanosine nucleoside residue; and
"C" is a 2'-methoxyethoxy 5-methyl-cytidine nucleoside residue.

25. A pharmaceutical composition comprising the antisense oligonucleotide of claim 24 and a pharmaceutically acceptable carrier.

26. An antisense oligonucleotide comprising from about 8 to about 30 nucleotides connected by covalent linkages, wherein said antisense oligonucleotide comprises at least an 8 nucleobase portion of SEQ ID NO: 3, 11, 20 or 22, and wherein said antisense oligonucleotide encodes a murine intercellular adhesion molecule-1 and modulates the expression of the murine intercellular adhesion molecule-1.

27. An antisense oligonucleotide that modulates the expression of murine intercellular adhesion molecule-1, wherein said oligonucleotide is ISIS 17481 having the structure:

TsCsCsCsAsCsAsGsCsAsGsCsTsTsGsCsAsCsGsA, wherein:
"s" is a phosphorothioate linkage;
"A", "T" and "G" are 2'-deoxy-adenosine, thymidine and guanosine nucleoside residues, respectively;
"C" is a 2'-deoxy-5-methyl-cytidine nucleoside residue;
"A" is a 2'-methoxyethoxy adenosine nucleoside residue;
"T" is a 2'-methoxyethoxy thymidine nucleoside residue;
"G" is a 2'-methoxyethoxy guanosine nucleoside residue; and
"C" is a 2'-methoxyethoxy 5-methyl-cytidine nucleoside residue.

* * * * *

UNITED STATES PATENT AND TRADEMARK OFFICE
CERTIFICATE OF CORRECTION

PATENT NO.   : 6,111,094                                           Page 1 of 2
DATED        : August 29, 2000
INVENTOR(S)  : Bennett et al.

It is certified that error appears in the above-identified patent and that said Letters Patent is hereby corrected as shown below:

Column 6,
Line 26, please delete "oligonucleotidel" and insert -- oligonucleotide --.

Column 30,
Line 1, please delete "133" and insert -- 1633 --.

Column 35,
Line 43, please insert -- A. -- before "Oligonucleotides".
Line 44, please delete "M-1" and insert -- Human ICAM-1 --.

Column 36,
Line 34, please delete "GCCAAGCTGGCATCCGTCA" and insert

--GCCAAGCTGGCATCCGTCA--.

Line 39, please delete "GCCCAAGCTGGCATCCGTCA" and insert

--GCCCAAGCTGGCATCCGTCA--.

Column 37,
In second line of footnote 1 of Table 2, please delete "C" and insert --C--.
Table 3, column 2, row 3, please delete
"ToCoToGoAoGoToAoGoCoAoGoAoGoGoAoGoCoToC" and insert --
ToCoToGoAoGoToAoGoCoAoGoAoGoGoAoGoCoToC--.

Table 3, column 2, row 4, please delete
"TsCsTsGsAsGsTsAsGsCsAsGsAsGsGsAsGsCsTsC"
TsCsTsGsAsGsTsAsGsCsAsGsAsGsGsAsGsCsTsC--. and insert --

Table 4, column 2, row 6, please delete
"GsAsTsCsGsCsGsTsCsGsGsAsCsTsAsTsGsAsAsG"
--GsAsTsCsGsCsGsTsCsGsGsAsCsTsAsTsGsAsAsG--. and insert --

UNITED STATES PATENT AND TRADEMARK OFFICE
CERTIFICATE OF CORRECTION

PATENT NO.   : 6,111,094
DATED         : August 29, 2000
INVENTOR(S)  : Bennett et al.

It is certified that error appears in the above-identified patent and that said Letters Patent is hereby corrected as shown below:

Column 39,
Table 4, column 2, row 7, please delete
" ToGoCoAoToCoCoCoCsCsAsGsGsCsCsAoCoCoAoT" and insert --
ToGoCoAoToCoCoCoCsCsAsGsGsCsCsAoCoCoAoT-- .

Table 4, column 2, row 8, please delete
" TsGsCsAsTsCsCsCsCsCsAsGsGsCsCsAsCsCsAsT" and insert --
TsGsCsAsTsCsCsCsCsCsAsGsGsCsCsAsCsCsAsT-- .

Table 4, column 2, row 9, please delete
" TsGsCsAsTsCsCsCsCsCsAsGsGsCsCsAsCsCsAsT" and insert --
TsGsCsAsTsCsCsCsCsCsAsGsGsCsCsAsCsCsAsT-- .

Column 42,
Line 47, please insert -- % -- between "0.1" and "SDS"

Column 54,
Line 31, please delete "DAIS" and insert -- DAIs --.

Column 83, claim 10,
Line 49, please delete "adenoine" and insert -- adenosine --.

Signed and Sealed this

Eighth Day of January, 2002

*Attest:*

*Attesting Officer*

JAMES E. ROGAN
*Director of the United States Patent and Trademark Office*